(12) United States Patent
Brandhuber et al.

(10) Patent No.: US 7,144,988 B2
(45) Date of Patent: Dec. 5, 2006

(54) METHOD OF STRUCTURE-BASED DRUG DESIGN TO CREATE OR IMPROVE MODULATORS OF IL-1 ACTIVITY WHICH BIND TO THE INTERLEUKIN-1 TYPE 1 RECEPTOR

(75) Inventors: Barbara J. Brandhuber, Golden, CO (US); Guy P. A. Vigers, Boulder, CO (US)

(73) Assignee: Array Biopharma, Inc., Boulder, CO (US)

( * ) Notice: Subject to any disclaimer, the term of this patent is extended or adjusted under 35 U.S.C. 154(b) by 434 days.

(21) Appl. No.: 10/389,012

(22) Filed: Mar. 14, 2003

(65) Prior Publication Data

US 2004/0014643 A1    Jan. 22, 2004

Related U.S. Application Data

(60) Provisional application No. 60/364,996, filed on Mar. 15, 2002.

(51) Int. Cl.
*C07K 1/00*    (2006.01)

(52) U.S. Cl. .................. 530/351; 530/350; 530/412; 530/418

(58) Field of Classification Search .............. None
See application file for complete search history.

(56) References Cited

OTHER PUBLICATIONS

Vigers et al. X-ray crystal structure of small antagonist peptide bound to interleukin-1 receptor type 1. J. Biol. Chem. 275 (47), 36927-36933 (2000).*
Vigers et al. Crystal structure of type-1 interleukin-1 receptor complexed with interleukin-1beta. Nature 386, 190-194 (1997).*
Schreuder et al. A new cytokine-receptor binding mode revealed by crystal structure of IL-1 receptor with antagonist. Nature, 386, 194-200 (1997).*

* cited by examiner

*Primary Examiner*—Nashaat T. Nashed
(74) *Attorney, Agent, or Firm*—McDonnell Boehnen Hulbert & Berghoff LLP

(57) ABSTRACT

Crystals comprising a modified interleukin-1 type 1 receptor (IL-1R1) and one or more modulators of IL-1 activity are described. Methods of identifying potential inhibitors of IL-1 activity are also described. Compositions and methods for the treatment of IL-1 mediated diseases, such as rheumatoid arthritis, osteoarthritis, and other inflammatory conditions, are described.

4 Claims, 4 Drawing Sheets

K205-P206 cleavage site

```
10         20         30         40         50         60
|          |          |          |          |          |
MKVLLRLICF IALLISSLEA DKCKEREEKI ILVSSANEID VRPCPLNPNE HKGTITWYKD 70         80         90         100        110        120
|          |          |          |          |          |
DSKTPVSTEQ ASRIHQHKEK LWFVPAKVED SGHYYCVVRN SSYCLRIKIS AKFVENEPNL 130        140        150        160        170        180
|          |          |          |          |          |
CYNAQAIFKQ KLPVAGDGGL VCPYMEFFKN ENNELPKLQW YKDCKPLLLD NIHFSGVKDR 190        200        210        220        230        240
|          |          |          |          |          |
LIVMNVAEKH RGNYTCHASY TYLGKQYPIT RVIEFITLEE NKPTRPVIVS PANETMEVDL 250        260        270        280        290        300
|          |          |          |          |          |
GSQIQLICNV TGQLSDIAYW KWNGSVIDED DPVLGEDYYS VENPANKRRS TLITVLNISE 310        320        330        340        350        360
|          |          |          |          |          |
IESRFYKHPF TCFAKNTHGI DAAYIQLIYP VTNFQKHMIG ICVTLTVIIV CSVFIYKIFK 370        380        390        400        410        420
|          |          |          |          |          |
IDIVLWYRDS CYDFLPIKAS DGKTYDAYIL YPKTVGEGST SDCDIFVFKV LPEVLEKQCG 430        440        450        460        470        480
|          |          |          |          |          |
YKLFIYGRDD YVGEDIVEVI NENVKKSRRL IIILVRETSG FSWLGGSSEE QIAMYNALVQ 490        500        510        520        530        540
|          |          |          |          |          |
DGIKVVLLEL EKIQDYEKMP ESIKFIKQKH GAIRWSGDFT QGPQSAKTRF WKNVRYHMPV 550        560
|          |
QRRSPSSKHQ LLSPATKEKL QREAHVPLG
```

Figure 2

SEQUENCE LISTING

<160> NUMBER OF SEQ ID NOS: 2

<210> SEQ ID NO 1
<211> LENGTH: 569
<212> TYPE: PRT
<213> ORGANISM: Homo sapiens

<400> SEQUENCE: 1

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270
```

Val Leu Gly Glu Asp Tyr Tyr Ser Val Glu Asn Pro Ala Asn Lys Arg
            275                 280                 285

Arg Ser Thr Leu Ile Thr Val Leu Asn Ile Ser Glu Ile Glu Ser Arg
        290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
        435                 440                 445

Arg Leu Ile Ile Ile Leu Val Arg Glu Thr Ser Gly Phe Ser Trp Leu
    450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
    530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

<210> SEQ ID NO 2
<211> LENGTH: 205
<212> TYPE: PRT
<213> ORGANISM: Homo sapiens

<400> SEQUENCE: 2

Leu Glu Ala Asp Lys Cys Lys Glu Arg Glu Lys Ile Ile Leu Val
1               5                   10                  15

Ser Ser Ala Asn Glu Ile Asp Val Arg Pro Cys Pro Leu Asn Pro Asn
            20                  25                  30

Glu His Lys Gly Thr Ile Thr Trp Tyr Lys Asp Asp Ser Lys Thr Pro
        35                  40                  45

Val Ser Thr Glu Gln Ala Ser Arg Ile His Gln His Lys Glu Lys Leu
    50                  55                  60

Trp Phe Val Pro Ala Lys Val Glu Asp Ser Gly His Tyr Tyr Cys Val
65                  70                  75                  80

```
                        -continued

Val Arg Asn Ser Ser Tyr Cys Leu Arg Ile Lys Ile Ser Ala Lys Phe
            85                  90              95

Val Glu Asn Glu Pro Asn Leu Cys Tyr Asn Ala Gln Ala Ile Phe Lys
            100             105             110

Gln Lys Leu Pro Val Ala Gly Asp Gly Gly Leu Val Cys Pro Tyr Met
        115             120             125

Glu Phe Phe Lys Asn Glu Asn Asn Glu Leu Pro Lys Leu Gln Trp Tyr
        130             135             140

Lys Asp Cys Lys Pro Leu Leu Leu Asp Asn Ile His Phe Ser Gly Val
145             150             155             160

Lys Asp Arg Leu Ile Val Met Asn Val Ala Glu Lys His Arg Gly Asn
            165             170             175

Tyr Thr Cys His Ala Ser Tyr Thr Tyr Leu Gly Lys Gln Tyr Pro Ile
            180             185             190

Thr Arg Val Ile Glu Phe Ile Thr Leu Glu Glu Asn Lys
            195             200             205
```

METHOD OF STRUCTURE-BASED DRUG DESIGN TO CREATE OR IMPROVE MODULATORS OF IL-1 ACTIVITY WHICH BIND TO THE INTERLEUKIN-1 TYPE 1 RECEPTOR

FIELD OF THE INVENTION

The present invention relates to crystals comprising a modified Interleukin-1 type 1 receptor (IL-1R1) and one or more modulators of IL-1 activity. Methods of identifying potential inhibitors of IL-1 activity by structure-based drug design are also provided. The present invention also relates to compositions and methods for the treatment of IL-1 mediated diseases, such as rheumatoid arthritis, osteoarthritis, and other inflammatory conditions.

BACKGROUND OF THE INVENTION

Interleukin-1 (IL-1) is a potent inflammatory cytokine and is a key mediator in many diseases and medical conditions. IL-1 activity is mediated by IL-1α and IL-1β, which are related polypeptides, both of which bind the IL-1 type 1 receptor (IL-1R1) and are expressed by many cells, including those of the macrophage/monocyte lineage. IL-1 stimulates cellular responses by interacting with a heterodimeric receptor complex comprised of two transmembrane proteins, IL-1R1 and IL-1 receptor accessory protein (IL-1RAcP). IL-1 forms a complex with IL-1R1, which recruits IL-1RAcP (Greenfeder et al., 1995, *J. Biol. Chem.* 270: 13757–13765; Yoon and Dinarello, 1998, *J. Immunology* 160:3170–3179; Cullinan et al., 1998, *J. Immunology* 161: 5614–5620). Cell-based binding studies suggest that IL-1RAcP stabilizes the IL-1R1 signaling complex by slowing the ligand off-rate (Wesche et al., 1998, *FEBS Letters* 429:303–306). IL-1RAcP has no significant affinity for either IL-1 or IL-1R1 alone, but high affinity for the IL-1: IL-1R1 complex (Ettorre et al., 1997, *Eur. Cytokine Netw.* 8:161–171).

The IL-1 receptor antagonist (IL-1ra) competes with IL-1α and β for receptor binding but fails to recruit IL-1RAcP, resulting in an occupied but non-signaling receptor. IL-1 activity is also regulated by IL-1 type 2 receptor (IL-1R2), which is a decoy receptor that binds ligand but does not participate in signaling due to a truncated intracellular domain. IL-1ra and IL-1R2 reduce the severity and duration of IL-1 mediated inflammatory events by inhibiting IL-1 signaling (Wesche et al., 1998, *FEBS Letters* 429: 303–306; Dripps et al., 1991, *J. Biol. Chem.* 266:10331–10336; Dripps et al., 1991, *J. Biol. Chem.* 266: 20331–20335).

IL-1 inhibitors may block IL-1 activity by down-regulating IL-1 expression, binding free IL-1, interfering with IL-1 binding to its receptor, interfering with formation of the IL-1 receptor complex (i.e., association of IL-1 receptor with IL-1 receptor accessory protein), or interfering with modulation of IL-1 signaling after binding to its receptor. Several classes of interleukin-1 inhibitors are known, including interleukin-1 receptor antagonists such as IL-1ra, anti-IL-1 receptor monoclonal antibodies (e.g., EP 623674), the disclosure of which is hereby incorporated by reference, IL-1 binding proteins such as soluble IL-1 receptors (e.g., U.S. Pat. No. 5,492,888, U.S. Pat. No. 5,488,032, and U.S. Pat. No. 5,464,937, U.S. Pat. No. 5,319,071, and U.S. Pat. No. 5,180,812, the disclosures of which are hereby incorporated by reference), anti-IL-1 monoclonal antibodies (e.g., WO 95/01997, WO 94/02627, WO 90/06371, U.S. Pat. No. 4,935,343, EP 364778, EP 267611 and EP 220063, the disclosures of which are hereby incorporated by reference), IL-1 receptor accessory proteins and antibodies thereto (e.g., WO 96/23067 and WO 99/37773, the disclosures of which are hereby incorporated by reference), inhibitors of IL-1β converting enzyme (ICE) or caspase I (e.g., WO 99/46248, WO 99/47545, and WO 99/47154, the disclosures of which are hereby incorporated by reference), which can be used to inhibit IL-1β production and secretion, IL-1β protease inhibitors, and other compounds and proteins which block in vivo synthesis or extracellular release of IL-1.

Exemplary IL-1 inhibitors are disclosed in the following references: U.S. Pat. Nos. 5,747,444; 5,359,032; 5,608,035; 5,843,905; 5,359,032; 5,866,576; 5,869,660; 5,869,315; 5,872,095; 5,955,480; 5,965,564; International (WO) patent applications 98/21957, 96/09323, 91/17184, 96/40907, 98/32733, 98/42325, 98/44940, 98/47892, 98/56377, 99/03837, 99/06426, 99/06042, 91/17249, 98/32733, 98/17661, 97/08174, 95/34326, 99/36426, 99/36415; European (EP) patent applications 534978 and 89479; French patent application FR 2762514. The disclosures of all of the aforementioned references are hereby incorporated by reference.

Several IL-1 receptor antagonist peptides have been identified from phage-display libraries, including a 21-mer IL-1 antagonist peptide (AF10847) with an $IC_{50}$ of 2.6 nM and a tetra-peptoid (referred to herein as 3891_11a) with an $IC_{50}$ of 6.7 μM (WO 96/29088, the disclosure of which is hereby incorporated by reference). The chemical structure of 389_11a is shown in FIG. 1. These molecules appear to be pure receptor antagonists, like IL-1ra.

The three-dimensional structures of IL-1ra (Vigers et al., 1994, *J. Biol. Chem.* 269:12874–12879) and IL-1β (von Oostrum, 1991, *J. Struct. Biol.* 107:189) have been elucidated using X-ray crystallography. A construct expressing the extracellular portion of IL-1R1 (IL-1R1_EC) was used by Vigers et al. to solve co-crystal structures of the IL-1R1_EC:IL-1β complex (Vigers et al., 1997, *Nature* 386:190–194) and IL-1R1_EC:AF10847 complex (Vigers et al., 2000, *J. Biol. Chem.* 275:36927–36933). A similar method was used to solve the structure of IL-1R1_EC:IL-1Ra (Shreuder et al., 1997, *Nature* 386:194–200). These studies indicate that IL-1R1_EC contains three immunoglobulin-like (Ig-like) domains. The first two Ig-like domains of IL-1R1_EC are tightly linked, while the third domain is attached by a flexible linker. IL-1β (and presumably IL-1α) binds to IL-1R1 at two sites. The first site (Site A) is at the junction of the first and second Ig-like domains, and the second site (Site B) is on the face of the third domain. Most of the interactions for IL-1ra and AF10847 are located at site A while the third Ig-like domain does not contribute substantially to the binding affinity (Vigers et al., 2000, *J. Biol. Chem.* 275:36927–36933).

Small molecules with conventional drug-like characteristics that bind IL-1R1 and inhibit IL-1 activity are of great therapeutic interest. There is a need in the art for effective small molecule inhibitors of the IL-1 signaling pathway that may ameliorate the effects of IL-1 mediated diseases. Particularly, there is a need for clinically relevant small molecule inhibitors that are suitable for delivery into human patients.

SUMMARY OF THE INVENTION

The invention provides a modified IL-1 type 1 receptor that can co-crystallize with small molecule receptor modulators. The invention also provides methods of using such crystals to identify small molecule inhibitors useful for treating IL-1 mediated diseases.

A modified IL-1 type 1 receptor of the invention comprises two immunoglobulin-like domains of the IL-1 type 1 receptor and is designated IL1R2D. IL1R2D does not bind with high affinity to IL-1, but binds with high affinity to IL-1 receptor antagonist (IL-1ra). As provided herein, protein-ligand complexes of IL1R2D and small molecules can be crystallized in a form suitable for determining the three dimensional structure of the crystalline complexes. The invention provides methods for using the crystal coordinates of the crystalline complexes to design modulators of IL-1 activity. The three dimensional structure is also useful for identifying potential modulators of IL-1 activity.

In certain aspects, the invention relates to a crystal of a modified IL-1 type 1 receptor protein-ligand complex, wherein the modified IL-1 type 1 receptor comprises the first two immunoglobulin domains of the IL-1R1 (approximately amino acids 18 to 222 of SEQ ID NO: 1 (SEQ ID NO: 2)). A crystal of the invention effectively diffracts X-rays for the determination of atomic coordinates of the protein-ligand complex to a resolution of greater than 3.5 Angstroms. In certain aspects, the protein-ligand complex can comprise more than one copy of a particular ligand or multiple ligands. In other aspects, a ligand of the protein-ligand complex can have a molecular weight of less than about 1500 g/mol.

In a particular aspect, the invention provides a crystal of a protein-ligand complex that comprises a modified IL-1 type 1 receptor and two copies of the IL-1 inhibitor 389__11a, wherein the modified IL-1 type 1 receptor comprises amino acids 18 to 222 of SEQ ID NO: 1 (SEQ ID NO: 2). In one aspect, the crystal has a space group R3 and a unit cell of dimensions a =96.3 Å, b =96.3 Å, and c =75.3 Å. In another aspect, the crystal has a three-dimensional structure characterized by the atomic structure coordinates of Table 3.

The invention also provides methods of identifying a compound that binds to interleukin-1 type 1 receptor (IL-1R1) using a crystal of a modified IL-1 type 1 receptor protein-ligand complex. In a particular aspect, a compound that binds IL-1R1 can be identified by performing structure-based drug design with the atomic coordinates determined for the crystal in conjunction with computer modeling. Computer modeling can be conducted using one of many techniques, including for example inspecting the structure of the IL1R2D:ligand complex to identify fragments that might bind to the receptor with favorable energetics, or by the computational screening of libraries of small molecules to find those that might bind to IL-1R1, or by similar techniques well known to those skilled in the art.

A compound identified by a method of the invention can be contacted with IL-1 type 1 receptor or a ligand binding fragment thereof to determine if the compound can bind IL-1 type 1 receptor or a ligand binding fragment thereof. A compound is selected that binds to the IL-1 type 1 receptor or a ligand binding fragment thereof. Binding can be detected, for example, using a labeled substrate to compete with the compound for binding to IL-1 type 1 receptor or a ligand binding fragment thereof. Binding can also be directly detected, for example, by BIAcore analysis (BIAcore, Inc.). In one aspect of the invention, a selected compound can be examined for its ability to modulate IL-1. The invention also provides a method for using a crystal of a modified IL-1 type 1 receptor protein-ligand complex in a drug screening assay. In certain aspects of the invention, the method involves (a) selecting a compound by performing structure-based drug design with the atomic coordinates determined for a crystal of a modified IL-1 type 1 receptor protein-ligand complex, wherein said selecting is performed in conjunction with computer modeling; (b) contacting the IL-1 protein with IL-1 type 1 receptor or ligand binding fragment thereof in the presence or absence of the compound; and (c) measuring the activity of IL-1 protein in the presence and absence of the compound; wherein a compound that inhibits the activity of IL-1 is selected as a potential drug. In certain aspects, a compound selected as a potential drug can be crystallized with a modified IL-1 type 1 receptor, and the crystal can be used in a drug screening assay as described above.

The invention further provides a method of using a modified IL-1R1 comprising amino acids 18 to 222 of SEQ ID NO: 1 (SEQ ID NO: 2) to grow a crystal of a protein-ligand complex comprising: contacting the modified IL-1R1 with a ligand, wherein the modified IL-1R1 forms a protein-ligand complex with the ligand; and growing the crystal of the protein-ligand complex. Preferably, the crystal effectively diffracts X-rays for the determination of the atomic coordinates of the protein-ligand complex to a resolution of greater than 3.5 Angstroms. In a particular aspect, the crystal is grown by hanging drop vapor diffusion.

Specific preferred embodiments of the present invention will become evident from the following more detailed description of certain preferred embodiments and the claims.

BRIEF DESCRIPTION OF THE DRAWINGS

FIG. 1 depicts the chemical structure of the IL-1 inhibitor 389__11a.

FIG. 2 depicts the amino acid sequence of full-length IL-1 type 1 receptor (SEQ ID NO: 1), as reproduced from Swiss-Prot entry P14778. Residues 1–17 are the putative signal sequence and residues 18–336 are the extracellular domain of IL-1R1. Residues 18 to 222 (SEQ ID NO: 2) comprise the first two immunoglobulin-like domains of the mature receptor, and compose IL-1R2D.

DETAILED DESCRIPTION OF CERTAIN PREFERRED EMBODIMENTS

Figure 1:
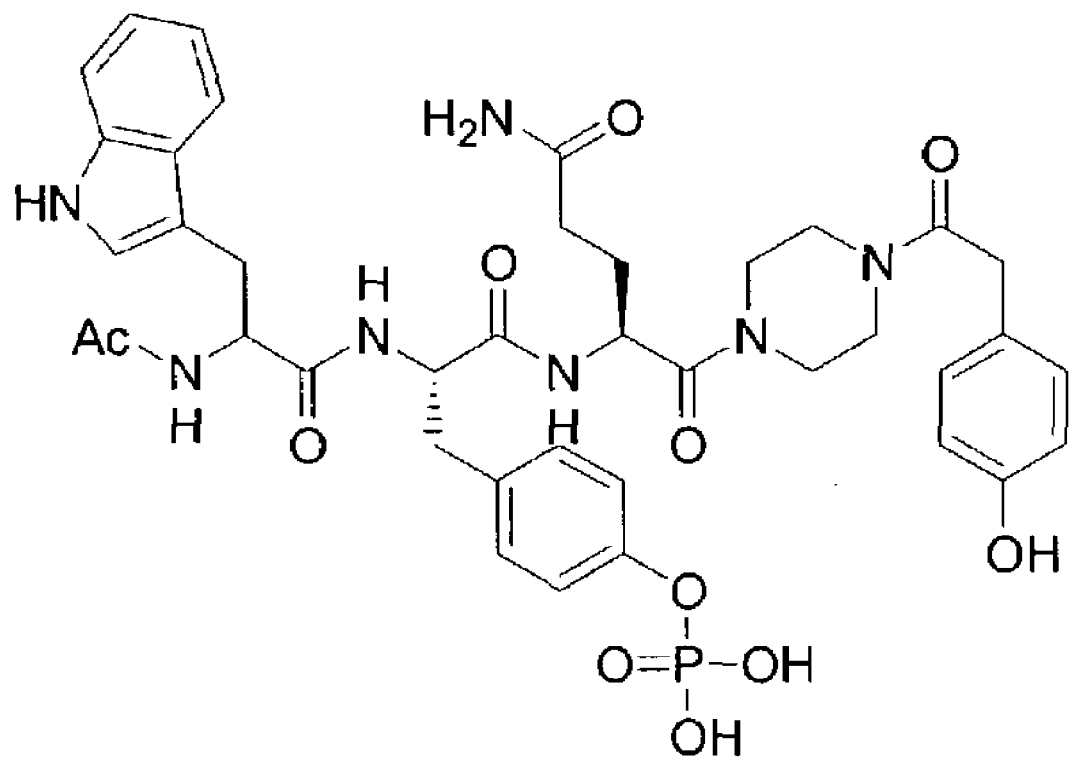

The section headings used herein are for organizational purposes only and are not to be construed as limiting the subject matter described. All references cited in this application are expressly incorporated by reference herein for any purpose.

Definitions

A disease or medical condition is considered to be an "interleukin-1 (IL-1) mediated disease" if the spontaneous or experimental disease or medical condition is associated with elevated levels of IL-1 in bodily fluids or tissue or if cells or tissues taken from the body produce elevated levels of IL-1 in culture. In many cases, such IL-1 mediated diseases are also recognized by the following additional two conditions: (1) pathological findings associated with the disease or medical condition can be mimicked experimentally in animals by administration of IL-1 or upregulation of expression of IL-1; and (2) a pathology induced in experimental animal models of the disease or medical condition can be inhibited or abolished by treatment with agents that inhibit the action of IL-1. In most IL-1 mediated diseases at least two of the three conditions are met, and in many IL-1 mediated diseases all three conditions are met.

The term "IL-1 mediated disease" includes, but is not limited to, acute pancreatitis; ALS; Alzheimer's disease; cachexia/anorexia, including aids-induced cachexia; asthma and other pulmonary diseases; atherosclerosis; autoimmune vasculitis; chronic fatigue syndrome; *Clostridium*-associated illnesses, including *Clostridium*-associated diarrhea; coronary conditions and indications, including congestive heart failure, coronary restenosis, myocardial infarction, myocardial dysfunction (e.g., related to sepsis), and coronary artery bypass graft; cancer, such as multiple myeloma and myelogenous (e.g., AML and CML) and other leukemias, as well as tumor metastasis; diabetes (e.g., insulin diabetes); endometriosis; fever; fibromyalgia; glomerulonephritis; graft versus host disease/transplant rejection; hemohorragic shock; hyperalgesia; inflammatory bowel disease; inflammatory conditions of a joint, including osteoarthritis, psoriatic arthritis and rheumatoid arthritis; inflammatory eye disease, as may be associated with, for example, corneal transplant; ischemia, including cerebral ischemia (e.g., brain injury as a result of trauma, epilepsy, hemorrhage or stroke, each of which may lead to neurodegeneration); Kawasaki's disease; learning impairment; lung diseases (e.g., ARDS); multiple sclerosis; myopathies (e.g., muscle protein metabolism, esp. in sepsis); neurotoxicity (e.g., as induced by HIV); osteoporosis; pain, including cancer-related pain; Parkinson's disease; periodontal disease; pre-term labor; psoriasis; reperfusion injury; septic shock; side effects from radiation therapy; temporal mandibular joint disease; sleep disturbance; uveitis; or an inflammatory condition resulting from strain, sprain, cartilage damage, trauma, orthopedic surgery, infection or other disease processes.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., 1989, MOLECULAR CLONING: A LABORATORY MANUAL, 2d ed., Cold Spring Harbor Laboratory Press, Cold Spring Harbor, N.Y., which is incorporated herein by reference for any purpose. Unless specific definitions are provided, the nomenclatures utilized in connection with, and the laboratory procedures and techniques of, analytical chemistry, synthetic organic chemistry, X-ray crystallography and medicinal and pharmaceutical chemistry described herein are those well known and commonly used in the art. Standard techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "polypeptide" is used herein as a generic term to refer to native proteins, or sequences that have deletions, additions, and/or substitutions of one or more amino acids of the native sequence. The term "polypeptide" also encompasses a modified IL-1 type 1 receptor, or sequences that have deletions, additions, and/or substitutions of one or more amino acid of a modified IL-1 type 1 receptor.

The term "operably linked" as used herein refers to components that are in a relationship permitting them to function in their intended manner. For example, a control sequence "operably linked" to a coding sequence is ligated in such a way that expression of the coding sequence is achieved under conditions compatible with the control sequences.

The term "control sequence" as used herein refers to polynucleotide sequences, which may effect the expression and processing of coding sequences to which they are ligated. The nature of such control sequences may differ depending upon the host organism. According to certain embodiments, control sequences for prokaryotes may include promoter, ribosomal binding site, and transcription termination sequence. According to certain embodiments, control sequences for eukaryotes may include promoters and transcription termination sequence. In certain embodiments, "control sequences" can include leader sequences and/or fusion partner sequences.

The term "polynucleotide" as referred to herein means a polymeric form of nucleotides of at least 10 bases in length. In certain embodiments, the bases may be ribonucleotides or deoxyribonucleotides or a modified form of either type of nucleotide. The term includes single and double stranded forms of DNA.

The term "oligonucleotide" referred to herein includes naturally occurring, and modified nucleotides linked together by naturally occurring, and/or non-naturally occurring oligonucleotide linkages. Oligonucleotides are a polynucleotide subset generally comprising a length of 200 bases or fewer. In certain embodiments, oligonucleotides are 10 to 60 bases in length. In certain embodiments, oligonucleotides are 12, 13, 14, 15, 16, 17, 18, 19, or 20 to 40 bases in length. Oligonucleotides may be single stranded or double stranded, e.g. for use in the construction of a gene mutant. Oligonucleotides of the invention may be sense or antisense oligonucleotides.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res*. 14:9081; Stec et al., 1984, *J. Am. Chem. Soc*. 106:6077; Stein et al., 1988, *Nucl. Acids Res*. 16:3209; Zon et al., 1991, *Anti-Cancer Drug Design* 6:539; Zon et al., 1991, OLIGONUCLEOTIDES AND ANALOGUES: A PRACTICAL APPROACH, pp. 87–108 (F. Eckstein, Ed.), Oxford University Press, Oxford England; Stec et al., U.S. Pat. No. 5,151,510; Uhlmann and Peyman, 1990, *Chemical Reviews* 90:543, the disclosures of which are hereby incorporated by reference for any purpose. An oligonucleotide can include a label for detection.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell. A cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 1989, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is stably transformed when the DNA is replicated with the division of the cell.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness, which includes both identical matches and conservative substitution matches. If two polypeptide sequences have, for example, 10/20 identical amino acids, and the remaining ones are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Identity and similarity of related polypeptides can be readily calculated by known methods. Such methods include, but are not limited to, those described in COMPUTATIONAL MOLECULAR BIOLOGY, (Lesk, A. M., ed.), 1988, Oxford University Press, New York; BIOCOMPUTING: INFORMATICS AND GENOME PROJECTS, (Smith, D. W., ed.), 1993, Academic Press, New York; COMPUTER ANALYSIS OF SEQUENCE DATA, Part 1, (Griffin, A. M., and Griffin, H. G., eds.), 1994, Humana Press, New Jersey; von Heinje, G., SEQUENCE ANALYSIS IN MOLECULAR BIOLOGY, 1987, Academic Press; SEQUENCE ANALYSIS PRIMER, (Gribskov, M. and Devereux, J., eds.), 1991, M. Stockton Press, New York; and Carillo et al., 1988, *SIAM J. Applied Math.*, 48:1073.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., 1984, *Nucl. Acid. Res.*, 12:387; Genetics Computer Group, University of Wisconsin, Madison, Wis., BLASTP, BLASTN, and FASTA, Altschul et al., 1990, *J. Mol. Biol.*, 215:403–410). The BLASTX program is publicly available from the National Center for Biotechnology Information (NCBI) and other sources (BLAST Manual, Altschul et al. NCB/NLM/NIH Bethesda, Md. 20894; Altschul et al., 1990, supra). The well-known Smith Waterman algorithm may also be used to determine identity.

Certain alignment schemes for aligning two amino acid sequences may result in the matching of only a short region of the two sequences, and this small, aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

The term "polypeptide fragment" as used herein refers to a polypeptide that has an amino-terminal and/or carboxy-terminal deletion. The term "ligand-binding fragment" as used herein refers to a polypeptide that has an amino-terminal and/or carboxy-terminal deletion and retains the ability to form a complex with certain ligands.

Peptide analogs are commonly used in the pharmaceutical industry as non-peptide drugs with properties analogous to those of the template peptide. These types of non-peptide compound are termed "peptide mimetics" or "peptidomimetics". Fauchere, J. 1986, *Adv. Drug Res.*, 15:29; Veber and Freidinger, 1985, TINS p.392; and Evans et al., 1987, *J. Med. Chem.* 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2NH$—, —$CH_2S$—, —$CH_2$—$CH_2$—, —CH=CH—(cis and trans), —$COCH_2$—, —CH(OH) $CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo and Gierasch, 1992, *Ann. Rev. Biochem.*, 61:387, incorporated herein by reference for any purpose); for example, by adding internal cysteine residues capable of forming intramolecular disulfide bridges which cyclize the peptide.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatitc fluid.

The term "pharmaceutical agent or drug" as used herein refers to a chemical compound or composition capable of inducing a desired therapeutic effect when properly administered to a patient.

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (contaminant species cannot be detected in the composition by conventional detection methods) wherein the composition consists essentially of a single macromolecular species.

The term "patient" includes human and animal subjects.

As used herein, the term "small molecule" refers to a molecule that has a molecular weight of less then about 1500 g/mol. A small molecule can be, for example, small organic molecules, peptides or peptide-like molecules. A "standard small molecule inhibitor" as used herein refers to any small molecule inhibitor of IL-1 activity that is known in the art, for example, 389_11a. As used herein, "crystal" refers to a polypeptide in crystalline form. The term "crystal" includes native crystals and co-crystals, as described herein.

The term "native crystal" refers to a crystal wherein the polypeptide is substantially pure.

As used herein, "co-crystal" refers to a crystal wherein the polypeptide is in association with one or more compounds. Such compounds include, by way of example and not limitation, cofactors, substrates, substrate analogues, inhibitors, allosteric effectors, etc.

The term "unit cell" as used herein refers to the smallest and simplest volume element (i.e., parallelpiped-shaped block) of a crystal that is completely representative of the unit of pattern of the crystal. Six numbers define the dimensions of a unit cell: dimensions a, b and c and angles α, β, and γ. (Blundel et al., Protein Crystallography, 1976, Academic Press). A crystal is an efficiently packed array of many unit cells.

As used herein, "space group" refers to the symmetry of a unit cell. In a space group designation (e.g., C2) the capital letter indicates the lattice type and the other symbols represent symmetry operations that can be carried out on the unit cell without changing its appearance.

As used herein, "molecular replacement" refers to the method of calculating initial phases for a new crystal whose structure coordinates are unknown by orienting and positioning a molecule whose structure coordinates are known within the unit cell of the new crystal so as to best account for the observed diffraction pattern of the new crystal. Phases are then calculated from this model and combined with observed amplitudes to provide an approximate Fourier synthesis of the structure of the molecules comprising the new crystal. This, in turn, is subject to any of several methods of refinement to provide a final, accurate set of structure coordinates for the new crystal (Lattman, 1985, *Methods in Enzymology* 115:55–77; Rossmann, 1972, "The Molecular Replacement Method," Int. Sci. Rev. Ser. No. 13, Gordon & Breach, 1972, New York).

Unless otherwise required by context, singular terms shall include pluralities and plural terms shall include the singular.

Expression of a Modified IL-1 Type 1 Receptor (IL1R2D)

A modified IL-1 type 1 receptor has been described in Vigers et al., 2000, *J. Biol. Chem.* 275:36927–36933. The modified IL-1 type 1 receptor described by Vigers et al. is herein referred to as IL1R2D. As used herein, "modified IL-1 type 1 receptor" and "IL1R2D" may be used interchangeably. IL1R2D comprises two immunoglobulin-like binding domains of full length IL-1R1 (SEQ ID NO: 1) and comprises amino acids 18 to 222 of SEQ ID NO: 1 (SEQ ID NO: 2).

IL1R2D binds with high affinity to IL-1 receptor antagonist (IL-1ra), binding with a $K_d$ of greater than or equal to 1 μM. However, IL1R2D does not bind with high affinity to IL-1, binding with a $K_d$ of less than or equal to 10 μM.

In certain embodiments, conservative modifications can produce a modified IL-1 type 1 receptor having functional and chemical characteristics similar to those of full length IL-1R1 (SEQ ID NO: 1). For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis." Desired amino acid substitutions (whether conservative or non-conservative) can be determined by those skilled in the art at the time such substitutions are desired.

Substantial modifications in the functional and/or chemical characteristics of IL1R2D can be accomplished by selecting substitutions in the amino acid sequence of the IL-1 type 1 receptor that provide, for example, the ability to crystallize the receptor complex in different space groups or a reduced overall mass of the complex.

In certain embodiments, a nucleic acid molecule encoding the amino acid sequence of a modified IL-1 type 1 receptor of the invention, such as IL1R2D, can be inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a modified IL-1 type 1 receptor polypeptide, such as IL1R2D, may be amplified/expressed in prokaryotic, yeast, insect (such as baculovirus systems) and/or eukaryotic host cells. For a review of expression vectors, see METH. ENZ., vol. 185 (D. V. Goeddel, ed.), 1990, Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the modified IL-1R1 polypeptide coding sequence; the oligonucleotide sequence can encode, for example, polyhis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of modified IL-1 type 1 receptor from the host cell. Affinity purification can be accomplished, for example, by column chromatography using antibodies against the tag as an affinity matrix. Optionally, the tag can subsequently be removed from the purified IL-1R1 polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, QIAGEN® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide-coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a modified IL-1 type 1 receptor polypeptide. As a result, increased quantities of the modified IL-1 type 1 receptor polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

The expression and cloning vectors of the present invention will typically contain a promoter that is recognized by the host organism and operably linked to the molecule encoding the modified IL-1 type 1 receptor. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding the modified IL-1 type 1 receptor by removing the promoter from the source DNA by restriction enzyme digestion and inserting the desired promoter sequence into the vector.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: the SV40 early promoter region (Bemoist and Chambon, 1981, *Nature* 290:304–10); the CMV promoter; the promoter contained in the 3' long terminal repeat of Rous sarcoma virus (Yamamoto, et al., 1980, *Cell* 22:787–97); the herpes thymidine kinase promoter (Wagner et al., 1981, *Proc. Natl. Acad. Sci. U.S.A.* 78:1444–45); the regulatory sequences of the metallothionine gene (Brinster et al., 1982, *Nature* 296:39–42); prokaryotic expression vectors such as the beta-lactamase promoter (Villa-Kamaroff et al., 1978, *Proc. Natl. Acad. Sci. U.S.A.* 75:3727–31); or the tac promoter (DeBoer et al., 1983, *Proc. Natl. Acad. Sci. U.S.A.* 80:21–25). Also of interest are the following animal transcriptional control regions, which exhibit tissue specificity and have been utilized in transgenic animals: the elastase I gene control region which is active in pancreatic acinar cells (Swift et al., 1984, *Cell* 38:639–46; Ornitz et al., 1986, *Cold Spring Harbor Symp. Quant. Biol.* 50:399–409 (1986); MacDonald, 1987, *Hepatology* 7:425–515); the insulin gene control region which is active in pancreatic beta cells (Hanahan, 1985, *Nature* 315:115–22); the immunoglobulin gene control region which is active in lymphoid cells (Grosschedl et al., 1984, *Cell* 38:647–58; Adames et al., 1985, *Nature* 318:533–38; Alexander et al., 1987, *Mol. Cell. Biol.* 7:1436–44); the mouse mammary tumor virus control region which is active in testicular, breast, lymphoid and mast cells (Leder et al., 1986, *Cell*, 45:485–95); the albumin gene control region which is active in liver (Pinkert et al., 1987, *Genes and Devel.* 1:268–76); the alpha-feto-protein gene control region which is active in liver (Krumlauf et al., 1985, *Mol. Cell. Biol.* 5:1639–48; Hammer et al., 1987, *Science* 235:53–58); the alpha 1-antitrypsin gene control region which is active in the liver (Kelsey et al., 1987, *Genes and Devel.* 1:161–71); the beta-globin gene control region which is active in myeloid cells (Mogram et al., 1985, *Nature* 315:338–40; Kollias et al., 1986, *Cell* 46:89–94); the myelin basic protein gene control region which is active in oligodendrocyte cells in the brain (Readhead et al., 1987, *Cell* 48:703–12); the myosin light chain-2 gene control region which is active in skeletal muscle (Sani, 1985, *Nature* 314:283–86); and the gonadotropic releasing hormone gene control region which is active in the hypothalamus (Mason et al., 1986, *Science* 234:1372–78).

An enhancer sequence may be inserted into the vector to increase the transcription of a DNA encoding a modified IL-1 type 1 receptor of the present invention by higher eukaryotes. Enhancers are cis-acting elements of DNA, usually about 10–300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding a modified IL-1 type 1 receptor has been inserted into the proper site of the vector, the completed vector may be inserted into a suitable host cell for amplification and/or polypeptide expression. The transformation of an expression vector for a modified IL-1 type 1 receptor into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cells). The host cell, when cultured under appropriate conditions, synthesizes a modified IL-1 type 1 receptor that can subsequently be collected from the culture medium (if the host cell secretes it into the medium) or directly from the host cell producing it (if it is not secreted). The selection of an appropriate host cell will depend upon various factors, such as desired expression levels and polypeptide modifications that are desirable or necessary for activity and ease of folding into a biologically active molecule.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

A modified IL-1 type 1 receptor, such as IL1R2D, can be incubated with one or more potential binding partners to form an IL-1 receptor type 1 protein-ligand complex. In certain embodiments, the complex can be crystallized in a form suitable for X-ray crystallography and the three-dimensional structure can be determined.

Crystallization of IL1R2D-ligand Complexes

In one embodiment, the invention provides crystals of a modified IL-1R1 protein-ligand complex. Crystals comprising two copies of the small-molecule 389_11a and IL1R2D were obtained by the methods provided in the Examples. The crystalline forms of the IL1R2D:389_11a complex were space group R3 and have unit cell dimensions of a=96.3 Å, b=96.3 Å, c 75.3 Å and α=90°, β=90°, and γ=120°.

Crystals of the invention can be grown using conventional techniques well-known in the art of protein crystallography, including batch crystallization, liquid bridge, dialysis, vapor diffusion and hanging drop methods (see, e.g., McPherson, Preparation and Analysis of Protein Crystals, 1982, John Wiley, New York; McPherson, 1990, *Eur. J. Biochem.* 189: 1–23; Weber, 1991, *Adv. Protein Chem.* 41:1–36).

Generally, the crystals of the invention can be grown by incubating substantially pure IL1R2D polypeptide with potential small molecule inhibitors allowing a complex to form. The complex can be dissolved in an aqueous buffer containing a precipitant at a concentration just below that necessary to precipitate the protein-ligand complex. Controlled evaporation can be used to remove water, generating precipitating conditions. Precipitating conditions are maintained until crystal growth is completed.

In a preferred embodiment of the invention, crystals are grown by vapor diffusion in hanging drops as described, for example, in McPherson, Preparation and Analysis of Protein Crystals, 1982, John Wiley, New York and McPherson, 1990, *Eur. J. Biochem.* 189:1–23; Weber, 1991, *Adv. Protein Chem.* 41:1–36. The polypeptide/precipitant solution is allowed to equilibrate in a closed container with a large aqueous reservoir. Preferably, the precipitant concentration is optimal for producing crystals. Generally, 2–5 μL of substantially pure polypeptide-ligand complex solution is mixed with an equal volume of precipitant solution. The final concentration of the precipitant is about half that necessary for crystallization. The solution is then suspended as a droplet on the bottom surface of a coverslip. The coverslip is sealed onto the top of the reservoir. A sealed container is allowed to stand until crystals have finished growing, typically in about 1 day to 6 weeks. For example, hanging drops containing about 3.8 μL of IL1R2D polypeptide-389_11a complex (7.2 mg/mL in 20 mM HEPES pH 7.5, 130 mM NaCl and 0.25% Chaps) and 3.8 μL precipitant solution (30% polyethylene glycol (PEG) 4K, 100 mM Sodium Citrate pH 5.7) were suspended over 1 mL reservoir buffer for about 2 days at 4° C. and provided crystals suitable for high resolution X-ray structure determination.

Those of skill in the art will recognize that the above-described crystallization conditions can be varied. Variations can be used alone or in combination, and include, for example, polypeptide solutions containing polypeptide-ligand complex concentrations between about 0.1 mg/mL and about 100 mg/mL, buffer concentrations between about 5 mM and about 200 mM, pH ranges between about 4.0 and about 9.0 and reservoir solutions containing polyethylene glycol concentrations between about 5% and about 40% (w/v), polyethylene glycol molecular weights between about 200 and about 10,000, Ammonium sulfate, sodium potassium phosphate or sodium citrate concentrations between about 0.05M and about 2.0M, ethylene glycol or glycerol concentrations between about 5% and about 40% (v/v), methane pentane diol or isopropanol concentrations between about 5% and about 50%, and temperature ranges between about 0° C. and about 25° C. Other buffer solutions can be used such as sodium acetate, MES, PIPES or TRIS buffer, so long as the desired pH range is maintained. Additional agents, such as NaCl or $MgCl_2$ from about 0.1 to 1.0M, or a variety of detergents above or below their CMC, can also be added.

A crystal of the invention can be characterized by any of a number of known methods using X-rays to determine atomic coordinates of the crystalline form. The X-rays can be produced in a conventional source (such as a sealed tube or a rotating anode) or using a synchrotron source. Methods of characterization include, but are not limited to, precision photography, oscillation photography, and diffractometer data collection. Methods of X-ray detection include, but are not limited to, photographic film, hot-wire detectors, image plates and CCD cameras. Methods for data reduction and structure determination are embodied in a wide variety of computer programs, including but not limited to, Denzo/Scalepack, CCP4 and X-Plor/CNX. Methods for obtaining the three-dimensional structure of a crystal, as well as atomic structure coordinates, are well known in the art (see, e.g., Ducruix and Giege, 1992, Crystallization of Nucleic Acids and Proteins: A Practical Approach, IRL Press, Oxford, England and McRee, Practical Protein Crystallography, 1993, Academic Press, and references cited therein).

Crystalline Forms of a Modified IL-1R1 Protein-ligand Complex

In one embodiment, crystals of the invention comprise substantially pure IL1R2D polypeptide and at least one small molecule inhibitor in crystalline form. In certain embodiments, however, crystals of the invention can comprise mutants of IL1R2D.

Mutants of IL1R2D can be obtained by substitution of at least one amino acid residue with a different amino acid residue. Mutants can also be obtained by addition or deletion of amino acid residues within the IL1R2D polypeptide or at the N- or C-terminus of the IL1R2D polypeptide. In a preferred embodiment, crystals comprising mutants of IL1R2D have substantially the same three-dimensional structure as crystals comprising the native IL1R2D from which the mutant is derived.

The term "substantially the same three-dimensional structure" refers to having a set of atomic structure coordinates where the non-hydrogen atoms in each domain of the protein have a root mean square deviation of less than or equal to about 4.0 A when superimposed with the atomic structure coordinates of crystals comprising the native IL1R2D from which the mutant is derived.

Amino acid substitutions, deletions and additions that do not significantly interfere with the three-dimensional structure of a crystal comprising native IL1R2D will depend, in part, on the region of the IL1R2D polypeptide where the substitution, addition or deletion occurs. Such mutations are likely to be well tolerated, for example, at surface residues on portions of the IL1R2D distal to the Site-A ligand binding area, or in interior regions of the IL1R2D as long as the packing contacts are not disrupted.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, areas that may be important for biological activity or for structure may be subject to conservative amino acid substitutions without destroying the biological activity or without adversely affecting the polypeptide structure.

Suitable polypeptide variants also include glycosylation variants wherein the number and/or type of glycosylation sites have been altered compared to amino acids 18 to 222 of SEQ ID NO: 1 (SEQ ID NO: 2). In one embodiment, IL1R2D polypeptide variants comprise a greater or a lesser number of N-linked glycosylation sites than amino acids 18 to 222 of SEQ ID NO: 1 (SEQ ID NO: 2). An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

As used herein, the twenty conventional amino acids and their abbreviations follow conventional usage. See IMMUNOLOGY—A SYNTHESIS, 2nd Edition, (E. S. Golub and D. R. Gren, Eds.), 1991, Sinauer Associates, Sunderland, Mass., which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues may be divided into classes based on common side chain properties:
1) hydrophobic: Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, *J. Mol. Biol.* 157:105–131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included.

Exemplary amino acid substitutions are set forth in Table 1.

TABLE 1

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in PROTEINS, STRUCTURES AND MOLECULAR PRINCIPLES (Creighton, Ed.), 1984, W. H. Freeman and Company, New York; INTRODUCTION TO PROTEIN STRUCTURE (C. Branden and J. Tooze, eds.), 1991, Garland Publishing, New York, N.Y.; and Thornton et at., 1991, *Nature* 354:105, which are each incorporated herein by reference.

Uses for Crystals of IL1R2D Complexes

In certain embodiments, a crystal of the invention can be used to identify ligands and drugs useful for treating IL-1 mediated diseases using structure-based drug design. After the three dimensional structure of a crystal of the invention is determined, a potential ligand or drug can be examined by computer modeling. For example, computer fitting of potential ligands or drugs to a ligand-binding site can predict how well the shape and chemical structure of the potential ligand or drug will complement the binding site. (See for example, Bugg et al., 1993, *Scientific American* December:92–98; West et al., 1995, *TIPS* 16:67–74). Computer programs can also estimate the attraction, repulsion, and steric hindrance of the ligand-binding site and the potential ligand or drug. Such information provides the ability to design a potent drug with minimal potential side effects. For example, the lower the steric hindrances and the greater the attractive forces, the more likely the drug will interact only with its target. Higher specificity for the target may minimize potential side effects caused by interaction with other proteins.

Potential ligands can also be selected based on their structural similarity to known ligands that bind IL-1 type 1 receptor. A promising potential modulator can be identified by systematically modifying the structural analog using computer modeling programs. For example, such analysis has been described for developing HIV protease inhibitors (Lam et al., 1994, *Science* 263:380–384; Wlodawer et al., 1993, *Ann. Rev. Biochem.* 62:543–585; Appelt, 1993, *Perspectives in Drug Discovery and Design* 1:23–48; Erickson, 1993, *Perspectives in Drug Discovery and Design* 1:109–128). In addition, potential ligands can be selected after screening a random peptide library as described in Scott and Smith, 1990, *Science* 249:386–390, Cwirla et al., 1990, *Proc. Natl. Acad. Sci. U.S.A.* 87:6378–6382, and Devlin et al., 1990, *Science* 249:404–406.

After a potential ligand is identified, the ligand can be obtained from a commercial library of chemicals or synthesized de novo. Appropriate methods of chemical synthesis include medicinal chemistry and combinatorial chemistry techniques know to those of skill in the art (see, for example, Advanced Organic Chemistry $2^{nd}$ edition (J. March) 1977, McGraw-Hill New York and B. A. Bunin, The Combinatorial Index, 1998, Academic Press). The potential ligand can be screened for binding activity in one of many standard binding assays, such as, for example, a radioligand receptor binding assay on a solid support, or a fluorescence-polarization assay conducted in solution (See for example, Immune and Receptor Assays in Theory and in Practice, Patrick Englebienne, CRC Press 2000).

A ligand that binds the IL-1 type 1 receptor can be further examined for the ability to inhibit IL-1 activity using cell-based assays to measure cell-surface receptor binding or modulation of downstream responses, such as TNF production or cell death, in a variety of readily available cell types such as EL4 cells (see, for example, Dripps et al., 1991, *J. Biol. Chem.* 16:10331–10336). Additional studies can be carried out in animal model systems of inflammatory conditions that may or may not mimic disease states of therapeutic interest.

A ligand or potential drug can be selected based on its ability to modulate IL-1 activity or its ability to bind IL-1 type 1 receptor or a ligand binding fragment thereof. Once a ligand or potential drug has been selected it can be used to grow a supplemental crystal comprising the ligand or potential drug and a modified IL-1 type 1 receptor. The supplemental crystal comprising a protein-ligand complex formed between a modified IL-1 type 1 receptor and the ligand or potential drug can be used to identify more ligands or potential drugs. Preferably, the supplemental crystal effectively diffracts X-rays for the determination of the atomic coordinates of the protein-ligand complex to a resolution of greater than 3.5 Angstroms. The three-dimensional structure of the supplemental crystal can be determined with molecular replacement analysis.

Molecular replacement analysis involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal using computer programs such as X-PLOR (Brunger et al., 1987, *Science* 235:458–460) and AMORE (Navaza, 1994, *Acta Crystallographics ASO* 157–163). Once the position and orientation are known an electron density map can be calculated using the search model to provide X-ray phases. The electron density is inspected for structural differences and the search model is modified to conform to the new structure. Other computer programs can be used to solve the structures, including, for example, INSIGHT, SYBYL, MACROMODEL, and ICM.

In another embodiment of the invention, a candidate compound can be selected by performing a structure-based drug design with the three-dimensional structure determined for the supplemental crystal in conjunction with computer modeling. The candidate compound is contacted with a cell that expresses IL-1 and IL-1R1. The candidate compound can be assayed for its ability to affect IL-1 binding to IL-1 type 1 receptor, or for its ability to interfere with IL-1 activity in the cell. The cell can be isolated from an animal or can be in a living animal. Preferably, the cell is an isolated cell, such as a transformed cultured cell. Cell lines useful for assaying IL-1 activity include, but are not limited to, EL4 cells, 3T3 cells and transiently transfected COS cells.

Pharmaceutical Compositions and Therapeutic Uses Thereof

In certain embodiments, ligands identified by the methods of the invention can modulate IL-1 activity. In a particular embodiment, modulators of the invention can inhibit IL-1 signaling by binding to IL-1R1 and can be useful in treatment of IL-1 mediated diseases. In other embodiments, a modulator of the invention can act as an antagonist or agonist of IL-1 activity.

The invention also provides pharmaceutical compositions comprising a therapeutically effective amount of a modulator or modulators of the invention together with a pharmaceutically acceptable diluent, carrier, solubilizer, emulsifier, preservative and/or adjuvant.

In certain embodiments, acceptable formulation materials preferably are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents;

surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. REMINGTON'S PHARMACEUTICAL SCIENCES, 18$^{th}$ Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the modulators of the invention.

In certain embodiments, the primary vehicle or carrier in a pharmaceutical composition may be either aqueous or non-aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of about pH 7.0–8.5, or acetate buffer of about pH 4.0–5.5, which may further include sorbitol or a suitable substitute therefor. In certain embodiments of the present invention, compositions of the invention may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the product may be formulated as a lyophilizate using appropriate excipients such as sucrose.

In certain embodiments, the pharmaceutical compositions of the invention can be selected for parenteral delivery. In certain embodiments, the compositions may be selected for inhalation or for delivery through the digestive tract, such as orally. The preparation of such pharmaceutically acceptable compositions is within the skill of the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, the therapeutic compositions for use in this invention may be in the form of a pyrogen-free, parenterally acceptable aqueous solution comprising the desired modulator of the invention in a pharmaceutically acceptable vehicle. In certain embodiments, a particularly suitable vehicle for parenteral injection is sterile distilled water in which the modulator is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, a modulator of the invention may be formulated as a dry powder for inhalation. In certain embodiments, inhalation solutions may also be formulated with a propellant for aerosol delivery. In certain embodiments, solutions may be nebulized. Pulmonary administration is further described in PCT application no. PCT/US94/001875, which describes pulmonary delivery of chemically modified proteins.

In certain embodiments, it is contemplated that formulations may be administered orally. In certain embodiments of the present invention, modulators of the invention administered in this fashion may be formulated with or without those carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, additional agents can be included to facilitate absorption of a modulator of the invention. In certain embodiments, diluents, flavorings, low melting point waxes, vegetable oils, lubricants, suspending agents, tablet disintegrating agents, and binders may also be employed.

In certain embodiments, a pharmaceutical composition may involve an effective quantity of a modulator of the invention in a mixture with non-toxic excipients, which are suitable for the manufacture of tablets. In certain embodiments, by dissolving the tablets in sterile water, or another appropriate vehicle, solutions may be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a modulator of the invention in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See, for example, PCT Application No. PCT/US93/00829, which describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices may include polyesters, hydrogels, polylactides (U.S. Pat. No. 3,773,919 and EP 058,481), copolymers of L-glutamic acid and gamma ethyl-L-glutamate (Sidman et al., 1983, *Biopolymers*, 22:547–556), poly (2-hydroxyethyl-methacrylate) (Langer et al., 1981, *J. Biomed. Mater. Res.*, 15:167–277; Langer, 1982, *Chem. Tech.*, 12:98–105), ethylene vinyl acetate (Langer et al., supra) or poly-D(−)-3-hydroxybutyric acid (EP 133,988). In certain embodiments, sustained release compositions may also include liposomes, which can be prepared by any of several methods known in the art. See e.g., Eppstein et al., 1985, *Proc. Natl. Acad. Sci. USA*, 82:3688–3692; EP 036,676; EP 088,046 and EP 143, 949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., lyophilized) that is reconstituted prior to administration.

In certain embodiments, the present invention is directed to kits for producing a single-dose administration unit. In certain embodiments, the kits may each contain both a first container having a dried protein and a second container having an aqueous formulation. In certain embodiments of this invention, kits containing single and multi-chambered pre-filled syringes (e.g., liquid syringes and lyosyringes) are included.

In certain embodiments, the effective amount of a pharmaceutical composition of the invention to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the modulator of the invention is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

In certain embodiments, the frequency of dosing will depend upon the pharmacokinetic parameters of a modulator of the invention in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages may be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use pharmaceutical compositions of the invention in an ex vivo manner. In such instances, cells, tissues or organs that have been removed from the patient are exposed to pharmaceutical compositions of the invention after which the cells, tissues and/or organs are subsequently implanted back into the patient.

In certain embodiments, a modulator of the invention can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

The following examples, including the experiments conducted and results achieved are provided for illustrative purposes only and are not to be construed as limiting the present invention.

Example 1

Expression and Purification of IL1R2D

The amino acid sequence as set forth in SEQ ID NO: 1 corresponds to the full length IL-1 type 1 receptor (FIG. 2). A modified IL-1 type 1 receptor was made that encodes the human IL-1R1 protein from the initiating methionine in the secretion peptide through the lysine 222 (IL 1R2D), and was cloned into a baculovirus transfer vector. Sf9 cells were co-transfected with the resulting transfer vector DNA and Baculogold DNA using the calcium phosphate precipitation technique. Protocol, reagents and baculovirus originated from Pharmingen, a Becton Dikinson company. Hi5 cells were infected with the recombinant baculovirus using methods as described in O'Reilly, Miller, and Luckow, Baculovirus Expression Vectors: A Laboratory Manual, 1992, W.H. Freeman and Company, N.Y. City. Cells were grown in Ultimate Insect Serum-free medium (Invitrogen, Carlsbad, Calif.) at 28° C. in shake flasks. The protein was secreted into the medium and harvested 48 to 72 hours after infection. The cell culture was centrifuged and the supernatant was collected. The supernatant was mixed with an interleukin-1 receptor antagonist (IL-1ra) covalently bound affinity resin prepared using Affigel-15 from BioRad (Hercules, Calif.) and incubated at 40° C. overnight.

The resin was poured into a chromatography column, washed with phosphate buffered saline (PBS) plus 0.5 M NaCl and eluted with 2 column volumes 0.1 M acetic acid pH 2.8, 0.2 M NaCl, 10% glycerol, and 0.25% 3-[(3-cholamidopropyl)dimethylammonio]-1-propanesulfonic acid (CHAPS). The fractions were immediately neutralized using 0.1 fraction volume of 1 M Tris pH 9.5. Fractions containing IL1R2D were identified by electrophoretic mobility using standard SDS-PAGE methods.

Fractions identified by SDS-PAGE as containing IL1R2D were pooled and concentrated to 5 ml. The concentrated fractions were loaded onto a Superdex 200 column (Pharmacia) pre-equilibrated and run in 20 mM HEPES, pH 7.0, 100 mM NaCl, and 0.25% CHAPS. Monomer containing fractions were identified by standard SDS-PAGE methods. These fractions were pooled, concentrated, and stored at −70° C.

Example 2

Co-Crystallization of 389_11a:IL1R2D and Solution of the X-Ray Structure

389_11a was synthesized by standard solid-phase peptide synthesis methods as described in WO 96/29088. The IL1R2D at a concentration of 7.2 mg/ml was incubated with 2 mM 389_11a in 2% DMSO for two hours on ice. Crystals were prepared by the hanging drop method (See, for example, Protein Crystallization: Techniques, Strategies and Tips, A Laboratory Manual, (T. M. Bergfors, Ed.), 1999, International University Line). Briefly, drops were prepared by mixing 3 μL of protein solution with the same volume of precipitant solution (30% PEG4K and 100 mM Na Citrate, pH 5.7) on a siliconized glass cover slip. The cover slip was placed over a small well containing 1 mL of precipitant solution. Crystals were grown at 4° C. in about five days.

The crystals were transferred to a cryoprotectant solution (10% Ethylene Glycol plus 90% Mother Liquor) for 2 minutes, and mounted on a goniometer, which was cooled with Nitrogen gas to 100K. Three data sets were collected using a Rigaku H3R generator, Osmic confocal optics and Raxis IV image plate detector (Table 2). Data were processed using Denzo and Scalepack (Otwinowski, in *Data Collection and Processing*, (Sawyer, Isaacs, and Bailey Eds.), 1993, Science and Engineering Research Council, Daresbury Laboratory, Warrington, UK). All crystals were space group R3, unit cell a=96.3 Å, b=96.3 Å, c=75.3 Å, α=90.0° C., β=90.0° C., and γ=120° C.

TABLE 2

| Data collection statistics for 389_11a:IL1R2D | | | |
|---|---|---|---|
| Data Set | 20010816L | 20010828L | 20010904R |
| Resolution (A) | 2.8 | 3.4 | 2.9 |
| Completeness (%) | 91.3 | 82.5 | 91 |
| Completeness in last shell (%) | 66.8 | 59.4 | 65.9 |
| Number of unique observations | 6064 | 3536 | 5641 |
| Total observations | 24674 | 24674 | 51236 |

The structure was solved by molecular replacement using MOLREP® in the CCP4 suite (CCP4: Collaborative Computational Project No 4, Daresbury UK, 1994, *Acta Crystallogr. D* 50:760) from the previous AF10847:IL1R1 structure and refined with X-plor (Brunger et al., 1987, *Science* 235:458–460). The small molecule was modeled in Sybyl and O (Jones et al., 1991, *Acta Crystallogr. A* 47:110–119), and potentials were assigned using Array custom software. The final Rfactor was 26.4% (Rfree=36.4%). All three data sets gave similar results. The coordinates for data set 20010816L are given in Table 3. Residues C23 to E220 of SEQ ID NO: 1 could be resolved in the electron density map, and in the Table are numbered as C6 to E203, corresponding to the numbering of the mature protein. It is assumed that the full sequence of residues 18 to 222 (SEQ ID NO: 2) were present in the crystal, but that the terminal residues could not be resolved due to high mobility or to multiple conformations.

Figure 3:
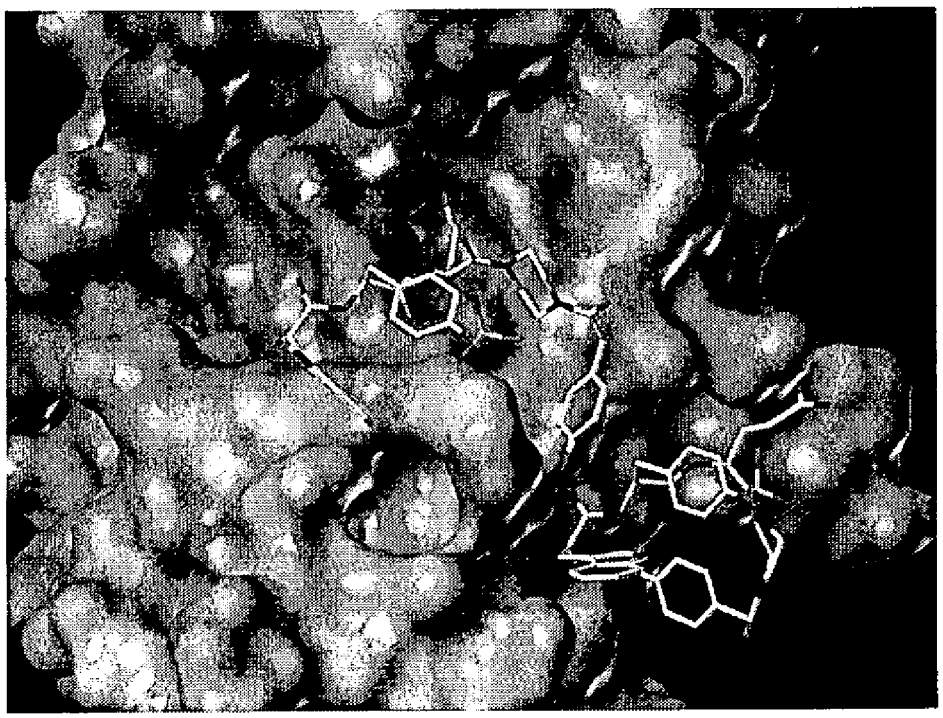
FIG. 3 depicts an electron density map of the IL1R2D: 389__11a complex.
Figure 4:
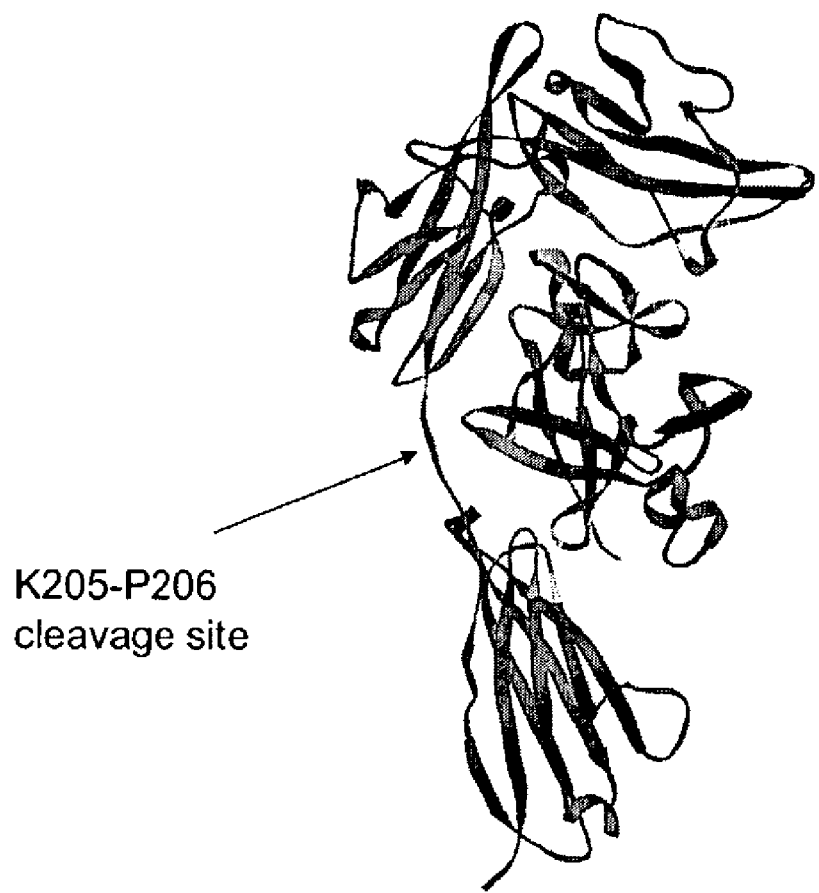
FIG. 4 depicts the location of the C-terminus of the IL1R2D construct. The IL12RD construct is shown in complex with IL-1ra.

An electron density map of the complex was generated in Xplor (FIG. 3). The electron density map revealed that two copies of 389_11a were present in each copy of the IL1R2D. One copy lay at the center of the Site A binding site of the IL1R2D, the other lay on the side of the IL1R2D.

TABLE 3

| Crystallographic coordinates for the refined co-crystal | | | | | | | | |
|---|---|---|---|---|---|---|---|---|
| ATOM | 1 | C | CYS | 6 | 69.690 | 2.451 | 25.595 | 1.00 | 20.62 R1 |
| ATOM | 2 | O | CYS | 6 | 68.531 | 2.756 | 25.286 | 1.00 | 18.94 R1 |
| ATOM | 3 | CB | CYS | 6 | 69.907 | 0.175 | 24.470 | 1.00 | 20.54 R1 |
| ATOM | 4 | SG | CYS | 6 | 71.262 | 0.286 | 23.230 | 1.00 | 22.44 R1 |
| ATOM | 5 | HT1 | CYS | 6 | 69.481 | 0.809 | 27.779 | 1.00 | 35.00 R1 |
| ATOM | 6 | HT2 | CYS | 6 | 69.606 | −0.673 | 26.966 | 1.00 | 35.00 R1 |
| ATOM | 7 | N | CYS | 6 | 69.303 | 0.319 | 26.877 | 1.00 | 14.01 R1 |
| ATOM | 8 | HT3 | CYS | 6 | 68.286 | 0.352 | 26.662 | 1.00 | 35.00 R1 |
| ATOM | 9 | CA | CYS | 6 | 70.087 | 0.969 | 25.785 | 1.00 | 19.50 R1 |
| ATOM | 10 | N | LYS | 7 | 70.651 | 3.361 | 25.795 | 1.00 | 24.08 R1 |
| ATOM | 11 | H | LYS | 7 | 71.541 | 3.044 | 26.054 | 1.00 | 35.00 R1 |
| ATOM | 12 | CA | LYS | 7 | 70.427 | 4.810 | 25.645 | 1.00 | 26.07 R1 |
| ATOM | 13 | CB | LYS | 7 | 71.627 | 5.617 | 26.130 | 1.00 | 29.31 R1 |
| ATOM | 14 | CG | LYS | 7 | 71.948 | 5.421 | 27.606 | 1.00 | 37.02 R1 |
| ATOM | 15 | CD | LYS | 7 | 70.831 | 5.924 | 28.535 | 1.00 | 37.85 R1 |
| ATOM | 16 | CE | LYS | 7 | 70.940 | 5.307 | 29.941 | 1.00 | 39.01 R1 |
| ATOM | 17 | NZ | LYS | 7 | 70.592 | 3.835 | 29.999 | 1.00 | 36.76 R1 |
| ATOM | 18 | HZ1 | LYS | 7 | 70.703 | 3.492 | 30.974 | 1.00 | 35.00 R1 |
| ATOM | 19 | HZ2 | LYS | 7 | 71.229 | 3.304 | 29.370 | 1.00 | 35.00 R1 |
| ATOM | 20 | HZ3 | LYS | 7 | 69.609 | 3.693 | 29.689 | 1.00 | 35.00 R1 |
| ATOM | 21 | C | LYS | 7 | 70.112 | 5.188 | 24.206 | 1.00 | 25.95 R1 |
| ATOM | 22 | O | LYS | 7 | 70.763 | 4.725 | 23.270 | 1.00 | 24.31 R1 |
| ATOM | 23 | N | GLU | 8 | 69.159 | 6.102 | 24.050 | 1.00 | 25.18 R1 |
| ATOM | 24 | H | GLU | 8 | 68.766 | 6.524 | 24.843 | 1.00 | 35.00 R1 |

TABLE 3-continued

Crystallographic coordinates for the refined co-crystal

| ATOM | 25 | CA | GLU | 8 | 68.694 | 6.498 | 22.741 | 1.00 | 20.99 | R1 |
|---|---|---|---|---|---|---|---|---|---|---|
| ATOM | 26 | CB | GLU | 8 | 67.360 | 5.801 | 22.467 | 1.00 | 23.69 | R1 |
| ATOM | 27 | CG | GLU | 8 | 67.439 | 4.279 | 22.452 | 1.00 | 25.15 | R1 |
| ATOM | 28 | CD | GLU | 8 | 66.082 | 3.603 | 22.436 | 1.00 | 27.62 | R1 |
| ATOM | 29 | OE1 | GLU | 8 | 65.057 | 4.311 | 22.220 | 1.00 | 27.60 | R1 |
| ATOM | 30 | OE2 | GLU | 8 | 66.053 | 2.358 | 22.636 | 1.00 | 21.96 | R1 |
| ATOM | 31 | C | GLU | 8 | 68.514 | 7.979 | 22.537 | 1.00 | 20.36 | R1 |
| ATOM | 32 | O | GLU | 8 | 68.316 | 8.722 | 23.477 | 1.00 | 17.78 | R1 |
| ATOM | 33 | N | ARG | 9 | 68.575 | 8.382 | 21.272 | 1.00 | 22.34 | R1 |
| ATOM | 34 | H | ARG | 9 | 68.769 | 7.705 | 20.591 | 1.00 | 35.00 | R1 |
| ATOM | 35 | CA | ARG | 9 | 68.390 | 9.766 | 20.846 | 1.00 | 23.73 | R1 |
| ATOM | 36 | CB | ARG | 9 | 69.619 | 10.624 | 21.162 | 1.00 | 24.57 | R1 |
| ATOM | 37 | CG | ARG | 9 | 70.831 | 10.380 | 20.291 | 1.00 | 28.13 | R1 |
| ATOM | 38 | CD | ARG | 9 | 71.906 | 11.438 | 20.539 | 1.00 | 30.11 | R1 |
| ATOM | 39 | NE | ARG | 9 | 72.685 | 11.155 | 21.739 | 1.00 | 34.42 | R1 |
| ATOM | 40 | HE | ARG | 9 | 72.201 | 11.008 | 22.577 | 1.00 | 35.00 | R1 |
| ATOM | 41 | CZ | ARG | 9 | 74.013 | 11.088 | 21.762 | 1.00 | 36.60 | R1 |
| ATOM | 42 | NH1 | ARG | 9 | 74.701 | 11.304 | 20.645 | 1.00 | 39.09 | R1 |
| ATOM | 43 | HH11 | ARG | 9 | 74.214 | 11.506 | 19.794 | 1.00 | 35.00 | R1 |
| ATOM | 44 | HH12 | ARG | 9 | 75.695 | 11.256 | 20.638 | 1.00 | 35.00 | R1 |
| ATOM | 45 | NH2 | ARG | 9 | 74.641 | 10.696 | 22.866 | 1.00 | 33.54 | R1 |
| ATOM | 46 | HH21 | ARG | 9 | 74.105 | 10.451 | 23.671 | 1.00 | 35.00 | R1 |
| ATOM | 47 | HH22 | ARG | 9 | 75.631 | 10.610 | 22.884 | 1.00 | 35.00 | R1 |
| ATOM | 48 | C | ARG | 9 | 68.101 | 9.737 | 19.342 | 1.00 | 22.04 | R1 |
| ATOM | 49 | O | ARG | 9 | 68.441 | 8.763 | 18.669 | 1.00 | 23.65 | R1 |
| ATOM | 50 | N | GLU | 10 | 67.453 | 10.778 | 18.823 | 1.00 | 19.50 | R1 |
| ATOM | 51 | H | GLU | 10 | 67.210 | 11.529 | 19.401 | 1.00 | 35.00 | R1 |
| ATOM | 52 | CA | GLU | 10 | 67.105 | 10.819 | 17.405 | 1.00 | 16.02 | R1 |
| ATOM | 53 | CB | GLU | 10 | 65.631 | 10.407 | 17.191 | 1.00 | 18.36 | R1 |
| ATOM | 54 | CG | GLU | 10 | 64.565 | 11.384 | 17.688 | 1.00 | 21.58 | R1 |
| ATOM | 55 | CD | GLU | 10 | 63.126 | 10.932 | 17.375 | 1.00 | 24.29 | R1 |
| ATOM | 56 | OE1 | GLU | 10 | 62.579 | 11.354 | 16.318 | 1.00 | 22.55 | R1 |
| ATOM | 57 | OE2 | GLU | 10 | 62.534 | 10.183 | 18.203 | 1.00 | 19.95 | R1 |
| ATOM | 58 | C | GLU | 10 | 67.388 | 12.123 | 16.680 | 1.00 | 12.85 | R1 |
| ATOM | 59 | O | GLU | 10 | 66.763 | 13.125 | 16.957 | 1.00 | 8.16 | R1 |
| ATOM | 60 | N | GLU | 11 | 68.304 | 12.084 | 15.718 | 1.00 | 15.72 | R1 |
| ATOM | 61 | H | GLU | 11 | 68.757 | 11.237 | 15.526 | 1.00 | 35.00 | R1 |
| ATOM | 62 | CA | GLU | 11 | 68.649 | 13.270 | 14.934 | 1.00 | 20.67 | R1 |
| ATOM | 63 | CB | GLU | 11 | 69.853 | 12.978 | 14.029 | 1.00 | 23.50 | R1 |
| ATOM | 64 | CG | GLU | 11 | 70.923 | 14.077 | 14.013 | 1.00 | 25.56 | R1 |
| ATOM | 65 | CD | GLU | 11 | 70.519 | 15.331 | 13.237 | 1.00 | 28.18 | R1 |
| ATOM | 66 | OE1 | GLU | 11 | 71.385 | 15.876 | 12.516 | 1.00 | 29.51 | R1 |
| ATOM | 67 | OE2 | GLU | 11 | 69.355 | 15.782 | 13.343 | 1.00 | 29.42 | R1 |
| ATOM | 68 | C | GLU | 11 | 67.437 | 13.647 | 14.089 | 1.00 | 22.12 | R1 |
| ATOM | 69 | O | GLU | 11 | 67.145 | 12.977 | 13.105 | 1.00 | 25.62 | R1 |
| ATOM | 70 | N | LYS | 12 | 66.745 | 14.725 | 14.448 | 1.00 | 24.26 | R1 |
| ATOM | 71 | H | LYS | 12 | 67.040 | 15.259 | 15.212 | 1.00 | 35.00 | R1 |
| ATOM | 72 | CA | LYS | 12 | 65.545 | 15.107 | 13.715 | 1.00 | 23.93 | R1 |
| ATOM | 73 | CB | LYS | 12 | 64.647 | 16.024 | 14.545 | 1.00 | 29.94 | R1 |
| ATOM | 74 | CG | LYS | 12 | 63.263 | 16.310 | 13.879 | 1.00 | 38.06 | R1 |
| ATOM | 75 | CD | LYS | 12 | 62.310 | 15.068 | 13.811 | 1.00 | 39.04 | R1 |
| ATOM | 76 | CE | LYS | 12 | 62.683 | 14.004 | 12.747 | 1.00 | 36.68 | R1 |
| ATOM | 77 | NZ | LYS | 12 | 62.388 | 14.402 | 11.344 | 1.00 | 32.23 | R1 |
| ATOM | 78 | HZ1 | LYS | 12 | 62.671 | 13.634 | 10.703 | 1.00 | 35.00 | R1 |
| ATOM | 79 | HZ2 | LYS | 12 | 62.911 | 15.267 | 11.103 | 1.00 | 35.00 | R1 |
| ATOM | 80 | HZ3 | LYS | 12 | 61.367 | 14.573 | 11.243 | 1.00 | 35.00 | R1 |
| ATOM | 81 | C | LYS | 12 | 65.724 | 15.687 | 12.319 | 1.00 | 19.62 | R1 |
| ATOM | 82 | O | LYS | 12 | 64.854 | 15.508 | 11.473 | 1.00 | 17.23 | R1 |
| ATOM | 83 | N | ILE | 13 | 66.824 | 16.399 | 12.077 | 1.00 | 16.54 | R1 |
| ATOM | 84 | H | ILE | 13 | 67.471 | 16.539 | 12.796 | 1.00 | 35.00 | R1 |
| ATOM | 85 | CA | ILE | 13 | 67.059 | 16.966 | 10.756 | 1.00 | 14.51 | R1 |
| ATOM | 86 | CB | ILE | 13 | 68.311 | 17.853 | 10.725 | 1.00 | 11.27 | R1 |
| ATOM | 87 | CG2 | ILE | 13 | 68.757 | 18.084 | 9.274 | 1.00 | 14.92 | R1 |
| ATOM | 88 | CG1 | ILE | 13 | 68.033 | 19.192 | 11.400 | 1.00 | 5.96 | R1 |
| ATOM | 89 | CD1 | ILE | 13 | 66.929 | 19.957 | 10.766 | 1.00 | 2.00 | R1 |
| ATOM | 90 | C | ILE | 13 | 67.205 | 15.881 | 9.683 | 1.00 | 12.30 | R1 |
| ATOM | 91 | O | ILE | 13 | 68.171 | 15.106 | 9.703 | 1.00 | 11.78 | R1 |
| ATOM | 92 | N | ILE | 14 | 66.227 | 15.817 | 8.776 | 1.00 | 10.08 | R1 |
| ATOM | 93 | H | ILE | 14 | 65.467 | 16.432 | 8.856 | 1.00 | 35.00 | R1 |
| ATOM | 94 | CA | ILE | 14 | 66.255 | 14.856 | 7.679 | 1.00 | 11.71 | R1 |
| ATOM | 95 | CB | ILE | 14 | 64.887 | 14.710 | 6.994 | 1.00 | 12.76 | R1 |
| ATOM | 96 | CG2 | ILE | 14 | 64.938 | 13.606 | 5.954 | 1.00 | 9.91 | R1 |
| ATOM | 97 | CG1 | ILE | 14 | 63.784 | 14.410 | 8.002 | 1.00 | 12.34 | R1 |
| ATOM | 98 | CD1 | ILE | 14 | 62.484 | 13.984 | 7.331 | 1.00 | 17.49 | R1 |
| ATOM | 99 | C | ILE | 14 | 67.174 | 15.445 | 6.623 | 1.00 | 7.27 | R1 |
| ATOM | 100 | O | ILE | 14 | 67.120 | 16.651 | 6.387 | 1.00 | 8.31 | R1 |
| ATOM | 101 | N | LEU | 15 | 68.069 | 14.624 | 6.071 | 1.00 | 4.70 | R1 |

TABLE 3-continued

Crystallographic coordinates for the refined co-crystal

| ATOM | 102 | H | LEU | 15 | 68.117 | 13.697 | 6.388 | 1.00 | 35.00 | R1 |
| ATOM | 103 | CA | LEU | 15 | 68.981 | 15.063 | 5.006 | 1.00 | 3.29 | R1 |
| ATOM | 104 | CB | LEU | 15 | 70.398 | 14.528 | 5.236 | 1.00 | 2.00 | R1 |
| ATOM | 105 | CG | LEU | 15 | 71.485 | 14.681 | 4.147 | 1.00 | 2.00 | R1 |
| ATOM | 106 | CD1 | LEU | 15 | 71.707 | 16.128 | 3.696 | 1.00 | 2.00 | R1 |
| ATOM | 107 | CD2 | LEU | 15 | 72.778 | 14.141 | 4.677 | 1.00 | 2.00 | R1 |
| ATOM | 108 | C | LEU | 15 | 68.477 | 14.548 | 3.657 | 1.00 | 2.04 | R1 |
| ATOM | 109 | O | LEU | 15 | 68.513 | 13.350 | 3.399 | 1.00 | 2.00 | R1 |
| ATOM | 110 | N | VAL | 16 | 67.990 | 15.440 | 2.797 | 1.00 | 3.30 | R1 |
| ATOM | 111 | H | VAL | 16 | 67.923 | 16.375 | 3.047 | 1.00 | 35.00 | R1 |
| ATOM | 112 | CA | VAL | 16 | 67.526 | 14.996 | 1.466 | 1.00 | 7.20 | R1 |
| ATOM | 113 | CB | VAL | 16 | 66.298 | 15.782 | 0.986 | 1.00 | 4.78 | R1 |
| ATOM | 114 | CG1 | VAL | 16 | 66.600 | 17.233 | 0.973 | 1.00 | 5.72 | R1 |
| ATOM | 115 | CG2 | VAL | 16 | 65.886 | 15.316 | −0.386 | 1.00 | 2.00 | R1 |
| ATOM | 116 | C | VAL | 16 | 68.577 | 14.954 | 0.326 | 1.00 | 2.47 | R1 |
| ATOM | 117 | O | VAL | 16 | 69.223 | 15.952 | −0.006 | 1.00 | 2.00 | R1 |
| ATOM | 118 | N | SER | 17 | 68.774 | 13.754 | −0.208 | 1.00 | 2.00 | R1 |
| ATOM | 119 | H | SER | 17 | 68.292 | 12.982 | 0.153 | 1.00 | 35.00 | R1 |
| ATOM | 120 | CA | SER | 17 | 69.692 | 13.549 | −1.305 | 1.00 | 2.48 | R1 |
| ATOM | 121 | CB | SER | 17 | 70.950 | 12.856 | −0.816 | 1.00 | 2.00 | R1 |
| ATOM | 122 | OG | SER | 17 | 70.648 | 11.590 | −0.302 | 1.00 | 3.68 | R1 |
| ATOM | 123 | HG | SER | 17 | 70.280 | 11.042 | −1.000 | 1.00 | 35.00 | R1 |
| ATOM | 124 | C | SER | 17 | 69.027 | 12.771 | −2.451 | 1.00 | 2.00 | R1 |
| ATOM | 125 | O | SER | 17 | 68.069 | 12.034 | −2.251 | 1.00 | 3.72 | R1 |
| ATOM | 126 | N | SER | 18 | 69.565 | 12.946 | −3.652 | 1.00 | 5.18 | R1 |
| ATOM | 127 | H | SER | 18 | 70.346 | 13.536 | −3.722 | 1.00 | 35.00 | R1 |
| ATOM | 128 | CA | SER | 18 | 69.078 | 12.314 | −4.883 | 1.00 | 2.15 | R1 |
| ATOM | 129 | CB | SER | 18 | 69.899 | 12.804 | −6.068 | 1.00 | 2.00 | R1 |
| ATOM | 130 | OG | SER | 18 | 69.753 | 14.194 | −6.268 | 1.00 | 8.36 | R1 |
| ATOM | 131 | HG | SER | 18 | 70.286 | 14.479 | −7.013 | 1.00 | 35.00 | R1 |
| ATOM | 132 | C | SER | 18 | 69.041 | 10.811 | −4.981 | 1.00 | 2.00 | R1 |
| ATOM | 133 | O | SER | 18 | 69.922 | 10.128 | −4.498 | 1.00 | 2.00 | R1 |
| ATOM | 134 | N | ALA | 19 | 68.028 | 10.316 | −5.684 | 1.00 | 2.11 | R1 |
| ATOM | 135 | H | ALA | 19 | 67.361 | 10.937 | −6.034 | 1.00 | 35.00 | R1 |
| ATOM | 136 | CA | ALA | 19 | 67.865 | 8.896 | −5.966 | 1.00 | 2.00 | R1 |
| ATOM | 137 | CB | ALA | 19 | 66.440 | 8.588 | −6.116 | 1.00 | 2.00 | R1 |
| ATOM | 138 | C | ALA | 19 | 68.608 | 8.616 | −7.285 | 1.00 | 2.00 | R1 |
| ATOM | 139 | O | ALA | 19 | 68.781 | 9.512 | −8.115 | 1.00 | 2.00 | R1 |
| ATOM | 140 | N | ASN | 20 | 69.081 | 7.388 | −7.466 | 1.00 | 3.88 | R1 |
| ATOM | 141 | H | ASN | 20 | 68.931 | 6.692 | −6.822 | 1.00 | 35.00 | R1 |
| ATOM | 142 | CA | ASN | 20 | 69.818 | 7.024 | −8.676 | 1.00 | 7.28 | R1 |
| ATOM | 143 | CB | ASN | 20 | 69.001 | 7.342 | −9.930 | 1.00 | 10.42 | R1 |
| ATOM | 144 | CG | ASN | 20 | 67.726 | 6.555 | −9.975 | 1.00 | 15.31 | R1 |
| ATOM | 145 | OD1 | ASN | 20 | 67.766 | 5.335 | −10.151 | 1.00 | 16.14 | R1 |
| ATOM | 146 | ND2 | ASN | 20 | 66.586 | 7.219 | −9.722 | 1.00 | 13.46 | R1 |
| ATOM | 147 | HD21 | ASN | 20 | 66.639 | 8.178 | −9.525 | 1.00 | 35.00 | R1 |
| ATOM | 148 | HD22 | ASN | 20 | 65.745 | 6.715 | −9.728 | 1.00 | 35.00 | R1 |
| ATOM | 149 | C | ASN | 20 | 71.104 | 7.805 | −8.668 | 1.00 | 7.76 | R1 |
| ATOM | 150 | O | ASN | 20 | 71.594 | 8.276 | −9.701 | 1.00 | 13.80 | R1 |
| ATOM | 151 | N | GLU | 21 | 71.610 | 7.982 | −7.462 | 1.00 | 5.59 | R1 |
| ATOM | 152 | H | GLU | 21 | 71.114 | 7.626 | −6.697 | 1.00 | 35.00 | R1 |
| ATOM | 153 | CA | GLU | 21 | 72.839 | 8.684 | −7.222 | 1.00 | 2.69 | R1 |
| ATOM | 154 | CB | GLU | 21 | 72.497 | 10.145 | −6.917 | 1.00 | 2.00 | R1 |
| ATOM | 155 | CG | GLU | 21 | 73.496 | 11.140 | −7.430 | 1.00 | 2.00 | R1 |
| ATOM | 156 | CD | GLU | 21 | 72.922 | 12.517 | −7.628 | 1.00 | 2.00 | R1 |
| ATOM | 157 | OE1 | GLU | 21 | 73.291 | 13.445 | −6.920 | 1.00 | 2.00 | R1 |
| ATOM | 158 | OE2 | GLU | 21 | 72.104 | 12.704 | −8.520 | 1.00 | 6.00 | R1 |
| ATOM | 159 | C | GLU | 21 | 73.401 | 7.903 | −6.024 | 1.00 | 3.79 | R1 |
| ATOM | 160 | O | GLU | 21 | 72.657 | 7.242 | −5.311 | 1.00 | 2.00 | R1 |
| ATOM | 161 | N | ILE | 22 | 74.718 | 7.887 | −5.860 | 1.00 | 8.40 | R1 |
| ATOM | 162 | H | ILE | 22 | 75.252 | 8.395 | −6.506 | 1.00 | 35.00 | R1 |
| ATOM | 163 | CA | ILE | 22 | 75.357 | 7.151 | −4.750 | 1.00 | 8.36 | R1 |
| ATOM | 164 | CB | ILE | 22 | 76.771 | 6.686 | −5.179 | 1.00 | 3.92 | R1 |
| ATOM | 165 | CG2 | ILE | 22 | 77.475 | 7.811 | −5.859 | 1.00 | 2.00 | R1 |
| ATOM | 166 | CG1 | ILE | 22 | 77.553 | 6.127 | −3.992 | 1.00 | 3.11 | R1 |
| ATOM | 167 | CD1 | ILE | 22 | 78.880 | 5.551 | −4.316 | 1.00 | 2.00 | R1 |
| ATOM | 168 | C | ILE | 22 | 75.435 | 7.945 | −3.437 | 1.00 | 11.28 | R1 |
| ATOM | 169 | O | ILE | 22 | 75.993 | 9.044 | −3.404 | 1.00 | 14.74 | R1 |
| ATOM | 170 | N | ASP | 23 | 74.902 | 7.396 | −2.345 | 1.00 | 14.99 | R1 |
| ATOM | 171 | H | ASP | 23 | 74.483 | 6.518 | −2.401 | 1.00 | 35.00 | R1 |
| ATOM | 172 | CA | ASP | 23 | 74.939 | 8.124 | −1.062 | 1.00 | 16.11 | R1 |
| ATOM | 173 | CB | ASP | 23 | 73.547 | 8.584 | −0.656 | 1.00 | 19.89 | R1 |
| ATOM | 174 | CG | ASP | 23 | 73.576 | 9.834 | 0.199 | 1.00 | 22.69 | R1 |
| ATOM | 175 | OD1 | ASP | 23 | 74.626 | 10.523 | 0.209 | 1.00 | 22.64 | R1 |
| ATOM | 176 | OD2 | ASP | 23 | 72.536 | 10.139 | 0.828 | 1.00 | 19.11 | R1 |
| ATOM | 177 | C | ASP | 23 | 75.548 | 7.400 | 0.114 | 1.00 | 13.06 | R1 |
| ATOM | 178 | O | ASP | 23 | 75.668 | 6.175 | 0.111 | 1.00 | 14.43 | R1 |

TABLE 3-continued

Crystallographic coordinates for the refined co-crystal

| ATOM | 179 | N | VAL | 24 | 75.880 | 8.165 | 1.149 | 1.00 | 12.19 | R1 |
|---|---|---|---|---|---|---|---|---|---|---|
| ATOM | 180 | H | VAL | 24 | 75.752 | 9.129 | 1.120 | 1.00 | 35.00 | R1 |
| ATOM | 181 | CA | VAL | 24 | 76.489 | 7.603 | 2.348 | 1.00 | 13.16 | R1 |
| ATOM | 182 | CB | VAL | 24 | 78.032 | 7.646 | 2.239 | 1.00 | 11.85 | R1 |
| ATOM | 183 | CG1 | VAL | 24 | 78.587 | 8.931 | 2.831 | 1.00 | 10.67 | R1 |
| ATOM | 184 | CG2 | VAL | 24 | 78.630 | 6.430 | 2.896 | 1.00 | 12.84 | R1 |
| ATOM | 185 | C | VAL | 24 | 76.007 | 8.318 | 3.620 | 1.00 | 13.91 | R1 |
| ATOM | 186 | O | VAL | 24 | 75.580 | 9.471 | 3.566 | 1.00 | 17.75 | R1 |
| ATOM | 187 | N | ARG | 25 | 76.055 | 7.621 | 4.752 | 1.00 | 12.98 | R1 |
| ATOM | 188 | H | ARG | 25 | 76.406 | 6.708 | 4.737 | 1.00 | 35.00 | R1 |
| ATOM | 189 | CA | ARG | 25 | 75.612 | 8.176 | 6.033 | 1.00 | 13.84 | R1 |
| ATOM | 190 | CB | ARG | 25 | 74.168 | 7.779 | 6.299 | 1.00 | 11.64 | R1 |
| ATOM | 191 | CG | ARG | 25 | 73.187 | 8.189 | 5.244 | 1.00 | 9.02 | R1 |
| ATOM | 192 | CD | ARG | 25 | 73.095 | 9.664 | 5.185 | 1.00 | 7.39 | R1 |
| ATOM | 193 | NE | ARG | 25 | 71.790 | 10.068 | 4.707 | 1.00 | 7.13 | R1 |
| ATOM | 194 | HE | ARG | 25 | 70.992 | 9.682 | 5.127 | 1.00 | 35.00 | R1 |
| ATOM | 195 | CZ | ARG | 25 | 71.625 | 10.948 | 3.742 | 1.00 | 9.45 | R1 |
| ATOM | 196 | NH1 | ARG | 25 | 72.701 | 11.489 | 3.187 | 1.00 | 13.23 | R1 |
| ATOM | 197 | HH11 | ARG | 25 | 73.621 | 11.243 | 3.494 | 1.00 | 35.00 | R1 |
| ATOM | 198 | HH12 | ARG | 25 | 72.589 | 12.165 | 2.459 | 1.00 | 35.00 | R1 |
| ATOM | 199 | NH2 | ARG | 25 | 70.409 | 11.277 | 3.326 | 1.00 | 6.00 | R1 |
| ATOM | 200 | HH21 | ARG | 25 | 69.607 | 10.870 | 3.751 | 1.00 | 35.00 | R1 |
| ATOM | 201 | HH22 | ARG | 25 | 70.297 | 11.957 | 2.600 | 1.00 | 35.00 | R1 |
| ATOM | 202 | C | ARG | 25 | 76.467 | 7.723 | 7.237 | 1.00 | 14.08 | R1 |
| ATOM | 203 | O | ARG | 25 | 76.498 | 6.537 | 7.610 | 1.00 | 12.29 | R1 |
| ATOM | 204 | N | PRO | 26 | 77.151 | 8.677 | 7.874 | 1.00 | 12.74 | R1 |
| ATOM | 205 | CD | PRO | 26 | 77.186 | 10.090 | 7.449 | 1.00 | 15.29 | R1 |
| ATOM | 206 | CA | PRO | 26 | 78.014 | 8.446 | 9.036 | 1.00 | 10.56 | R1 |
| ATOM | 207 | CB | PRO | 26 | 79.014 | 9.573 | 8.917 | 1.00 | 11.58 | R1 |
| ATOM | 208 | CG | PRO | 26 | 78.113 | 10.725 | 8.477 | 1.00 | 16.50 | R1 |
| ATOM | 209 | C | PRO | 26 | 77.193 | 8.579 | 10.320 | 1.00 | 9.64 | R1 |
| ATOM | 210 | O | PRO | 26 | 76.279 | 9.394 | 10.376 | 1.00 | 6.56 | R1 |
| ATOM | 211 | N | CYS | 27 | 77.490 | 7.768 | 11.333 | 1.00 | 6.07 | R1 |
| ATOM | 212 | H | CYS | 27 | 78.216 | 7.116 | 11.236 | 1.00 | 35.00 | R1 |
| ATOM | 213 | CA | CYS | 27 | 76.736 | 7.857 | 12.572 | 1.00 | 6.10 | R1 |
| ATOM | 214 | C | CYS | 27 | 76.935 | 9.192 | 13.269 | 1.00 | 3.89 | R1 |
| ATOM | 215 | O | CYS | 27 | 78.004 | 9.463 | 13.815 | 1.00 | 3.24 | R1 |
| ATOM | 216 | CB | CYS | 27 | 77.163 | 6.775 | 13.536 | 1.00 | 12.34 | R1 |
| ATOM | 217 | SG | CYS | 27 | 75.844 | 6.315 | 14.686 | 1.00 | 9.29 | R1 |
| ATOM | 218 | N | PRO | 28 | 75.876 | 9.993 | 13.363 | 1.00 | 2.68 | R1 |
| ATOM | 219 | CD | PRO | 28 | 74.500 | 9.705 | 12.941 | 1.00 | 2.00 | R1 |
| ATOM | 220 | CA | PRO | 28 | 75.956 | 11.297 | 14.005 | 1.00 | 5.84 | R1 |
| ATOM | 221 | CB | PRO | 28 | 74.568 | 11.857 | 13.750 | 1.00 | 2.28 | R1 |
| ATOM | 222 | CG | PRO | 28 | 73.732 | 10.673 | 13.717 | 1.00 | 2.00 | R1 |
| ATOM | 223 | C | PRO | 28 | 76.333 | 11.235 | 15.495 | 1.00 | 12.29 | R1 |
| ATOM | 224 | O | PRO | 28 | 75.476 | 11.293 | 16.371 | 1.00 | 14.91 | R1 |
| ATOM | 225 | N | LEU | 29 | 77.631 | 11.151 | 15.770 | 1.00 | 19.19 | R1 |
| ATOM | 226 | H | LEU | 29 | 78.270 | 11.168 | 15.029 | 1.00 | 35.00 | R1 |
| ATOM | 227 | CA | LEU | 29 | 78.132 | 11.054 | 17.138 | 1.00 | 25.68 | R1 |
| ATOM | 228 | CB | LEU | 29 | 78.916 | 9.756 | 17.319 | 1.00 | 25.51 | R1 |
| ATOM | 229 | CG | LEU | 29 | 78.335 | 8.407 | 16.911 | 1.00 | 25.38 | R1 |
| ATOM | 230 | CD1 | LEU | 29 | 79.482 | 7.422 | 16.775 | 1.00 | 26.27 | R1 |
| ATOM | 231 | CD2 | LEU | 29 | 77.313 | 7.926 | 17.911 | 1.00 | 19.14 | R1 |
| ATOM | 232 | C | LEU | 29 | 79.080 | 12.177 | 17.497 | 1.00 | 30.89 | R1 |
| ATOM | 233 | O | LEU | 29 | 79.941 | 12.548 | 16.698 | 1.00 | 32.21 | R1 |
| ATOM | 234 | N | ASN | 30 | 78.977 | 12.645 | 18.739 | 1.00 | 35.31 | R1 |
| ATOM | 235 | H | ASN | 30 | 78.300 | 12.252 | 19.330 | 1.00 | 35.00 | R1 |
| ATOM | 236 | CA | ASN | 30 | 79.855 | 13.695 | 19.263 | 1.00 | 37.97 | R1 |
| ATOM | 237 | CB | ASN | 30 | 79.271 | 14.231 | 20.569 | 1.00 | 40.34 | R1 |
| ATOM | 238 | CG | ASN | 30 | 77.750 | 14.441 | 20.483 | 1.00 | 44.12 | R1 |
| ATOM | 239 | OD1 | ASN | 30 | 77.002 | 14.055 | 21.387 | 1.00 | 41.85 | R1 |
| ATOM | 240 | ND2 | ASN | 30 | 77.289 | 15.024 | 19.376 | 1.00 | 45.70 | R1 |
| ATOM | 241 | HD21 | ASN | 30 | 77.921 | 15.294 | 18.677 | 1.00 | 35.00 | R1 |
| ATOM | 242 | HD22 | ASN | 30 | 76.322 | 15.161 | 19.302 | 1.00 | 35.00 | R1 |
| ATOM | 243 | C | ASN | 30 | 81.197 | 12.975 | 19.471 | 1.00 | 40.39 | R1 |
| ATOM | 244 | O | ASN | 30 | 81.216 | 11.821 | 19.887 | 1.00 | 38.81 | R1 |
| ATOM | 245 | N | PRO | 31 | 82.329 | 13.632 | 19.156 | 1.00 | 40.32 | R1 |
| ATOM | 246 | CD | PRO | 31 | 82.383 | 15.092 | 19.021 | 1.00 | 41.67 | R1 |
| ATOM | 247 | CA | PRO | 31 | 83.694 | 13.092 | 19.272 | 1.00 | 41.58 | R1 |
| ATOM | 248 | CB | PRO | 31 | 84.564 | 14.350 | 19.259 | 1.00 | 40.21 | R1 |
| ATOM | 249 | CG | PRO | 31 | 83.643 | 15.406 | 19.765 | 1.00 | 40.81 | R1 |
| ATOM | 250 | C | PRO | 31 | 84.001 | 12.194 | 20.468 | 1.00 | 41.50 | R1 |
| ATOM | 251 | O | PRO | 31 | 84.921 | 11.376 | 20.422 | 1.00 | 38.97 | R1 |
| ATOM | 252 | N | ASN | 32 | 83.214 | 12.336 | 21.527 | 1.00 | 44.79 | R1 |
| ATOM | 253 | H | ASN | 32 | 82.500 | 13.004 | 21.507 | 1.00 | 35.00 | R1 |
| ATOM | 254 | CA | ASN | 32 | 83.389 | 11.537 | 22.734 | 1.00 | 47.74 | R1 |
| ATOM | 255 | CB | ASN | 32 | 83.135 | 12.405 | 23.969 | 1.00 | 47.85 | R1 |

TABLE 3-continued

Crystallographic coordinates for the refined co-crystal

| ATOM | 256 | CG | ASN | 32 | 81.787 | 13.103 | 23.924 | 1.00 | 49.20 | R1 |
| ATOM | 257 | OD1 | ASN | 32 | 80.788 | 12.583 | 24.426 | 1.00 | 47.66 | R1 |
| ATOM | 258 | ND2 | ASN | 32 | 81.752 | 14.286 | 23.307 | 1.00 | 50.56 | R1 |
| ATOM | 259 | HD21 | ASN | 32 | 82.581 | 14.637 | 22.921 | 1.00 | 35.00 | R1 |
| ATOM | 260 | HD22 | ASN | 32 | 80.891 | 14.751 | 23.272 | 1.00 | 35.00 | R1 |
| ATOM | 261 | C | ASN | 32 | 82.494 | 10.291 | 22.783 | 1.00 | 47.72 | R1 |
| ATOM | 262 | O | ASN | 32 | 82.255 | 9.749 | 23.861 | 1.00 | 50.60 | R1 |
| ATOM | 263 | N | GLU | 33 | 82.017 | 9.831 | 21.626 | 1.00 | 47.48 | R1 |
| ATOM | 264 | H | GLU | 33 | 82.264 | 10.285 | 20.796 | 1.00 | 35.00 | R1 |
| ATOM | 265 | CA | GLU | 33 | 81.151 | 8.650 | 21.562 | 1.00 | 44.97 | R1 |
| ATOM | 266 | CB | GLU | 33 | 79.720 | 9.053 | 21.229 | 1.00 | 45.74 | R1 |
| ATOM | 267 | CG | GLU | 33 | 79.084 | 10.006 | 22.219 | 1.00 | 47.26 | R1 |
| ATOM | 268 | CD | GLU | 33 | 77.754 | 10.564 | 21.733 | 1.00 | 49.23 | R1 |
| ATOM | 269 | OE1 | GLU | 33 | 77.203 | 11.456 | 22.407 | 1.00 | 52.48 | R1 |
| ATOM | 270 | OE2 | GLU | 33 | 77.257 | 10.127 | 20.674 | 1.00 | 50.04 | R1 |
| ATOM | 271 | C | GLU | 33 | 81.612 | 7.579 | 20.570 | 1.00 | 43.70 | R1 |
| ATOM | 272 | O | GLU | 33 | 80.931 | 6.576 | 20.392 | 1.00 | 42.03 | R1 |
| ATOM | 273 | N | HIS | 34 | 82.748 | 7.805 | 19.909 | 1.00 | 44.18 | R1 |
| ATOM | 274 | H | HIS | 34 | 83.220 | 8.652 | 20.061 | 1.00 | 35.00 | R1 |
| ATOM | 275 | CA | HIS | 34 | 83.302 | 6.836 | 18.962 | 1.00 | 44.39 | R1 |
| ATOM | 276 | CB | HIS | 34 | 84.167 | 7.548 | 17.922 | 1.00 | 43.25 | R1 |
| ATOM | 277 | CG | HIS | 34 | 83.376 | 8.245 | 16.866 | 1.00 | 44.28 | R1 |
| ATOM | 278 | CD2 | HIS | 34 | 82.649 | 9.387 | 16.902 | 1.00 | 45.77 | R1 |
| ATOM | 279 | ND1 | HIS | 34 | 83.220 | 7.730 | 15.598 | 1.00 | 45.42 | R1 |
| ATOM | 280 | HD1 | HIS | 34 | 83.644 | 6.914 | 15.262 | 1.00 | 35.00 | R1 |
| ATOM | 281 | CE1 | HIS | 34 | 82.425 | 8.521 | 14.899 | 1.00 | 46.74 | R1 |
| ATOM | 282 | NE2 | HIS | 34 | 82.064 | 9.533 | 15.668 | 1.00 | 45.10 | R1 |
| ATOM | 283 | HE2 | HIS | 34 | 81.455 | 10.257 | 15.409 | 1.00 | 35.00 | R1 |
| ATOM | 284 | C | HIS | 34 | 84.124 | 5.768 | 19.700 | 1.00 | 45.03 | R1 |
| ATOM | 285 | O | HIS | 34 | 85.178 | 5.328 | 19.233 | 1.00 | 45.81 | R1 |
| ATOM | 286 | N | LYS | 35 | 83.615 | 5.339 | 20.849 | 1.00 | 45.80 | R1 |
| ATOM | 287 | H | LYS | 35 | 82.764 | 5.685 | 21.176 | 1.00 | 35.00 | R1 |
| ATOM | 288 | CA | LYS | 35 | 84.296 | 4.351 | 21.663 | 1.00 | 46.43 | R1 |
| ATOM | 289 | CB | LYS | 35 | 83.891 | 4.512 | 23.135 | 1.00 | 48.38 | R1 |
| ATOM | 290 | CG | LYS | 35 | 84.032 | 5.932 | 23.681 | 1.00 | 50.02 | R1 |
| ATOM | 291 | CD | LYS | 35 | 85.382 | 6.584 | 23.339 | 1.00 | 51.42 | R1 |
| ATOM | 292 | CE | LYS | 35 | 86.580 | 5.830 | 23.921 | 1.00 | 52.34 | R1 |
| ATOM | 293 | NZ | LYS | 35 | 86.959 | 4.590 | 23.163 | 1.00 | 51.92 | R1 |
| ATOM | 294 | HZ1 | LYS | 35 | 86.183 | 3.901 | 23.179 | 1.00 | 35.00 | R1 |
| ATOM | 295 | HZ2 | LYS | 35 | 87.793 | 4.161 | 23.613 | 1.00 | 35.00 | R1 |
| ATOM | 296 | HZ3 | LYS | 35 | 87.187 | 4.838 | 22.179 | 1.00 | 35.00 | R1 |
| ATOM | 297 | C | LYS | 35 | 83.999 | 2.937 | 21.201 | 1.00 | 45.87 | R1 |
| ATOM | 298 | O | LYS | 35 | 84.919 | 2.170 | 20.897 | 1.00 | 45.62 | R1 |
| ATOM | 299 | N | GLY | 36 | 82.705 | 2.621 | 21.137 | 1.00 | 43.41 | R1 |
| ATOM | 300 | H | GLY | 36 | 82.036 | 3.298 | 21.372 | 1.00 | 35.00 | R1 |
| ATOM | 301 | CA | GLY | 36 | 82.247 | 1.298 | 20.744 | 1.00 | 42.11 | R1 |
| ATOM | 302 | C | GLY | 36 | 82.357 | 0.829 | 19.299 | 1.00 | 41.39 | R1 |
| ATOM | 303 | O | GLY | 36 | 83.024 | 1.447 | 18.464 | 1.00 | 44.38 | R1 |
| ATOM | 304 | N | THR | 37 | 81.680 | −0.285 | 19.025 | 1.00 | 37.66 | R1 |
| ATOM | 305 | H | THR | 37 | 81.158 | −0.668 | 19.760 | 1.00 | 35.00 | R1 |
| ATOM | 306 | CA | THR | 37 | 81.653 | −0.942 | 17.714 | 1.00 | 34.23 | R1 |
| ATOM | 307 | CB | THR | 37 | 81.873 | −2.473 | 17.890 | 1.00 | 32.81 | R1 |
| ATOM | 308 | OG1 | THR | 37 | 81.448 | −3.175 | 16.720 | 1.00 | 31.81 | R1 |
| ATOM | 309 | HG1 | THR | 37 | 80.506 | −3.069 | 16.576 | 1.00 | 35.00 | R1 |
| ATOM | 310 | CG2 | THR | 37 | 81.104 | −2.991 | 19.091 | 1.00 | 32.22 | R1 |
| ATOM | 311 | C | THR | 37 | 80.334 | −0.684 | 16.976 | 1.00 | 29.72 | R1 |
| ATOM | 312 | O | THR | 37 | 79.351 | −1.410 | 17.183 | 1.00 | 30.61 | R1 |
| ATOM | 313 | N | ILE | 38 | 80.346 | 0.305 | 16.078 | 1.00 | 22.92 | R1 |
| ATOM | 314 | H | ILE | 38 | 81.190 | 0.776 | 15.917 | 1.00 | 35.00 | R1 |
| ATOM | 315 | CA | ILE | 38 | 79.160 | 0.701 | 15.303 | 1.00 | 17.70 | R1 |
| ATOM | 316 | CB | ILE | 38 | 79.445 | 1.975 | 14.492 | 1.00 | 12.97 | R1 |
| ATOM | 317 | CG2 | ILE | 38 | 78.253 | 2.310 | 13.574 | 1.00 | 6.53 | R1 |
| ATOM | 318 | CG1 | ILE | 38 | 79.717 | 3.117 | 15.467 | 1.00 | 12.27 | R1 |
| ATOM | 319 | CD1 | ILE | 38 | 80.273 | 4.380 | 14.876 | 1.00 | 5.83 | R1 |
| ATOM | 320 | C | ILE | 38 | 78.474 | −0.326 | 14.384 | 1.00 | 17.13 | R1 |
| ATOM | 321 | O | ILE | 38 | 79.110 | −0.953 | 13.538 | 1.00 | 18.79 | R1 |
| ATOM | 322 | N | THR | 39 | 77.155 | −0.447 | 14.543 | 1.00 | 18.18 | R1 |
| ATOM | 323 | H | THR | 39 | 76.712 | 0.102 | 15.219 | 1.00 | 35.00 | R1 |
| ATOM | 324 | CA | THR | 39 | 76.321 | −1.356 | 13.745 | 1.00 | 18.86 | R1 |
| ATOM | 325 | CB | THR | 39 | 75.830 | −2.564 | 14.579 | 1.00 | 23.13 | R1 |
| ATOM | 326 | OG1 | THR | 39 | 76.837 | −2.943 | 15.528 | 1.00 | 29.75 | R1 |
| ATOM | 327 | HG1 | THR | 39 | 77.626 | −3.219 | 15.058 | 1.00 | 35.00 | R1 |
| ATOM | 328 | CG2 | TER | 39 | 75.543 | −3.751 | 13.664 | 1.00 | 25.40 | R1 |
| ATOM | 329 | C | THR | 39 | 75.091 | −0.587 | 13.217 | 1.00 | 13.82 | R1 |
| ATOM | 330 | O | THR | 39 | 74.679 | 0.412 | 13.813 | 1.00 | 13.75 | R1 |
| ATOM | 331 | N | TRP | 40 | 74.507 | −1.051 | 12.116 | 1.00 | 5.52 | R1 |
| ATOM | 332 | H | TRP | 40 | 74.847 | −1.868 | 11.695 | 1.00 | 35.00 | R1 |

TABLE 3-continued

Crystallographic coordinates for the refined co-crystal

| ATOM | 333 | CA | TRP | 40 | 73.354 | −0.373 | 11.524 | 1.00 | 2.79 | R1 |
|---|---|---|---|---|---|---|---|---|---|---|
| ATOM | 334 | CB | TRP | 40 | 73.685 | 0.178 | 10.127 | 1.00 | 2.00 | R1 |
| ATOM | 335 | CG | TRP | 40 | 74.377 | 1.486 | 10.116 | 1.00 | 2.00 | R1 |
| ATOM | 336 | CD2 | TRP | 40 | 73.772 | 2.781 | 9.988 | 1.00 | 2.59 | R1 |
| ATOM | 337 | CE2 | TRP | 40 | 74.813 | 3.733 | 10.012 | 1.00 | 2.00 | R1 |
| ATOM | 338 | CE3 | TRP | 40 | 72.450 | 3.230 | 9.856 | 1.00 | 2.00 | R1 |
| ATOM | 339 | CD1 | TRP | 40 | 75.712 | 1.702 | 10.212 | 1.00 | 2.00 | R1 |
| ATOM | 340 | NE1 | TRP | 40 | 75.986 | 3.048 | 10.149 | 1.00 | 2.00 | R1 |
| ATOM | 341 | HE1 | TRP | 40 | 76.880 | 3.447 | 10.197 | 1.00 | 35.00 | R1 |
| ATOM | 342 | CZ2 | TRP | 40 | 74.579 | 5.097 | 9.908 | 1.00 | 2.00 | R1 |
| ATOM | 343 | CZ3 | TRP | 40 | 72.220 | 4.590 | 9.753 | 1.00 | 2.00 | R1 |
| ATOM | 344 | CH2 | TRP | 40 | 73.281 | 5.507 | 9.780 | 1.00 | 2.55 | R1 |
| ATOM | 345 | C | TRP | 40 | 72.122 | −1.265 | 11.443 | 1.00 | 2.47 | R1 |
| ATOM | 346 | O | TRP | 40 | 72.228 | −2.488 | 11.388 | 1.00 | 2.00 | R1 |
| ATOM | 347 | N | TYR | 41 | 70.956 | −0.621 | 11.396 | 1.00 | 3.90 | R1 |
| ATOM | 348 | H | TYR | 41 | 70.967 | 0.356 | 11.369 | 1.00 | 35.00 | R1 |
| ATOM | 349 | CA | TYR | 41 | 69.665 | −1.289 | 11.357 | 1.00 | 4.58 | R1 |
| ATOM | 350 | CB | TYR | 41 | 69.130 | −1.420 | 12.779 | 1.00 | 5.59 | R1 |
| ATOM | 351 | CG | TYR | 41 | 70.050 | −2.211 | 13.643 | 1.00 | 4.02 | R1 |
| ATOM | 352 | CD1 | TYR | 41 | 70.951 | −1.585 | 14.488 | 1.00 | 2.00 | R1 |
| ATOM | 353 | CE1 | TYR | 41 | 71.911 | −2.301 | 15.142 | 1.00 | 2.00 | R1 |
| ATOM | 354 | CD2 | TYR | 41 | 70.124 | −3.584 | 13.497 | 1.00 | 2.88 | R1 |
| ATOM | 355 | CE2 | TYR | 41 | 71.080 | −4.305 | 14.161 | 1.00 | 5.35 | R1 |
| ATOM | 356 | CZ | TYR | 41 | 71.972 | −3.658 | 14.976 | 1.00 | 2.00 | R1 |
| ATOM | 357 | OH | TYR | 41 | 72.912 | −4.415 | 15.607 | 1.00 | 2.00 | R1 |
| ATOM | 358 | HH | TYR | 41 | 72.810 | −5.335 | 15.354 | 1.00 | 35.00 | R1 |
| ATOM | 359 | C | TYR | 41 | 68.695 | −0.447 | 10.581 | 1.00 | 6.16 | R1 |
| ATOM | 360 | O | TYR | 41 | 68.891 | 0.757 | 10.484 | 1.00 | 2.00 | R1 |
| ATOM | 361 | N | LYS | 42 | 67.647 | −1.086 | 10.048 | 1.00 | 13.59 | R1 |
| ATOM | 362 | H | LYS | 42 | 67.570 | −2.053 | 10.179 | 1.00 | 35.00 | R1 |
| ATOM | 363 | CA | LYS | 42 | 66.587 | −0.409 | 9.284 | 1.00 | 19.64 | R1 |
| ATOM | 364 | CB | LYS | 42 | 66.137 | −1.281 | 8.115 | 1.00 | 17.19 | R1 |
| ATOM | 365 | CG | LYS | 42 | 66.047 | −0.570 | 6.759 | 1.00 | 15.07 | R1 |
| ATOM | 366 | CD | LYS | 42 | 65.645 | −1.579 | 5.666 | 1.00 | 15.22 | R1 |
| ATOM | 367 | CE | LYS | 42 | 65.659 | −0.997 | 4.250 | 1.00 | 15.71 | R1 |
| ATOM | 368 | NZ | LYS | 42 | 64.496 | −0.116 | 3.917 | 1.00 | 15.57 | R1 |
| ATOM | 369 | HZ1 | LYS | 42 | 64.481 | 0.670 | 4.598 | 1.00 | 35.00 | R1 |
| ATOM | 370 | HZ2 | LYS | 42 | 63.610 | −0.655 | 3.976 | 1.00 | 35.00 | R1 |
| ATOM | 371 | HZ3 | LYS | 42 | 64.619 | 0.263 | 2.956 | 1.00 | 35.00 | R1 |
| ATOM | 372 | C | LYS | 42 | 65.409 | −0.104 | 10.228 | 1.00 | 24.20 | R1 |
| ATOM | 373 | O | LYS | 42 | 65.560 | −0.209 | 11.447 | 1.00 | 27.43 | R1 |
| ATOM | 374 | N | ASP | 43 | 64.242 | 0.255 | 9.692 | 1.00 | 32.08 | R1 |
| ATOM | 375 | H | ASP | 43 | 64.132 | 0.308 | 8.720 | 1.00 | 35.00 | R1 |
| ATOM | 376 | CA | ASP | 43 | 63.113 | 0.598 | 10.557 | 1.00 | 38.11 | R1 |
| ATOM | 377 | CB | ASP | 43 | 61.961 | 1.257 | 9.788 | 1.00 | 41.00 | R1 |
| ATOM | 378 | CG | ASP | 43 | 60.835 | 1.750 | 10.724 | 1.00 | 44.46 | R1 |
| ATOM | 379 | OD1 | ASP | 43 | 61.027 | 2.808 | 11.377 | 1.00 | 44.02 | R1 |
| ATOM | 380 | OD2 | ASP | 43 | 59.769 | 1.077 | 10.819 | 1.00 | 42.16 | R1 |
| ATOM | 381 | C | ASP | 43 | 62.553 | −0.514 | 11.414 | 1.00 | 40.18 | R1 |
| ATOM | 382 | O | ASP | 43 | 61.950 | −1.467 | 10.912 | 1.00 | 44.31 | R1 |
| ATOM | 383 | N | ASP | 44 | 62.743 | −0.353 | 12.717 | 1.00 | 42.97 | R1 |
| ATOM | 384 | H | ASP | 44 | 63.255 | 0.424 | 13.022 | 1.00 | 35.00 | R1 |
| ATOM | 385 | CA | ASP | 44 | 62.240 | −1.276 | 13.723 | 1.00 | 44.96 | R1 |
| ATOM | 386 | CB | ASP | 44 | 60.826 | −0.865 | 14.119 | 1.00 | 47.69 | R1 |
| ATOM | 387 | CG | ASP | 44 | 60.750 | 0.569 | 14.613 | 1.00 | 53.09 | R1 |
| ATOM | 388 | OD1 | ASP | 44 | 61.782 | 1.280 | 14.597 | 1.00 | 54.07 | R1 |
| ATOM | 389 | OD2 | ASP | 44 | 59.646 | 0.990 | 15.025 | 1.00 | 55.00 | R1 |
| ATOM | 390 | C | ASP | 44 | 62.258 | −2.742 | 13.343 | 1.00 | 44.14 | R1 |
| ATOM | 391 | O | ASP | 44 | 61.281 | −3.445 | 13.551 | 1.00 | 45.00 | R1 |
| ATOM | 392 | N | SER | 45 | 63.376 | −3.192 | 12.788 | 1.00 | 45.25 | R1 |
| ATOM | 393 | H | SER | 45 | 64.118 | −2.568 | 12.646 | 1.00 | 35.00 | R1 |
| ATOM | 394 | CA | SER | 45 | 63.546 | −4.579 | 12.381 | 1.00 | 44.92 | R1 |
| ATOM | 395 | CB | SER | 45 | 63.196 | −4.746 | 10.897 | 1.00 | 47.00 | R1 |
| ATOM | 396 | OG | SER | 45 | 63.001 | −6.116 | 10.565 | 1.00 | 50.44 | R1 |
| ATOM | 397 | HG | SER | 45 | 62.772 | −6.197 | 9.636 | 1.00 | 35.00 | R1 |
| ATOM | 398 | C | SER | 45 | 65.017 | −4.866 | 12.636 | 1.00 | 42.49 | R1 |
| ATOM | 399 | O | SER | 45 | 65.802 | −5.090 | 11.709 | 1.00 | 38.59 | R1 |
| ATOM | 400 | N | LYS | 46 | 65.359 | −4.884 | 13.921 | 1.00 | 39.56 | R1 |
| ATOM | 401 | H | LYS | 46 | 64.653 | −4.770 | 14.591 | 1.00 | 35.00 | R1 |
| ATOM | 402 | CA | LYS | 46 | 66.732 | −5.077 | 14.375 | 1.00 | 38.07 | R1 |
| ATOM | 403 | CB | LYS | 46 | 66.912 | −4.558 | 15.803 | 1.00 | 34.59 | R1 |
| ATOM | 404 | CG | LYS | 46 | 66.916 | −3.004 | 15.904 | 1.00 | 29.31 | R1 |
| ATOM | 405 | CD | LYS | 46 | 65.896 | −2.353 | 14.954 | 1.00 | 21.71 | R1 |
| ATOM | 406 | CE | LYS | 46 | 65.439 | −0.995 | 15.420 | 1.00 | 20.46 | R1 |
| ATOM | 407 | NZ | LYS | 46 | 64.509 | −1.057 | 16.582 | 1.00 | 16.09 | R1 |
| ATOM | 408 | HZ1 | LYS | 46 | 64.991 | −1.511 | 17.384 | 1.00 | 35.00 | R1 |
| ATOM | 409 | HZ2 | LYS | 46 | 63.656 | −1.598 | 16.332 | 1.00 | 35.00 | R1 |

TABLE 3-continued

Crystallographic coordinates for the refined co-crystal

| ATOM | 410 | HZ3 | LYS | 46 | 64.238 | −0.088 | 16.846 | 1.00 | 35.00 | R1 |
|------|-----|-----|-----|----|--------|--------|--------|------|-------|-----|
| ATOM | 411 | C | LYS | 46 | 67.454 | −6.399 | 14.119 | 1.00 | 37.13 | R1 |
| ATOM | 412 | O | LYS | 46 | 67.703 | −7.229 | 15.011 | 1.00 | 33.69 | R1 |
| ATOM | 413 | N | THR | 47 | 67.758 | −6.520 | 12.827 | 1.00 | 35.95 | R1 |
| ATOM | 414 | H | THR | 47 | 67.452 | −5.784 | 12.270 | 1.00 | 35.00 | R1 |
| ATOM | 415 | CA | THR | 47 | 68.510 | −7.566 | 12.146 | 1.00 | 34.50 | R1 |
| ATOM | 416 | CB | THR | 47 | 67.635 | −8.539 | 11.351 | 1.00 | 36.51 | R1 |
| ATOM | 417 | OG1 | THR | 47 | 67.052 | −9.504 | 12.241 | 1.00 | 41.03 | R1 |
| ATOM | 418 | HG1 | THR | 47 | 66.529 | −9.051 | 12.908 | 1.00 | 35.00 | R1 |
| ATOM | 419 | CG2 | THR | 47 | 68.478 | −9.248 | 10.275 | 1.00 | 36.56 | R1 |
| ATOM | 420 | C | THR | 47 | 69.118 | −6.582 | 11.160 | 1.00 | 26.71 | R1 |
| ATOM | 421 | O | THR | 47 | 68.406 | −6.012 | 10.327 | 1.00 | 25.55 | R1 |
| ATOM | 422 | N | PRO | 48 | 70.420 | −6.303 | 11.306 | 1.00 | 20.05 | R1 |
| ATOM | 423 | CD | PRO | 48 | 71.279 | −7.043 | 12.245 | 1.00 | 18.04 | R1 |
| ATOM | 424 | CA | PRO | 48 | 71.222 | −5.381 | 10.498 | 1.00 | 19.57 | R1 |
| ATOM | 425 | CB | PRO | 48 | 72.612 | −5.530 | 11.110 | 1.00 | 18.50 | R1 |
| ATOM | 426 | CG | PRO | 48 | 72.607 | −6.927 | 11.609 | 1.00 | 17.51 | R1 |
| ATOM | 427 | C | PRO | 48 | 71.263 | −5.446 | 8.958 | 1.00 | 16.66 | R1 |
| ATOM | 428 | O | PRO | 48 | 70.910 | −6.440 | 8.302 | 1.00 | 11.76 | R1 |
| ATOM | 429 | N | VAL | 49 | 71.708 | −4.334 | 8.393 | 1.00 | 15.06 | R1 |
| ATOM | 430 | H | VAL | 49 | 71.968 | −3.602 | 8.989 | 1.00 | 35.00 | R1 |
| ATOM | 431 | CA | VAL | 49 | 71.848 | −4.207 | 6.960 | 1.00 | 14.20 | R1 |
| ATOM | 432 | CB | VAL | 49 | 72.094 | −2.730 | 6.573 | 1.00 | 15.27 | R1 |
| ATOM | 433 | CG1 | VAL | 49 | 71.425 | −1.786 | 7.603 | 1.00 | 8.86 | R1 |
| ATOM | 434 | CG2 | VAL | 49 | 73.582 | −2.439 | 6.428 | 1.00 | 14.40 | R1 |
| ATOM | 435 | C | VAL | 49 | 73.038 | −5.090 | 6.573 | 1.00 | 15.62 | R1 |
| ATOM | 436 | O | VAL | 49 | 73.928 | −5.343 | 7.388 | 1.00 | 16.65 | R1 |
| ATOM | 437 | N | SER | 50 | 73.052 | −5.569 | 5.342 | 1.00 | 13.82 | R1 |
| ATOM | 438 | H | SER | 50 | 72.324 | −5.344 | 4.724 | 1.00 | 35.00 | R1 |
| ATOM | 439 | CA | SER | 50 | 74.130 | −6.426 | 4.900 | 1.00 | 14.23 | R1 |
| ATOM | 440 | CB | SER | 50 | 73.867 | −6.930 | 3.494 | 1.00 | 6.87 | R1 |
| ATOM | 441 | OG | SER | 50 | 74.945 | −7.737 | 3.079 | 1.00 | 2.70 | R1 |
| ATOM | 442 | HG | SER | 50 | 74.817 | −8.005 | 2.167 | 1.00 | 35.00 | R1 |
| ATOM | 443 | C | SER | 50 | 75.534 | −5.817 | 4.965 | 1.00 | 19.88 | R1 |
| ATOM | 444 | O | SER | 50 | 75.738 | −4.625 | 4.749 | 1.00 | 21.62 | R1 |
| ATOM | 445 | N | THR | 51 | 76.502 | −6.664 | 5.287 | 1.00 | 23.89 | R1 |
| ATOM | 446 | H | THR | 51 | 76.279 | −7.596 | 5.485 | 1.00 | 35.00 | R1 |
| ATOM | 447 | CA | THR | 51 | 77.887 | −6.248 | 5.356 | 1.00 | 25.34 | R1 |
| ATOM | 448 | CB | THR | 51 | 78.674 | −7.135 | 6.367 | 1.00 | 25.58 | R1 |
| ATOM | 449 | OG1 | THR | 51 | 78.308 | −8.507 | 6.199 | 1.00 | 27.90 | R1 |
| ATOM | 450 | HG1 | THR | 51 | 78.860 | −9.063 | 6.755 | 1.00 | 35.00 | R1 |
| ATOM | 451 | CG2 | THR | 51 | 78.345 | −6.747 | 7.776 | 1.00 | 24.70 | R1 |
| ATOM | 452 | C | THR | 51 | 78.509 | −6.309 | 3.944 | 1.00 | 25.83 | R1 |
| ATOM | 453 | O | THR | 51 | 79.628 | −5.841 | 3.731 | 1.00 | 26.89 | R1 |
| ATOM | 454 | N | GLU | 52 | 77.749 | −6.823 | 2.971 | 1.00 | 26.35 | R1 |
| ATOM | 455 | H | GLU | 52 | 76.851 | −7.132 | 3.191 | 1.00 | 35.00 | R1 |
| ATOM | 456 | CA | GLU | 52 | 78.226 | −6.941 | 1.587 | 1.00 | 25.62 | R1 |
| ATOM | 457 | CB | GLU | 52 | 77.419 | −7.992 | 0.817 | 1.00 | 30.16 | R1 |
| ATOM | 458 | CG | GLU | 52 | 78.035 | −9.404 | 0.817 | 1.00 | 35.99 | R1 |
| ATOM | 459 | CD | GLU | 52 | 77.987 | −10.087 | 2.182 | 1.00 | 36.50 | R1 |
| ATOM | 460 | OE1 | GLU | 52 | 78.823 | −10.986 | 2.434 | 1.00 | 36.28 | R1 |
| ATOM | 461 | OE2 | GLU | 52 | 77.102 | −9.733 | 2.996 | 1.00 | 41.63 | R1 |
| ATOM | 462 | C | GLU | 52 | 78.274 | −5.661 | 0.762 | 1.00 | 22.43 | R1 |
| ATOM | 463 | O | GLU | 52 | 77.242 | −5.033 | 0.499 | 1.00 | 19.36 | R1 |
| ATOM | 464 | N | GLN | 53 | 79.480 | −5.314 | 0.309 | 1.00 | 21.09 | R1 |
| ATOM | 465 | H | GLN | 53 | 80.253 | −5.873 | 0.536 | 1.00 | 35.00 | R1 |
| ATOM | 466 | CA | GLN | 53 | 79.688 | −4.127 | −0.514 | 1.00 | 19.78 | R1 |
| ATOM | 467 | CB | GLN | 53 | 81.191 | −3.803 | −0.668 | 1.00 | 16.00 | R1 |
| ATOM | 468 | CG | GLN | 53 | 81.962 | −3.520 | 0.640 | 1.00 | 6.65 | R1 |
| ATOM | 469 | CD | GLN | 53 | 83.047 | −2.441 | 0.494 | 1.00 | 4.41 | R1 |
| ATOM | 470 | OE1 | GLN | 53 | 84.236 | −2.726 | 0.426 | 1.00 | 2.03 | R1 |
| ATOM | 471 | NE2 | GLN | 53 | 82.629 | −1.189 | 0.510 | 1.00 | 6.84 | R1 |
| ATOM | 472 | HE21 | GLN | 53 | 81.678 | −1.051 | 0.670 | 1.00 | 35.00 | R1 |
| ATOM | 473 | HE22 | GLN | 53 | 83.273 | −0.461 | 0.365 | 1.00 | 35.00 | R1 |
| ATOM | 474 | C | GLN | 53 | 79.015 | −4.347 | −1.874 | 1.00 | 19.42 | R1 |
| ATOM | 475 | O | GLN | 53 | 78.882 | −3.417 | −2.695 | 1.00 | 20.11 | R1 |
| ATOM | 476 | N | ALA | 54 | 78.577 | −5.591 | −2.086 | 1.00 | 21.23 | R1 |
| ATOM | 477 | H | ALA | 54 | 78.755 | −6.288 | −1.424 | 1.00 | 35.00 | R1 |
| ATOM | 478 | CA | ALA | 54 | 77.865 | −5.998 | −3.301 | 1.00 | 23.39 | R1 |
| ATOM | 479 | CB | ALA | 54 | 78.150 | −7.472 | −3.626 | 1.00 | 23.69 | R1 |
| ATOM | 480 | C | ALA | 54 | 76.360 | −5.785 | −3.118 | 1.00 | 19.41 | R1 |
| ATOM | 481 | O | ALA | 54 | 75.560 | −6.162 | −3.970 | 1.00 | 22.84 | R1 |
| ATOM | 482 | N | SER | 55 | 75.980 | −5.189 | −1.994 | 1.00 | 15.16 | R1 |
| ATOM | 483 | H | SER | 55 | 76.650 | −4.910 | −1.346 | 1.00 | 35.00 | R1 |
| ATOM | 484 | CA | SER | 55 | 74.585 | −4.927 | −1.722 | 1.00 | 9.20 | R1 |
| ATOM | 485 | CB | SER | 55 | 74.234 | −5.326 | −0.311 | 1.00 | 5.23 | R1 |
| ATOM | 486 | OG | SER | 55 | 74.279 | −6.729 | −0.219 | 1.00 | 2.78 | R1 |

TABLE 3-continued

Crystallographic coordinates for the refined co-crystal

| ATOM | 487 | HG | SER | 55 | 74.103 | −6.976 | 0.692 | 1.00 | 35.00 | R1 |
|---|---|---|---|---|---|---|---|---|---|---|
| ATOM | 488 | C | SER | 55 | 74.217 | −3.490 | −1.980 | 1.00 | 6.69 | R1 |
| ATOM | 489 | O | SER | 55 | 74.939 | −2.561 | −1.627 | 1.00 | 3.43 | R1 |
| ATOM | 490 | N | ARG | 56 | 73.087 | −3.312 | −2.643 | 1.00 | 7.03 | R1 |
| ATOM | 491 | H | ARG | 56 | 72.552 | −4.088 | −2.915 | 1.00 | 35.00 | R1 |
| ATOM | 492 | CA | ARG | 56 | 72.648 | −1.985 | −2.963 | 1.00 | 7.63 | R1 |
| ATOM | 493 | CB | ARG | 56 | 71.287 | −2.039 | −3.642 | 1.00 | 2.02 | R1 |
| ATOM | 494 | CG | ARG | 56 | 70.772 | −0.701 | −4.007 | 1.00 | 2.00 | R1 |
| ATOM | 495 | CD | ARG | 56 | 69.459 | −0.824 | −4.662 | 1.00 | 7.04 | R1 |
| ATOM | 496 | NE | ARG | 56 | 68.411 | −1.178 | −3.720 | 1.00 | 11.82 | R1 |
| ATOM | 497 | HE | ARG | 56 | 68.103 | −2.108 | −3.677 | 1.00 | 35.00 | R1 |
| ATOM | 498 | CZ | ARG | 56 | 67.839 | −0.297 | −2.902 | 1.00 | 14.67 | R1 |
| ATOM | 499 | NH1 | ARG | 56 | 68.230 | 0.976 | −2.911 | 1.00 | 12.05 | R1 |
| ATOM | 500 | HH11 | ARG | 56 | 68.952 | 1.283 | −3.531 | 1.00 | 35.00 | R1 |
| ATOM | 501 | HH12 | ARG | 56 | 67.779 | 1.625 | −2.318 | 1.00 | 35.00 | R1 |
| ATOM | 502 | NH2 | ARG | 56 | 66.834 | −0.672 | −2.124 | 1.00 | 13.50 | R1 |
| ATOM | 503 | HH21 | ARG | 56 | 66.504 | −1.614 | −2.140 | 1.00 | 35.00 | R1 |
| ATOM | 504 | HH22 | ARG | 56 | 66.414 | −0.004 | −1.508 | 1.00 | 35.00 | R1 |
| ATOM | 505 | C | ARG | 56 | 72.644 | −1.155 | −1.665 | 1.00 | 7.27 | R1 |
| ATOM | 506 | O | ARG | 56 | 73.184 | −0.046 | −1.615 | 1.00 | 5.50 | R1 |
| ATOM | 507 | N | ILE | 57 | 72.091 | −1.733 | −0.605 | 1.00 | 5.63 | R1 |
| ATOM | 508 | H | ILE | 57 | 71.690 | −2.623 | −0.697 | 1.00 | 35.00 | R1 |
| ATOM | 509 | CA | ILE | 57 | 72.052 | −1.061 | 0.676 | 1.00 | 2.86 | R1 |
| ATOM | 510 | CB | ILE | 57 | 70.633 | −0.961 | 1.228 | 1.00 | 2.01 | R1 |
| ATOM | 511 | CG2 | ILE | 57 | 70.687 | −0.423 | 2.678 | 1.00 | 8.26 | R1 |
| ATOM | 512 | CG1 | ILE | 57 | 69.804 | −0.037 | 0.348 | 1.00 | 2.00 | R1 |
| ATOM | 513 | CD1 | ILE | 57 | 68.457 | 0.319 | 0.901 | 1.00 | 2.00 | R1 |
| ATOM | 514 | C | ILE | 57 | 72.891 | −1.844 | 1.660 | 1.00 | 2.00 | R1 |
| ATOM | 515 | O | ILE | 57 | 72.528 | −2.957 | 2.039 | 1.00 | 2.52 | R1 |
| ATOM | 516 | N | HIS | 58 | 74.007 | −1.272 | 2.081 | 1.00 | 2.00 | R1 |
| ATOM | 517 | H | HIS | 58 | 74.271 | −0.395 | 1.737 | 1.00 | 35.00 | R1 |
| ATOM | 518 | CA | HIS | 58 | 74.858 | −1.963 | 3.025 | 1.00 | 2.00 | R1 |
| ATOM | 519 | CB | HIS | 58 | 75.751 | −2.942 | 2.292 | 1.00 | 2.00 | R1 |
| ATOM | 520 | CG | HIS | 58 | 76.811 | −2.284 | 1.488 | 1.00 | 2.00 | R1 |
| ATOM | 521 | CD2 | HIS | 58 | 76.760 | −1.633 | 0.304 | 1.00 | 3.00 | R1 |
| ATOM | 522 | ND1 | HIS | 58 | 78.107 | −2.187 | 1.926 | 1.00 | 2.00 | R1 |
| ATOM | 523 | HD1 | HIS | 58 | 78.460 | −2.569 | 2.755 | 1.00 | 35.00 | R1 |
| ATOM | 524 | CE1 | HIS | 58 | 78.813 | −1.498 | 1.052 | 1.00 | 3.75 | R1 |
| ATOM | 525 | NE2 | HIS | 58 | 78.019 | −1.148 | 0.056 | 1.00 | 3.59 | R1 |
| ATOM | 526 | HE2 | HIS | 58 | 78.284 | −0.631 | −0.734 | 1.00 | 35.00 | R1 |
| ATOM | 527 | C | HIS | 58 | 75.702 | −1.015 | 3.854 | 1.00 | 3.95 | R1 |
| ATOM | 528 | O | HIS | 58 | 75.660 | 0.202 | 3.665 | 1.00 | 3.63 | R1 |
| ATOM | 529 | N | GLN | 59 | 76.459 | −1.585 | 4.788 | 1.00 | 5.80 | R1 |
| ATOM | 530 | H | GLN | 59 | 76.430 | −2.557 | 4.899 | 1.00 | 35.00 | R1 |
| ATOM | 531 | CA | GLN | 59 | 77.327 | −0.802 | 5.656 | 1.00 | 4.72 | R1 |
| ATOM | 532 | CB | GLN | 59 | 76.910 | −0.958 | 7.100 | 1.00 | 5.35 | R1 |
| ATOM | 533 | CG | GLN | 59 | 77.292 | −2.286 | 7.685 | 1.00 | 4.55 | R1 |
| ATOM | 534 | CD | GLN | 59 | 76.659 | −2.510 | 9.015 | 1.00 | 3.65 | R1 |
| ATOM | 535 | OE1 | GLN | 59 | 76.982 | −1.813 | 10.010 | 1.00 | 3.16 | R1 |
| ATOM | 536 | NE2 | GLN | 59 | 75.741 | −3.486 | 9.066 | 1.00 | 2.00 | R1 |
| ATOM | 537 | HE21 | GLN | 59 | 75.542 | −3.985 | 8.244 | 1.00 | 35.00 | R1 |
| ATOM | 538 | HE22 | GLN | 59 | 75.300 | −3.667 | 9.923 | 1.00 | 35.00 | R1 |
| ATOM | 539 | C | GLN | 59 | 78.747 | −1.281 | 5.511 | 1.00 | 5.46 | R1 |
| ATOM | 540 | O | GLN | 59 | 78.985 | −2.455 | 5.225 | 1.00 | 8.79 | R1 |
| ATOM | 541 | N | HIS | 60 | 79.682 | −0.370 | 5.735 | 1.00 | 2.90 | R1 |
| ATOM | 542 | H | HIS | 60 | 79.398 | 0.532 | 5.992 | 1.00 | 35.00 | R1 |
| ATOM | 543 | CA | HIS | 60 | 81.104 | −0.654 | 5.633 | 1.00 | 2.00 | R1 |
| ATOM | 544 | CB | HIS | 60 | 81.437 | −1.051 | 4.186 | 1.00 | 2.00 | R1 |
| ATOM | 545 | CG | HIS | 60 | 82.806 | −0.659 | 3.736 | 1.00 | 3.77 | R1 |
| ATOM | 546 | CD2 | HIS | 60 | 83.242 | 0.439 | 3.069 | 1.00 | 2.00 | R1 |
| ATOM | 547 | ND1 | HIS | 60 | 83.923 | −1.436 | 3.980 | 1.00 | 4.52 | R1 |
| ATOM | 548 | HD1 | HIS | 60 | 83.931 | −2.304 | 4.435 | 1.00 | 35.00 | R1 |
| ATOM | 549 | CE1 | HIS | 60 | 84.990 | −0.825 | 3.489 | 1.00 | 6.59 | R1 |
| ATOM | 550 | NE2 | HIS | 60 | 84.603 | 0.312 | 2.930 | 1.00 | 3.42 | R1 |
| ATOM | 551 | HE2 | HIS | 60 | 85.188 | 0.947 | 2.465 | 1.00 | 35.00 | R1 |
| ATOM | 552 | C | HIS | 60 | 81.782 | 0.645 | 6.098 | 1.00 | 2.97 | R1 |
| ATOM | 553 | O | HIS | 60 | 81.329 | 1.736 | 5.749 | 1.00 | 2.00 | R1 |
| ATOM | 554 | N | LYS | 61 | 82.836 | 0.517 | 6.913 | 1.00 | 4.70 | R1 |
| ATOM | 555 | H | LYS | 61 | 83.157 | −0.386 | 7.120 | 1.00 | 35.00 | R1 |
| ATOM | 556 | CA | LYS | 61 | 83.527 | 1.670 | 7.508 | 1.00 | 7.55 | R1 |
| ATOM | 557 | CB | LYS | 61 | 84.057 | 2.630 | 6.437 | 1.00 | 12.34 | R1 |
| ATOM | 558 | CG | LYS | 61 | 85.386 | 2.184 | 5.823 | 1.00 | 17.91 | R1 |
| ATOM | 559 | CD | LYS | 61 | 85.969 | 3.224 | 4.869 | 1.00 | 24.93 | R1 |
| ATOM | 560 | CE | LYS | 61 | 86.923 | 4.217 | 5.554 | 1.00 | 28.08 | R1 |
| ATOM | 561 | NZ | LYS | 61 | 86.290 | 5.254 | 6.439 | 1.00 | 32.33 | R1 |
| ATOM | 562 | HZ1 | LYS | 61 | 85.769 | 4.782 | 7.206 | 1.00 | 35.00 | R1 |
| ATOM | 563 | HZ2 | LYS | 61 | 85.636 | 5.846 | 5.888 | 1.00 | 35.00 | R1 |

TABLE 3-continued

Crystallographic coordinates for the refined co-crystal

| ATOM | 564 | HZ3 | LYS | 61 | 87.036 | 5.853 | 6.848 | 1.00 | 35.00 | R1 |
|---|---|---|---|---|---|---|---|---|---|---|
| ATOM | 565 | C | LYS | 61 | 82.528 | 2.385 | 8.438 | 1.00 | 8.07 | R1 |
| ATOM | 566 | O | LYS | 61 | 82.427 | 3.615 | 8.446 | 1.00 | 2.00 | R1 |
| ATOM | 567 | N | GLU | 62 | 81.798 | 1.578 | 9.222 | 1.00 | 8.27 | R1 |
| ATOM | 568 | H | GLU | 62 | 81.960 | 0.613 | 9.167 | 1.00 | 35.00 | R1 |
| ATOM | 569 | CA | GLU | 62 | 80.776 | 2.047 | 10.152 | 1.00 | 9.64 | R1 |
| ATOM | 570 | CB | GLU | 62 | 81.386 | 2.422 | 11.494 | 1.00 | 8.56 | R1 |
| ATOM | 571 | CG | GLU | 62 | 82.323 | 3.607 | 11.480 | 1.00 | 11.02 | R1 |
| ATOM | 572 | CD | GLU | 62 | 83.517 | 3.376 | 12.389 | 1.00 | 12.11 | R1 |
| ATOM | 573 | OE1 | GLU | 62 | 84.540 | 4.091 | 12.254 | 1.00 | 9.59 | R1 |
| ATOM | 574 | OE2 | GLU | 62 | 83.425 | 2.449 | 13.226 | 1.00 | 12.78 | R1 |
| ATOM | 575 | C | GLU | 62 | 79.947 | 3.190 | 9.569 | 1.00 | 8.30 | R1 |
| ATOM | 576 | O | GLU | 62 | 79.587 | 4.162 | 10.255 | 1.00 | 5.20 | R1 |
| ATOM | 577 | N | LYS | 63 | 79.633 | 3.021 | 8.287 | 1.00 | 6.58 | R1 |
| ATOM | 578 | H | LYS | 63 | 79.929 | 2.197 | 7.848 | 1.00 | 35.00 | R1 |
| ATOM | 579 | CA | LYS | 63 | 78.853 | 3.976 | 7.515 | 1.00 | 8.97 | R1 |
| ATOM | 580 | CB | LYS | 63 | 79.768 | 4.788 | 6.595 | 1.00 | 6.84 | R1 |
| ATOM | 581 | CG | LYS | 63 | 79.626 | 6.269 | 6.789 | 1.00 | 7.36 | R1 |
| ATOM | 582 | CD | LYS | 63 | 80.714 | 7.055 | 6.086 | 1.00 | 9.35 | R1 |
| ATOM | 583 | CE | LYS | 63 | 82.002 | 7.134 | 6.887 | 1.00 | 8.18 | R1 |
| ATOM | 584 | NZ | LYS | 63 | 82.617 | 5.803 | 7.121 | 1.00 | 14.41 | R1 |
| ATOM | 585 | HZ1 | LYS | 63 | 82.789 | 5.304 | 6.226 | 1.00 | 35.00 | R1 |
| ATOM | 586 | HZ2 | LYS | 63 | 81.948 | 5.260 | 7.702 | 1.00 | 35.00 | R1 |
| ATOM | 587 | HZ3 | LYS | 63 | 83.507 | 5.919 | 7.647 | 1.00 | 35.00 | R1 |
| ATOM | 588 | C | LYS | 63 | 77.766 | 3.274 | 6.691 | 1.00 | 6.31 | R1 |
| ATOM | 589 | O | LYS | 63 | 77.902 | 2.098 | 6.332 | 1.00 | 2.71 | R1 |
| ATOM | 590 | N | LEU | 64 | 76.664 | 3.995 | 6.472 | 1.00 | 5.53 | R1 |
| ATOM | 591 | H | LEU | 64 | 76.616 | 4.881 | 6.850 | 1.00 | 35.00 | R1 |
| ATOM | 592 | CA | LEU | 64 | 75.524 | 3.507 | 5.704 | 1.00 | 5.37 | R1 |
| ATOM | 593 | CB | LEU | 64 | 74.221 | 4.074 | 6.265 | 1.00 | 2.00 | R1 |
| ATOM | 594 | CG | LEU | 64 | 73.016 | 3.139 | 6.323 | 1.00 | 2.00 | R1 |
| ATOM | 595 | CD1 | LEU | 64 | 71.804 | 3.786 | 5.759 | 1.00 | 2.00 | R1 |
| ATOM | 596 | CD2 | LEU | 64 | 73.299 | 1.817 | 5.683 | 1.00 | 2.00 | R1 |
| ATOM | 597 | C | LEU | 64 | 75.657 | 3.882 | 4.223 | 1.00 | 2.00 | R1 |
| ATOM | 598 | O | LEU | 64 | 75.619 | 5.056 | 3.837 | 1.00 | 2.00 | R1 |
| ATOM | 599 | N | TRP | 65 | 75.771 | 2.849 | 3.401 | 1.00 | 2.00 | R1 |
| ATOM | 600 | H | TRP | 65 | 75.765 | 1.983 | 3.825 | 1.00 | 35.00 | R1 |
| ATOM | 601 | CA | TRP | 65 | 75.914 | 3.025 | 1.957 | 1.00 | 4.18 | R1 |
| ATOM | 602 | CB | TRP | 65 | 77.134 | 2.247 | 1.467 | 1.00 | 2.38 | R1 |
| ATOM | 603 | CG | TRP | 65 | 78.484 | 2.693 | 1.997 | 1.00 | 3.57 | R1 |
| ATOM | 604 | CD2 | TRP | 65 | 79.406 | 3.604 | 1.364 | 1.00 | 3.16 | R1 |
| ATOM | 605 | CE2 | TRP | 65 | 80.599 | 3.602 | 2.140 | 1.00 | 2.00 | R1 |
| ATOM | 606 | CE3 | TRP | 65 | 79.347 | 4.405 | 0.209 | 1.00 | 2.50 | R1 |
| ATOM | 607 | CD1 | TRP | 65 | 79.135 | 2.206 | 3.108 | 1.00 | 4.44 | R1 |
| ATOM | 608 | NE1 | TRP | 65 | 80.401 | 2.749 | 3.190 | 1.00 | 3.61 | R1 |
| ATOM | 609 | HE1 | TRP | 65 | 81.062 | 2.553 | 3.886 | 1.00 | 35.00 | R1 |
| ATOM | 610 | CZ2 | TRP | 65 | 81.715 | 4.360 | 1.803 | 1.00 | 2.00 | R1 |
| ATOM | 611 | CZ3 | TRP | 65 | 80.463 | 5.169 | −0.134 | 1.00 | 2.82 | R1 |
| ATOM | 612 | CH2 | TRP | 65 | 81.638 | 5.138 | 0.667 | 1.00 | 3.59 | R1 |
| ATOM | 613 | C | TRP | 65 | 74.693 | 2.640 | 1.090 | 1.00 | 2.00 | R1 |
| ATOM | 614 | O | TRP | 65 | 74.218 | 1.527 | 1.138 | 1.00 | 2.00 | R1 |
| ATOM | 615 | N | PHE | 66 | 74.119 | 3.610 | 0.396 | 1.00 | 2.12 | R1 |
| ATOM | 616 | H | PHE | 66 | 74.429 | 4.529 | 0.523 | 1.00 | 35.00 | R1 |
| ATOM | 617 | CA | PHE | 66 | 73.015 | 3.347 | −0.545 | 1.00 | 6.29 | R1 |
| ATOM | 618 | CB | PHE | 66 | 71.884 | 4.375 | −0.420 | 1.00 | 2.00 | R1 |
| ATOM | 619 | CG | PHE | 66 | 71.384 | 4.552 | 0.947 | 1.00 | 3.83 | R1 |
| ATOM | 620 | CD1 | PHE | 66 | 72.044 | 5.395 | 1.835 | 1.00 | 4.72 | R1 |
| ATOM | 621 | CD2 | PHE | 66 | 70.208 | 3.953 | 1.342 | 1.00 | 2.54 | R1 |
| ATOM | 622 | CE1 | PHE | 66 | 71.521 | 5.643 | 3.090 | 1.00 | 3.15 | R1 |
| ATOM | 623 | CE2 | PHE | 66 | 69.683 | 4.195 | 2.599 | 1.00 | 2.40 | R1 |
| ATOM | 624 | CZ | PHE | 66 | 70.333 | 5.040 | 3.468 | 1.00 | 2.00 | R1 |
| ATOM | 625 | C | PHE | 66 | 73.701 | 3.543 | −1.920 | 1.00 | 8.85 | R1 |
| ATOM | 626 | O | PHE | 66 | 73.847 | 4.683 | −2.391 | 1.00 | 7.34 | R1 |
| ATOM | 627 | N | VAL | 67 | 74.119 | 2.460 | −2.566 | 1.00 | 10.13 | R1 |
| ATOM | 628 | H | VAL | 67 | 73.953 | 1.571 | −2.210 | 1.00 | 35.00 | R1 |
| ATOM | 629 | CA | VAL | 67 | 74.838 | 2.631 | −3.808 | 1.00 | 18.99 | R1 |
| ATOM | 630 | CB | VAL | 67 | 75.650 | 1.375 | −4.122 | 1.00 | 20.00 | R1 |
| ATOM | 631 | CG1 | VAL | 67 | 76.539 | 1.587 | −5.315 | 1.00 | 22.22 | R1 |
| ATOM | 632 | CG2 | VAL | 67 | 76.534 | 1.067 | −2.911 | 1.00 | 16.83 | R1 |
| ATOM | 633 | C | VAL | 67 | 73.993 | 3.278 | −4.933 | 1.00 | 22.33 | R1 |
| ATOM | 634 | O | VAL | 67 | 74.227 | 4.445 | −5.292 | 1.00 | 26.48 | R1 |
| ATOM | 635 | N | PRO | 68 | 73.065 | 2.546 | −5.551 | 1.00 | 21.04 | R1 |
| ATOM | 636 | CD | PRO | 68 | 72.972 | 1.108 | −5.845 | 1.00 | 19.45 | R1 |
| ATOM | 637 | CA | PRO | 68 | 72.355 | 3.347 | −6.555 | 1.00 | 17.85 | R1 |
| ATOM | 638 | CB | PRO | 68 | 71.565 | 2.309 | −7.325 | 1.00 | 16.06 | R1 |
| ATOM | 639 | CG | PRO | 68 | 72.459 | 1.109 | −7.266 | 1.00 | 22.20 | R1 |
| ATOM | 640 | C | PRO | 68 | 71.417 | 4.340 | −5.837 | 1.00 | 20.05 | R1 |

TABLE 3-continued

Crystallographic coordinates for the refined co-crystal

| ATOM | 641 | O | PRO | 68 | 71.093 | 5.390 | −6.390 | 1.00 | 24.26 | R1 |
|---|---|---|---|---|---|---|---|---|---|---|
| ATOM | 642 | N | ALA | 69 | 71.019 | 4.016 | −4.599 | 1.00 | 18.46 | R1 |
| ATOM | 643 | H | ALA | 69 | 71.344 | 3.176 | −4.215 | 1.00 | 35.00 | R1 |
| ATOM | 644 | CA | ALA | 69 | 70.104 | 4.846 | −3.775 | 1.00 | 19.70 | R1 |
| ATOM | 645 | CB | ALA | 69 | 70.721 | 6.171 | −3.411 | 1.00 | 21.35 | R1 |
| ATOM | 646 | C | ALA | 69 | 68.734 | 5.080 | −4.382 | 1.00 | 18.07 | R1 |
| ATOM | 647 | O | ALA | 69 | 68.561 | 5.948 | −5.237 | 1.00 | 18.94 | R1 |
| ATOM | 648 | N | LYS | 70 | 67.749 | 4.354 | −3.866 | 1.00 | 17.67 | R1 |
| ATOM | 649 | H | LYS | 70 | 67.949 | 3.738 | −3.129 | 1.00 | 35.00 | R1 |
| ATOM | 650 | CA | LYS | 70 | 66.388 | 4.426 | −4.362 | 1.00 | 15.54 | R1 |
| ATOM | 651 | CB | LYS | 70 | 65.829 | 3.008 | −4.461 | 1.00 | 17.18 | R1 |
| ATOM | 652 | CG | LYS | 70 | 66.369 | 2.210 | −5.658 | 1.00 | 20.79 | R1 |
| ATOM | 653 | CD | LYS | 70 | 65.782 | 2.723 | −6.981 | 1.00 | 22.79 | R1 |
| ATOM | 654 | CE | LYS | 70 | 64.249 | 2.413 | −7.143 | 1.00 | 24.43 | R1 |
| ATOM | 655 | NZ | LYS | 70 | 63.861 | 0.982 | −7.470 | 1.00 | 21.19 | R1 |
| ATOM | 656 | HZ1 | LYS | 70 | 64.291 | 0.704 | −8.376 | 1.00 | 35.00 | R1 |
| ATOM | 657 | HZ2 | LYS | 70 | 62.826 | 0.954 | −7.555 | 1.00 | 35.00 | R1 |
| ATOM | 658 | HZ3 | LYS | 70 | 64.176 | 0.343 | −6.715 | 1.00 | 35.00 | R1 |
| ATOM | 659 | C | LYS | 70 | 65.449 | 5.303 | −3.557 | 1.00 | 11.70 | R1 |
| ATOM | 660 | O | LYS | 70 | 65.736 | 5.641 | −2.421 | 1.00 | 13.88 | R1 |
| ATOM | 661 | N | VAL | 71 | 64.349 | 5.707 | −4.192 | 1.00 | 11.44 | R1 |
| ATOM | 662 | H | VAL | 71 | 64.242 | 5.433 | −5.126 | 1.00 | 35.00 | R1 |
| ATOM | 663 | CA | VAL | 71 | 63.291 | 6.530 | −3.581 | 1.00 | 11.03 | R1 |
| ATOM | 664 | CB | VAL | 71 | 62.230 | 6.879 | −4.605 | 1.00 | 6.21 | R1 |
| ATOM | 665 | CG1 | VAL | 71 | 61.070 | 7.585 | −3.925 | 1.00 | 5.49 | R1 |
| ATOM | 666 | CG2 | VAL | 71 | 62.825 | 7.695 | −5.698 | 1.00 | 2.00 | R1 |
| ATOM | 667 | C | VAL | 71 | 62.554 | 5.800 | −2.465 | 1.00 | 7.27 | R1 |
| ATOM | 668 | O | VAL | 71 | 62.171 | 6.401 | −1.477 | 1.00 | 2.51 | R1 |
| ATOM | 669 | N | GLU | 72 | 62.300 | 4.516 | −2.703 | 1.00 | 10.44 | R1 |
| ATOM | 670 | H | GLU | 72 | 62.575 | 4.153 | −3.571 | 1.00 | 35.00 | R1 |
| ATOM | 671 | CA | GLU | 72 | 61.638 | 3.623 | −1.764 | 1.00 | 16.75 | R1 |
| ATOM | 672 | CB | GLU | 72 | 61.098 | 2.387 | −2.501 | 1.00 | 24.12 | R1 |
| ATOM | 673 | CG | GLU | 72 | 60.370 | 2.687 | −3.819 | 1.00 | 35.11 | R1 |
| ATOM | 674 | CD | GLU | 72 | 61.014 | 2.012 | −5.035 | 1.00 | 38.79 | R1 |
| ATOM | 675 | OE1 | GLU | 72 | 61.663 | 0.948 | −4.861 | 1.00 | 41.28 | R1 |
| ATOM | 676 | OE2 | GLU | 72 | 60.862 | 2.543 | −6.166 | 1.00 | 41.40 | R1 |
| ATOM | 677 | C | GLU | 72 | 62.650 | 3.179 | −0.697 | 1.00 | 15.01 | R1 |
| ATOM | 678 | O | GLU | 72 | 62.653 | 2.023 | −0.257 | 1.00 | 16.24 | R1 |
| ATOM | 679 | N | ASP | 73 | 63.594 | 4.064 | −0.405 | 1.00 | 10.14 | R1 |
| ATOM | 680 | H | ASP | 73 | 63.669 | 4.913 | −0.863 | 1.00 | 35.00 | R1 |
| ATOM | 681 | CA | ASP | 73 | 64.606 | 3.843 | 0.604 | 1.00 | 7.09 | R1 |
| ATOM | 682 | CB | ASP | 73 | 66.005 | 4.044 | 0.042 | 1.00 | 3.00 | R1 |
| ATOM | 683 | CG | ASP | 73 | 66.579 | 2.802 | −0.551 | 1.00 | 5.21 | R1 |
| ATOM | 684 | OD1 | ASP | 73 | 65.909 | 1.751 | −0.529 | 1.00 | 12.38 | R1 |
| ATOM | 685 | OD2 | ASP | 73 | 67.724 | 2.865 | −1.034 | 1.00 | 6.57 | R1 |
| ATOM | 686 | C | ASP | 73 | 64.361 | 4.937 | 1.615 | 1.00 | 8.29 | R1 |
| ATOM | 687 | O | ASP | 73 | 64.878 | 4.891 | 2.736 | 1.00 | 12.10 | R1 |
| ATOM | 688 | N | SER | 74 | 63.614 | 5.954 | 1.194 | 1.00 | 4.15 | R1 |
| ATOM | 689 | H | SER | 74 | 63.259 | 5.957 | 0.282 | 1.00 | 35.00 | R1 |
| ATOM | 690 | CA | SER | 74 | 63.327 | 7.065 | 2.061 | 1.00 | 6.54 | R1 |
| ATOM | 691 | CB | SER | 74 | 62.373 | 8.011 | 1.354 | 1.00 | 3.30 | R1 |
| ATOM | 692 | OG | SER | 74 | 62.952 | 8.411 | 0.124 | 1.00 | 2.00 | R1 |
| ATOM | 693 | HG | SER | 74 | 62.312 | 8.917 | −0.380 | 1.00 | 35.00 | R1 |
| ATOM | 694 | C | SER | 74 | 62.765 | 6.575 | 3.391 | 1.00 | 7.77 | R1 |
| ATOM | 695 | O | SER | 74 | 61.729 | 5.918 | 3.426 | 1.00 | 12.11 | R1 |
| ATOM | 696 | N | GLY | 75 | 63.503 | 6.798 | 4.473 | 1.00 | 7.72 | R1 |
| ATOM | 697 | H | GLY | 75 | 64.376 | 7.232 | 4.397 | 1.00 | 35.00 | R1 |
| ATOM | 698 | CA | GLY | 75 | 63.015 | 6.364 | 5.765 | 1.00 | 12.62 | R1 |
| ATOM | 699 | C | GLY | 75 | 63.915 | 6.505 | 6.982 | 1.00 | 16.70 | R1 |
| ATOM | 700 | O | GLY | 75 | 65.013 | 7.055 | 6.937 | 1.00 | 12.87 | R1 |
| ATOM | 701 | N | HIS | 76 | 63.437 | 5.943 | 8.083 | 1.00 | 20.74 | R1 |
| ATOM | 702 | H | HIS | 76 | 62.575 | 5.480 | 8.037 | 1.00 | 35.00 | R1 |
| ATOM | 703 | CA | HIS | 76 | 64.141 | 5.990 | 9.352 | 1.00 | 25.86 | R1 |
| ATOM | 704 | CB | HIS | 76 | 63.151 | 5.785 | 10.503 | 1.00 | 26.59 | R1 |
| ATOM | 705 | CG | HIS | 76 | 61.919 | 6.629 | 10.393 | 1.00 | 28.60 | R1 |
| ATOM | 706 | CD2 | HIS | 76 | 61.765 | 7.961 | 10.196 | 1.00 | 28.62 | R1 |
| ATOM | 707 | ND1 | HIS | 76 | 60.647 | 6.106 | 10.478 | 1.00 | 28.75 | R1 |
| ATOM | 708 | HD1 | HIS | 76 | 60.422 | 5.161 | 10.601 | 1.00 | 35.00 | R1 |
| ATOM | 709 | CE1 | HIS | 76 | 59.763 | 7.078 | 10.344 | 1.00 | 28.82 | R1 |
| ATOM | 710 | NE2 | HIS | 76 | 60.417 | 8.214 | 10.172 | 1.00 | 30.19 | R1 |
| ATOM | 711 | HE2 | HIS | 76 | 60.006 | 9.095 | 10.046 | 1.00 | 35.00 | R1 |
| ATOM | 712 | C | HIS | 76 | 65.200 | 4.922 | 9.410 | 1.00 | 24.45 | R1 |
| ATOM | 713 | O | HIS | 76 | 64.937 | 3.767 | 9.085 | 1.00 | 26.75 | R1 |
| ATOM | 714 | N | TYR | 77 | 66.409 | 5.313 | 9.788 | 1.00 | 23.79 | R1 |
| ATOM | 715 | H | TYR | 77 | 66.581 | 6.260 | 9.972 | 1.00 | 35.00 | R1 |
| ATOM | 716 | CA | TYR | 77 | 67.501 | 4.351 | 9.921 | 1.00 | 18.96 | R1 |
| ATOM | 717 | CB | TYR | 77 | 68.538 | 4.534 | 8.802 | 1.00 | 16.87 | R1 |

TABLE 3-continued

Crystallographic coordinates for the refined co-crystal

| ATOM | 718 | CG | TYR | 77 | 68.073 | 4.114 | 7.430 | 1.00 | 14.33 | R1 |
|---|---|---|---|---|---|---|---|---|---|---|
| ATOM | 719 | CD1 | TYR | 77 | 68.391 | 2.864 | 6.920 | 1.00 | 12.86 | R1 |
| ATOM | 720 | CE1 | TYR | 77 | 67.960 | 2.477 | 5.667 | 1.00 | 12.88 | R1 |
| ATOM | 721 | CD2 | TYR | 77 | 67.309 | 4.972 | 6.643 | 1.00 | 15.72 | R1 |
| ATOM | 722 | CE2 | TYR | 77 | 66.873 | 4.604 | 5.386 | 1.00 | 12.01 | R1 |
| ATOM | 723 | CZ | TYR | 77 | 67.200 | 3.354 | 4.899 | 1.00 | 15.67 | R1 |
| ATOM | 724 | OH | TYR | 77 | 66.788 | 3.002 | 3.627 | 1.00 | 12.17 | R1 |
| ATOM | 725 | HH | TYR | 77 | 67.026 | 2.089 | 3.451 | 1.00 | 35.00 | R1 |
| ATOM | 726 | C | TYR | 77 | 68.150 | 4.478 | 11.316 | 1.00 | 17.44 | R1 |
| ATOM | 727 | O | TYR | 77 | 68.226 | 5.567 | 11.903 | 1.00 | 12.98 | R1 |
| ATOM | 728 | N | TYR | 78 | 68.604 | 3.346 | 11.836 | 1.00 | 15.47 | R1 |
| ATOM | 729 | H | TYR | 78 | 68.501 | 2.521 | 11.322 | 1.00 | 35.00 | R1 |
| ATOM | 730 | CA | TYR | 78 | 69.222 | 3.286 | 13.143 | 1.00 | 15.26 | R1 |
| ATOM | 731 | CB | TYR | 78 | 68.446 | 2.336 | 14.046 | 1.00 | 18.57 | R1 |
| ATOM | 732 | CG | TYR | 78 | 67.046 | 2.789 | 14.375 | 1.00 | 20.57 | R1 |
| ATOM | 733 | CD1 | TYR | 78 | 66.819 | 3.742 | 15.362 | 1.00 | 22.39 | R1 |
| ATOM | 734 | CE1 | TYR | 78 | 65.531 | 4.110 | 15.722 | 1.00 | 24.57 | R1 |
| ATOM | 735 | CD2 | TYR | 78 | 65.945 | 2.219 | 13.745 | 1.00 | 20.87 | R1 |
| ATOM | 736 | CE2 | TYR | 78 | 64.655 | 2.580 | 14.099 | 1.00 | 23.85 | R1 |
| ATOM | 737 | CZ | TYR | 78 | 64.456 | 3.524 | 15.091 | 1.00 | 24.10 | R1 |
| ATOM | 738 | OH | TYR | 78 | 63.180 | 3.864 | 15.475 | 1.00 | 25.81 | R1 |
| ATOM | 739 | HH | TYR | 78 | 62.541 | 3.381 | 14.949 | 1.00 | 35.00 | R1 |
| ATOM | 740 | C | TYR | 78 | 70.698 | 2.914 | 13.146 | 1.00 | 16.09 | R1 |
| ATOM | 741 | O | TYR | 78 | 71.146 | 1.977 | 12.493 | 1.00 | 14.08 | R1 |
| ATOM | 742 | N | CYS | 79 | 71.419 | 3.612 | 14.005 | 1.00 | 16.44 | R1 |
| ATOM | 743 | H | CYS | 79 | 70.963 | 4.270 | 14.569 | 1.00 | 35.00 | R1 |
| ATOM | 744 | CA | CYS | 79 | 72.840 | 3.462 | 14.164 | 1.00 | 15.44 | R1 |
| ATOM | 745 | C | CYS | 79 | 73.137 | 3.113 | 15.639 | 1.00 | 17.55 | R1 |
| ATOM | 746 | O | CYS | 79 | 72.673 | 3.811 | 16.536 | 1.00 | 19.95 | R1 |
| ATOM | 747 | CB | CYS | 79 | 73.443 | 4.794 | 13.784 | 1.00 | 10.58 | R1 |
| ATOM | 748 | SG | CYS | 79 | 75.211 | 4.641 | 13.767 | 1.00 | 19.36 | R1 |
| ATOM | 749 | N | VAL | 80 | 73.927 | 2.069 | 15.901 | 1.00 | 16.02 | R1 |
| ATOM | 750 | H | VAL | 80 | 74.357 | 1.596 | 15.178 | 1.00 | 35.00 | R1 |
| ATOM | 751 | CA | VAL | 80 | 74.187 | 1.657 | 17.288 | 1.00 | 18.86 | R1 |
| ATOM | 752 | CB | VAL | 80 | 73.403 | 0.346 | 17.617 | 1.00 | 14.12 | R1 |
| ATOM | 753 | CG1 | VAL | 80 | 73.646 | −0.098 | 19.035 | 1.00 | 16.17 | R1 |
| ATOM | 754 | CG2 | VAL | 80 | 71.940 | 0.555 | 17.426 | 1.00 | 14.55 | R1 |
| ATOM | 755 | C | VAL | 80 | 75.654 | 1.483 | 17.707 | 1.00 | 18.04 | R1 |
| ATOM | 756 | O | VAL | 80 | 76.400 | 0.721 | 17.087 | 1.00 | 18.35 | R1 |
| ATOM | 757 | N | VAL | 81 | 76.043 | 2.136 | 18.803 | 1.00 | 19.22 | R1 |
| ATOM | 758 | H | VAL | 81 | 75.412 | 2.687 | 19.294 | 1.00 | 35.00 | R1 |
| ATOM | 759 | CA | VAL | 81 | 77.418 | 2.039 | 19.302 | 1.00 | 25.34 | R1 |
| ATOM | 760 | CB | VAL | 81 | 78.023 | 3.430 | 19.546 | 1.00 | 21.81 | R1 |
| ATOM | 761 | CG1 | VAL | 81 | 79.482 | 3.304 | 19.845 | 1.00 | 22.54 | R1 |
| ATOM | 762 | CG2 | VAL | 81 | 77.838 | 4.298 | 18.356 | 1.00 | 22.97 | R1 |
| ATOM | 763 | C | VAL | 81 | 77.477 | 1.243 | 20.615 | 1.00 | 26.08 | R1 |
| ATOM | 764 | O | VAL | 81 | 77.282 | 1.808 | 21.686 | 1.00 | 24.10 | R1 |
| ATOM | 765 | N | ARG | 82 | 77.793 | −0.050 | 20.538 | 1.00 | 30.02 | R1 |
| ATOM | 766 | H | ARG | 82 | 78.001 | −0.449 | 19.668 | 1.00 | 35.00 | R1 |
| ATOM | 767 | CA | ARG | 82 | 77.839 | −0.881 | 21.738 | 1.00 | 35.60 | R1 |
| ATOM | 768 | CB | ARG | 82 | 77.218 | −2.258 | 21.493 | 1.00 | 35.39 | R1 |
| ATOM | 769 | CG | ARG | 82 | 75.730 | −2.231 | 21.220 | 1.00 | 34.66 | R1 |
| ATOM | 770 | CD | ARG | 82 | 75.117 | −3.626 | 21.286 | 1.00 | 38.29 | R1 |
| ATOM | 771 | NE | ARG | 82 | 73.828 | −3.654 | 20.601 | 1.00 | 39.20 | R1 |
| ATOM | 772 | HE | ARG | 82 | 73.016 | −3.590 | 21.145 | 1.00 | 35.00 | R1 |
| ATOM | 773 | CZ | ARG | 82 | 73.687 | −3.759 | 19.280 | 1.00 | 38.86 | R1 |
| ATOM | 774 | NH1 | ARG | 82 | 74.759 | −3.869 | 18.504 | 1.00 | 34.86 | R1 |
| ATOM | 775 | HH11 | ARG | 82 | 75.675 | −3.878 | 18.906 | 1.00 | 35.00 | R1 |
| ATOM | 776 | HH12 | ARG | 82 | 74.651 | −3.952 | 17.514 | 1.00 | 35.00 | R1 |
| ATOM | 777 | NH2 | ARG | 82 | 72.484 | −3.649 | 18.728 | 1.00 | 33.80 | R1 |
| ATOM | 778 | HH21 | ARG | 82 | 71.684 | −3.489 | 19.305 | 1.00 | 35.00 | R1 |
| ATOM | 779 | HH22 | ARG | 82 | 72.383 | −3.731 | 17.736 | 1.00 | 35.00 | R1 |
| ATOM | 780 | C | ARG | 82 | 79.177 | −1.036 | 22.447 | 1.00 | 39.37 | R1 |
| ATOM | 781 | O | ARG | 82 | 80.240 | −1.082 | 21.827 | 1.00 | 39.94 | R1 |
| ATOM | 782 | N | ASN | 83 | 79.076 | −1.198 | 23.763 | 1.00 | 42.62 | R1 |
| ATOM | 783 | H | ASN | 83 | 78.179 | −1.239 | 24.155 | 1.00 | 35.00 | R1 |
| ATOM | 784 | CA | ASN | 83 | 80.213 | −1.339 | 24.659 | 1.00 | 45.15 | R1 |
| ATOM | 785 | CB | ASN | 83 | 80.216 | −0.136 | 25.611 | 1.00 | 48.86 | R1 |
| ATOM | 786 | CG | ASN | 83 | 81.600 | 0.253 | 26.078 | 1.00 | 50.59 | R1 |
| ATOM | 787 | OD1 | ASN | 83 | 81.843 | 0.381 | 27.280 | 1.00 | 50.71 | R1 |
| ATOM | 788 | ND2 | ASN | 83 | 82.505 | 0.490 | 25.131 | 1.00 | 52.16 | R1 |
| ATOM | 789 | HD21 | ASN | 83 | 82.233 | 0.399 | 24.194 | 1.00 | 35.00 | R1 |
| ATOM | 790 | HD22 | ASN | 83 | 83.411 | 0.742 | 25.409 | 1.00 | 35.00 | R1 |
| ATOM | 791 | C | ASN | 83 | 79.990 | −2.616 | 25.465 | 1.00 | 44.67 | R1 |
| ATOM | 792 | O | ASN | 83 | 79.208 | −3.481 | 25.072 | 1.00 | 44.88 | R1 |
| ATOM | 793 | N | SER | 84 | 80.706 | −2.737 | 26.576 | 1.00 | 44.27 | R1 |
| ATOM | 794 | H | SER | 84 | 81.353 | −2.046 | 26.823 | 1.00 | 35.00 | R1 |

TABLE 3-continued

Crystallographic coordinates for the refined co-crystal

| ATOM | 795 | CA | SER | 84 | 80.578 | −3.882 | 27.476 | 1.00 | 44.32 | R1 |
|---|---|---|---|---|---|---|---|---|---|---|
| ATOM | 796 | CB | SER | 84 | 81.943 | −4.254 | 28.066 | 1.00 | 43.85 | R1 |
| ATOM | 797 | OG | SER | 84 | 82.914 | −4.453 | 27.047 | 1.00 | 45.20 | R1 |
| ATOM | 798 | HG | SER | 84 | 83.746 | −4.681 | 27.469 | 1.00 | 35.00 | R1 |
| ATOM | 799 | C | SER | 84 | 79.640 | −3.436 | 28.592 | 1.00 | 41.25 | R1 |
| ATOM | 800 | O | SER | 84 | 79.216 | −4.225 | 29.434 | 1.00 | 39.45 | R1 |
| ATOM | 801 | N | SER | 85 | 79.330 | −2.144 | 28.579 | 1.00 | 40.92 | R1 |
| ATOM | 802 | H | SER | 85 | 79.715 | −1.554 | 27.900 | 1.00 | 35.00 | R1 |
| ATOM | 803 | CA | SER | 85 | 78.450 | −1.540 | 29.559 | 1.00 | 39.40 | R1 |
| ATOM | 804 | CB | SER | 85 | 79.246 | −0.622 | 30.506 | 1.00 | 43.57 | R1 |
| ATOM | 805 | OG | SER | 85 | 80.079 | 0.291 | 29.804 | 1.00 | 46.58 | R1 |
| ATOM | 806 | HG | SER | 85 | 80.529 | 0.847 | 30.445 | 1.00 | 35.00 | R1 |
| ATOM | 807 | C | SER | 85 | 77.296 | −0.776 | 28.923 | 1.00 | 36.80 | R1 |
| ATOM | 808 | O | SER | 85 | 76.140 | −1.086 | 29.191 | 1.00 | 34.51 | R1 |
| ATOM | 809 | N | TYR | 86 | 77.601 | 0.174 | 28.039 | 1.00 | 34.96 | R1 |
| ATOM | 810 | H | TYR | 86 | 78.539 | 0.327 | 27.801 | 1.00 | 35.00 | R1 |
| ATOM | 811 | CA | TYR | 86 | 76.549 | 0.979 | 27.415 | 1.00 | 35.62 | R1 |
| ATOM | 812 | CB | TYR | 86 | 76.746 | 2.459 | 27.766 | 1.00 | 41.04 | R1 |
| ATOM | 813 | CG | TYR | 86 | 77.965 | 3.107 | 27.141 | 1.00 | 46.92 | R1 |
| ATOM | 814 | CD1 | TYR | 86 | 77.829 | 3.994 | 26.075 | 1.00 | 48.93 | R1 |
| ATOM | 815 | CE1 | TYR | 86 | 78.937 | 4.619 | 25.506 | 1.00 | 53.35 | R1 |
| ATOM | 816 | CD2 | TYR | 86 | 79.252 | 2.853 | 27.631 | 1.00 | 48.68 | R1 |
| ATOM | 817 | CE2 | TYR | 86 | 80.371 | 3.471 | 27.073 | 1.00 | 52.46 | R1 |
| ATOM | 818 | CZ | TYR | 86 | 80.207 | 4.357 | 26.005 | 1.00 | 54.50 | R1 |
| ATOM | 819 | OH | TYR | 86 | 81.302 | 4.979 | 25.423 | 1.00 | 58.92 | R1 |
| ATOM | 820 | HH | TYR | 86 | 82.104 | 4.685 | 25.862 | 1.00 | 35.00 | R1 |
| ATOM | 821 | C | TYR | 86 | 76.327 | 0.828 | 25.906 | 1.00 | 30.32 | R1 |
| ATOM | 822 | O | TYR | 86 | 77.071 | 0.127 | 25.220 | 1.00 | 29.77 | R1 |
| ATOM | 823 | N | CYS | 87 | 75.241 | 1.436 | 25.421 | 1.00 | 25.71 | R1 |
| ATOM | 824 | H | CYS | 87 | 74.650 | 1.914 | 26.038 | 1.00 | 35.00 | R1 |
| ATOM | 825 | CA | CYS | 87 | 74.893 | 1.421 | 24.002 | 1.00 | 19.82 | R1 |
| ATOM | 826 | C | CYS | 87 | 73.950 | 2.505 | 23.546 | 1.00 | 13.43 | R1 |
| ATOM | 827 | O | CYS | 87 | 72.772 | 2.490 | 23.879 | 1.00 | 15.48 | R1 |
| ATOM | 828 | CB | CYS | 87 | 74.361 | 0.067 | 23.520 | 1.00 | 19.72 | R1 |
| ATOM | 829 | SG | CYS | 87 | 72.813 | −0.591 | 24.203 | 1.00 | 22.31 | R1 |
| ATOM | 830 | N | LEU | 88 | 74.485 | 3.426 | 22.756 | 1.00 | 5.95 | R1 |
| ATOM | 831 | H | LEU | 88 | 75.439 | 3.366 | 22.537 | 1.00 | 35.00 | R1 |
| ATOM | 832 | CA | LEU | 88 | 73.718 | 4.518 | 22.189 | 1.00 | 3.15 | R1 |
| ATOM | 833 | CB | LEU | 88 | 74.628 | 5.703 | 21.943 | 1.00 | 4.50 | R1 |
| ATOM | 834 | CG | LEU | 88 | 73.950 | 6.970 | 21.439 | 1.00 | 4.05 | R1 |
| ATOM | 835 | CD1 | LEU | 88 | 73.054 | 7.596 | 22.523 | 1.00 | 2.00 | R1 |
| ATOM | 836 | CD2 | LEU | 88 | 75.061 | 7.905 | 21.020 | 1.00 | 2.00 | R1 |
| ATOM | 837 | C | LEU | 88 | 73.141 | 4.066 | 20.853 | 1.00 | 2.00 | R1 |
| ATOM | 838 | O | LEU | 88 | 73.834 | 3.466 | 20.039 | 1.00 | 2.00 | R1 |
| ATOM | 839 | N | ARG | 89 | 71.872 | 4.379 | 20.633 | 1.00 | 3.25 | R1 |
| ATOM | 840 | H | ARG | 89 | 71.393 | 4.892 | 21.314 | 1.00 | 35.00 | R1 |
| ATOM | 841 | CA | ARG | 89 | 71.154 | 4.012 | 19.414 | 1.00 | 2.00 | R1 |
| ATOM | 842 | CB | ARG | 89 | 70.037 | 3.022 | 19.764 | 1.00 | 2.00 | R1 |
| ATOM | 843 | CG | ARG | 89 | 69.152 | 2.596 | 18.623 | 1.00 | 4.18 | R1 |
| ATOM | 844 | CD | ARG | 89 | 68.054 | 1.658 | 19.090 | 1.00 | 11.11 | R1 |
| ATOM | 845 | NE | ARG | 89 | 68.480 | 0.257 | 19.109 | 1.00 | 19.61 | R1 |
| ATOM | 846 | HE | ARG | 89 | 69.027 | −0.056 | 18.360 | 1.00 | 35.00 | R1 |
| ATOM | 847 | CZ | ARG | 89 | 68.179 | −0.622 | 20.070 | 1.00 | 22.35 | R1 |
| ATOM | 848 | NH1 | ARG | 89 | 67.455 | −0.254 | 21.130 | 1.00 | 22.76 | R1 |
| ATOM | 849 | HH11 | ARG | 89 | 67.134 | 0.687 | 21.232 | 1.00 | 35.00 | R1 |
| ATOM | 850 | HH12 | ARG | 89 | 67.251 | −0.930 | 21.839 | 1.00 | 35.00 | R1 |
| ATOM | 851 | NH2 | ARG | 89 | 68.527 | −1.902 | 19.926 | 1.00 | 22.65 | R1 |
| ATOM | 852 | HH21 | ARG | 89 | 69.009 | −2.189 | 19.097 | 1.00 | 35.00 | R1 |
| ATOM | 853 | HH22 | ARG | 89 | 68.311 | −2.572 | 20.637 | 1.00 | 35.00 | R1 |
| ATOM | 854 | C | ARG | 89 | 70.576 | 5.287 | 18.808 | 1.00 | 2.00 | R1 |
| ATOM | 855 | O | ARG | 89 | 69.652 | 5.878 | 19.369 | 1.00 | 2.00 | R1 |
| ATOM | 856 | N | ILE | 90 | 71.145 | 5.726 | 17.686 | 1.00 | 2.00 | R1 |
| ATOM | 857 | H | ILE | 90 | 71.918 | 5.274 | 17.323 | 1.00 | 35.00 | R1 |
| ATOM | 858 | CA | ILE | 90 | 70.689 | 6.942 | 17.013 | 1.00 | 2.87 | R1 |
| ATOM | 859 | CB | ILE | 90 | 71.845 | 7.749 | 16.507 | 1.00 | 2.77 | R1 |
| ATOM | 860 | CG2 | ILE | 90 | 71.325 | 8.990 | 15.773 | 1.00 | 3.21 | R1 |
| ATOM | 861 | CG1 | ILE | 90 | 72.751 | 8.111 | 17.667 | 1.00 | 2.00 | R1 |
| ATOM | 862 | CD1 | ILE | 90 | 73.940 | 8.883 | 17.240 | 1.00 | 3.61 | R1 |
| ATOM | 863 | C | ILE | 90 | 69.770 | 6.778 | 15.825 | 1.00 | 2.00 | R1 |
| ATOM | 864 | O | ILE | 90 | 70.167 | 6.214 | 14.838 | 1.00 | 2.00 | R1 |
| ATOM | 865 | N | LYS | 91 | 68.585 | 7.374 | 15.894 | 1.00 | 2.00 | R1 |
| ATOM | 866 | H | LYS | 91 | 68.356 | 7.886 | 16.698 | 1.00 | 35.00 | R1 |
| ATOM | 867 | CA | LYS | 91 | 67.621 | 7.296 | 14.795 | 1.00 | 2.67 | R1 |
| ATOM | 868 | CB | LYS | 91 | 66.189 | 7.286 | 15.325 | 1.00 | 2.00 | R1 |
| ATOM | 869 | CG | LYS | 91 | 65.162 | 7.562 | 14.288 | 1.00 | 2.00 | R1 |
| ATOM | 870 | CD | LYS | 91 | 63.783 | 7.192 | 14.720 | 1.00 | 2.00 | R1 |
| ATOM | 871 | CE | LYS | 91 | 62.773 | 7.646 | 13.675 | 1.00 | 2.00 | R1 |

TABLE 3-continued

Crystallographic coordinates for the refined co-crystal

| ATOM | 872 | NZ  | LYS | 91 | 61.385 | 7.167  | 13.969 | 1.00 | 2.14  | R1 |
|------|-----|-----|-----|----|--------|--------|--------|------|-------|----|
| ATOM | 873 | HZ1 | LYS | 91 | 60.720 | 7.511  | 13.246 | 1.00 | 35.00 | R1 |
| ATOM | 874 | HZ2 | LYS | 91 | 61.083 | 7.496  | 14.909 | 1.00 | 35.00 | R1 |
| ATOM | 875 | HZ3 | LYS | 91 | 61.407 | 6.128  | 13.956 | 1.00 | 35.00 | R1 |
| ATOM | 876 | C   | LYS | 91 | 67.867 | 8.474  | 13.863 | 1.00 | 2.00  | R1 |
| ATOM | 877 | O   | LYS | 91 | 68.023 | 9.602  | 14.324 | 1.00 | 2.00  | R1 |
| ATOM | 878 | N   | ILE | 92 | 67.871 | 8.230  | 12.551 | 1.00 | 2.03  | R1 |
| ATOM | 879 | H   | ILE | 92 | 67.625 | 7.353  | 12.207 | 1.00 | 35.00 | R1 |
| ATOM | 880 | CA  | ILE | 92 | 68.194 | 9.318  | 11.628 | 1.00 | 3.49  | R1 |
| ATOM | 881 | CB  | ILE | 92 | 69.572 | 9.072  | 10.946 | 1.00 | 2.00  | R1 |
| ATOM | 882 | CG2 | ILE | 92 | 70.673 | 9.088  | 11.980 | 1.00 | 2.00  | R1 |
| ATOM | 883 | CG1 | ILE | 92 | 69.588 | 7.729  | 10.206 | 1.00 | 2.93  | R1 |
| ATOM | 884 | CD1 | ILE | 92 | 70.736 | 7.575  | 9.235  | 1.00 | 2.00  | R1 |
| ATOM | 885 | C   | ILE | 92 | 67.193 | 9.820  | 10.587 | 1.00 | 2.00  | R1 |
| ATOM | 886 | O   | ILE | 92 | 67.005 | 11.026 | 10.441 | 1.00 | 2.00  | R1 |
| ATOM | 887 | N   | SER | 93 | 66.584 | 8.905  | 9.854  | 1.00 | 4.22  | R1 |
| ATOM | 888 | H   | SER | 93 | 66.773 | 7.957  | 10.016 | 1.00 | 35.00 | R1 |
| ATOM | 889 | CA  | SER | 93 | 65.627 | 9.248  | 8.788  | 1.00 | 8.07  | R1 |
| ATOM | 890 | CB  | SER | 93 | 64.330 | 9.828  | 9.380  | 1.00 | 4.01  | R1 |
| ATOM | 891 | OG  | SER | 93 | 64.402 | 11.225 | 9.509  | 1.00 | 2.90  | R1 |
| ATOM | 892 | HG  | SER | 93 | 65.063 | 11.487 | 10.153 | 1.00 | 35.00 | R1 |
| ATOM | 893 | C   | SER | 93 | 66.150 | 10.128 | 7.617  | 1.00 | 4.91  | R1 |
| ATOM | 894 | O   | SER | 93 | 66.485 | 11.311 | 7.802  | 1.00 | 6.70  | R1 |
| ATOM | 895 | N   | ALA | 94 | 66.153 | 9.550  | 6.410  | 1.00 | 4.05  | R1 |
| ATOM | 896 | H   | ALA | 94 | 65.835 | 8.638  | 6.310  | 1.00 | 35.00 | R1 |
| ATOM | 897 | CA  | ALA | 94 | 66.609 | 10.226 | 5.179  | 1.00 | 2.73  | R1 |
| ATOM | 898 | CB  | ALA | 94 | 67.944 | 9.664  | 4.768  | 1.00 | 2.00  | R1 |
| ATOM | 899 | C   | ALA | 94 | 65.613 | 10.114 | 4.005  | 1.00 | 2.44  | R1 |
| ATOM | 900 | O   | ALA | 94 | 64.977 | 9.082  | 3.829  | 1.00 | 2.09  | R1 |
| ATOM | 901 | N   | LYS | 95 | 65.471 | 11.176 | 3.209  | 1.00 | 5.36  | R1 |
| ATOM | 902 | H   | LYS | 95 | 65.983 | 11.987 | 3.413  | 1.00 | 35.00 | R1 |
| ATOM | 903 | CA  | LYS | 95 | 64.558 | 11.184 | 2.037  | 1.00 | 4.70  | R1 |
| ATOM | 904 | CB  | LYS | 95 | 63.680 | 12.444 | 2.025  | 1.00 | 2.00  | R1 |
| ATOM | 905 | CG  | LYS | 95 | 62.473 | 12.379 | 1.096  | 1.00 | 3.81  | R1 |
| ATOM | 906 | CD  | LYS | 95 | 61.719 | 13.707 | 1.059  | 1.00 | 2.04  | R1 |
| ATOM | 907 | CE  | LYS | 95 | 60.399 | 13.600 | 0.340  | 1.00 | 2.00  | R1 |
| ATOM | 908 | NZ  | LYS | 95 | 59.311 | 13.076 | 1.208  | 1.00 | 7.94  | R1 |
| ATOM | 909 | HZ1 | LYS | 95 | 59.198 | 13.699 | 2.034  | 1.00 | 35.00 | R1 |
| ATOM | 910 | HZ2 | LYS | 95 | 59.545 | 12.115 | 1.531  | 1.00 | 35.00 | R1 |
| ATOM | 911 | HZ3 | LYS | 95 | 58.419 | 13.051 | 0.674  | 1.00 | 35.00 | R1 |
| ATOM | 912 | C   | LYS | 95 | 65.387 | 11.146 | 0.752  | 1.00 | 5.12  | R1 |
| ATOM | 913 | O   | LYS | 95 | 66.444 | 11.781 | 0.682  | 1.00 | 2.79  | R1 |
| ATOM | 914 | N   | PHE | 96 | 64.879 | 10.440 | -0.261 | 1.00 | 4.57  | R1 |
| ATOM | 915 | H   | PHE | 96 | 64.003 | 10.028 | -0.137 | 1.00 | 35.00 | R1 |
| ATOM | 916 | CA  | PHE | 96 | 65.562 | 10.272 | -1.559 | 1.00 | 4.14  | R1 |
| ATOM | 917 | CB  | PHE | 96 | 66.048 | 8.823  | -1.730 | 1.00 | 3.38  | R1 |
| ATOM | 918 | CG  | PHE | 96 | 67.124 | 8.430  | -0.785 | 1.00 | 2.00  | R1 |
| ATOM | 919 | CD1 | PHE | 96 | 66.811 | 7.766  | 0.389  | 1.00 | 2.00  | R1 |
| ATOM | 920 | CD2 | PHE | 96 | 68.452 | 8.755  | -1.056 | 1.00 | 2.00  | R1 |
| ATOM | 921 | CE1 | PHE | 96 | 67.808 | 7.420  | 1.318  | 1.00 | 7.22  | R1 |
| ATOM | 922 | CE2 | PHE | 96 | 69.473 | 8.420  | -0.146 | 1.00 | 11.57 | R1 |
| ATOM | 923 | CZ  | PHE | 96 | 69.154 | 7.744  | 1.062  | 1.00 | 7.38  | R1 |
| ATOM | 924 | C   | PHE | 96 | 64.643 | 10.590 | -2.725 | 1.00 | 3.96  | R1 |
| ATOM | 925 | O   | PHE | 96 | 63.962 | 9.719  | -3.252 | 1.00 | 5.42  | R1 |
| ATOM | 926 | N   | VAL | 97 | 64.624 | 11.842 | -3.130 | 1.00 | 4.56  | R1 |
| ATOM | 927 | H   | VAL | 97 | 65.184 | 12.494 | -2.658 | 1.00 | 35.00 | R1 |
| ATOM | 928 | CA  | VAL | 97 | 63.786 | 12.264 | -4.233 | 1.00 | 2.87  | R1 |
| ATOM | 929 | CB  | VAL | 97 | 63.398 | 13.691 | -4.045 | 1.00 | 2.00  | R1 |
| ATOM | 930 | CG1 | VAL | 97 | 62.698 | 13.821 | -2.760 | 1.00 | 2.89  | R1 |
| ATOM | 931 | CG2 | VAL | 97 | 64.640 | 14.578 | -4.068 | 1.00 | 2.00  | R1 |
| ATOM | 932 | C   | VAL | 97 | 64.455 | 12.156 | -5.602 | 1.00 | 6.60  | R1 |
| ATOM | 933 | O   | VAL | 97 | 65.667 | 11.948 | -5.724 | 1.00 | 3.54  | R1 |
| ATOM | 934 | N   | GLU | 98 | 63.629 | 12.343 | -6.629 | 1.00 | 9.57  | R1 |
| ATOM | 935 | H   | GLU | 98 | 62.684 | 12.511 | -6.436 | 1.00 | 35.00 | R1 |
| ATOM | 936 | CA  | GLU | 98 | 64.043 | 12.312 | -8.021 | 1.00 | 4.42  | R1 |
| ATOM | 937 | CB  | GLU | 98 | 63.133 | 11.404 | -8.810 | 1.00 | 2.00  | R1 |
| ATOM | 938 | CG  | GLU | 98 | 63.905 | 10.310 | -9.443 | 1.00 | 2.31  | R1 |
| ATOM | 939 | CD  | GLU | 98 | 63.213 | 9.011  | -9.313 | 1.00 | 2.00  | R1 |
| ATOM | 940 | OE1 | GLU | 98 | 63.918 | 7.986  | -9.238 | 1.00 | 2.00  | R1 |
| ATOM | 941 | OE2 | GLU | 98 | 61.970 | 9.016  | -9.279 | 1.00 | 2.00  | R1 |
| ATOM | 942 | C   | GLU | 98 | 63.954 | 13.705 | -8.582 | 1.00 | 5.79  | R1 |
| ATOM | 943 | O   | GLU | 98 | 63.193 | 14.522 | -8.087 | 1.00 | 5.47  | R1 |
| ATOM | 944 | N   | ASN | 99 | 64.746 | 13.983 | -9.614 | 1.00 | 11.01 | R1 |
| ATOM | 945 | H   | ASN | 99 | 65.344 | 13.284 | -9.954 | 1.00 | 35.00 | R1 |
| ATOM | 946 | CA  | ASN | 99 | 64.754 | 15.296 | -10.235| 1.00 | 9.32  | R1 |
| ATOM | 947 | CB  | ASN | 99 | 65.723 | 15.318 | -11.421| 1.00 | 8.42  | R1 |
| ATOM | 948 | CG  | ASN | 99 | 67.176 | 15.140 | -11.019| 1.00 | 4.57  | R1 |

TABLE 3-continued

Crystallographic coordinates for the refined co-crystal

| ATOM | 949 | OD1 | ASN | 99 | 67.485 | 14.774 | −9.894 | 1.00 | 5.66 | R1 |
|---|---|---|---|---|---|---|---|---|---|---|
| ATOM | 950 | ND2 | ASN | 99 | 68.081 | 15.377 | −11.964 | 1.00 | 2.63 | R1 |
| ATOM | 951 | HD21 | ASN | 99 | 67.770 | 15.640 | −12.852 | 1.00 | 35.00 | R1 |
| ATOM | 952 | HD22 | ASN | 99 | 69.024 | 15.272 | −11.719 | 1.00 | 35.00 | R1 |
| ATOM | 953 | C | ASN | 99 | 63.349 | 15.636 | −10.727 | 1.00 | 12.53 | R1 |
| ATOM | 954 | O | ASN | 99 | 62.617 | 14.767 | −11.208 | 1.00 | 13.87 | R1 |
| ATOM | 955 | N | GLU | 100 | 62.959 | 16.894 | −10.581 | 1.00 | 15.06 | R1 |
| ATOM | 956 | H | GLU | 100 | 63.532 | 17.538 | −10.134 | 1.00 | 35.00 | R1 |
| ATOM | 957 | CA | GLU | 100 | 61.656 | 17.345 | −11.052 | 1.00 | 21.10 | R1 |
| ATOM | 958 | CB | GLU | 100 | 61.318 | 18.683 | −10.411 | 1.00 | 18.73 | R1 |
| ATOM | 959 | CG | GLU | 100 | 61.265 | 18.592 | −8.904 | 1.00 | 12.39 | R1 |
| ATOM | 960 | CD | GLU | 100 | 60.306 | 19.564 | −8.329 | 1.00 | 12.95 | R1 |
| ATOM | 961 | OE1 | GLU | 100 | 59.101 | 19.214 | −8.235 | 1.00 | 13.43 | R1 |
| ATOM | 962 | OE2 | GLU | 100 | 60.750 | 20.686 | −8.006 | 1.00 | 12.56 | R1 |
| ATOM | 963 | C | GLU | 100 | 61.690 | 17.458 | −12.573 | 1.00 | 25.51 | R1 |
| ATOM | 964 | O | GLU | 100 | 62.733 | 17.802 | −13.144 | 1.00 | 27.53 | R1 |
| ATOM | 965 | N | PRO | 101 | 60.543 | 17.220 | −13.249 | 1.00 | 25.69 | R1 |
| ATOM | 966 | CD | PRO | 101 | 59.210 | 17.056 | −12.644 | 1.00 | 29.70 | R1 |
| ATOM | 967 | CA | PRO | 101 | 60.422 | 17.276 | −14.717 | 1.00 | 30.81 | R1 |
| ATOM | 968 | CB | PRO | 101 | 58.916 | 17.338 | −14.935 | 1.00 | 30.54 | R1 |
| ATOM | 969 | CG | PRO | 101 | 58.404 | 16.498 | −13.800 | 1.00 | 31.47 | R1 |
| ATOM | 970 | C | PRO | 101 | 61.147 | 18.418 | −15.406 | 1.00 | 27.14 | R1 |
| ATOM | 971 | O | PRO | 101 | 61.009 | 19.588 | −15.035 | 1.00 | 21.18 | R1 |
| ATOM | 972 | N | ASN | 102 | 61.940 | 18.045 | −16.405 | 1.00 | 28.04 | R1 |
| ATOM | 973 | H | ASN | 102 | 61.991 | 17.096 | −16.648 | 1.00 | 35.00 | R1 |
| ATOM | 974 | CA | ASN | 102 | 62.724 | 19.004 | −17.168 | 1.00 | 31.40 | R1 |
| ATOM | 975 | CB | ASN | 102 | 61.820 | 19.876 | −18.049 | 1.00 | 33.20 | R1 |
| ATOM | 976 | CG | ASN | 102 | 60.713 | 19.084 | −18.704 | 1.00 | 34.31 | R1 |
| ATOM | 977 | OD1 | ASN | 102 | 60.950 | 18.014 | −19.275 | 1.00 | 32.12 | R1 |
| ATOM | 978 | ND2 | ASN | 102 | 59.483 | 19.585 | −18.588 | 1.00 | 33.63 | R1 |
| ATOM | 979 | HD21 | ASN | 102 | 59.352 | 20.418 | −18.089 | 1.00 | 35.00 | R1 |
| ATOM | 980 | HD22 | ASN | 102 | 58.747 | 19.092 | −19.011 | 1.00 | 35.00 | R1 |
| ATOM | 981 | C | ASN | 102 | 63.461 | 19.857 | −16.152 | 1.00 | 29.82 | R1 |
| ATOM | 982 | O | ASN | 102 | 63.159 | 21.037 | −15.948 | 1.00 | 30.22 | R1 |
| ATOM | 983 | N | LEU | 103 | 64.338 | 19.190 | −15.423 | 1.00 | 29.35 | R1 |
| ATOM | 984 | H | LEU | 103 | 64.454 | 18.232 | −15.598 | 1.00 | 35.00 | R1 |
| ATOM | 985 | CA | LEU | 103 | 65.138 | 19.838 | −14.407 | 1.00 | 28.01 | R1 |
| ATOM | 986 | CB | LEU | 103 | 64.266 | 20.284 | −13.235 | 1.00 | 23.58 | R1 |
| ATOM | 987 | CG | LEU | 103 | 64.777 | 21.506 | −12.496 | 1.00 | 18.94 | R1 |
| ATOM | 988 | CD1 | LEU | 103 | 65.933 | 22.118 | −13.255 | 1.00 | 20.02 | R1 |
| ATOM | 989 | CD2 | LEU | 103 | 63.645 | 22.502 | −12.336 | 1.00 | 19.72 | R1 |
| ATOM | 990 | C | LEU | 103 | 66.152 | 18.809 | −13.959 | 1.00 | 26.15 | R1 |
| ATOM | 991 | O | LEU | 103 | 65.812 | 17.627 | −13.769 | 1.00 | 26.23 | R1 |
| ATOM | 992 | N | CYS | 104 | 67.394 | 19.267 | −13.810 | 1.00 | 22.88 | R1 |
| ATOM | 993 | H | CYS | 104 | 67.582 | 20.214 | −13.977 | 1.00 | 35.00 | R1 |
| ATOM | 994 | CA | CYS | 104 | 68.480 | 18.397 | −13.413 | 1.00 | 19.95 | R1 |
| ATOM | 995 | C | CYS | 104 | 68.606 | 18.183 | −11.899 | 1.00 | 19.69 | R1 |
| ATOM | 996 | O | CYS | 104 | 69.557 | 17.546 | −11.442 | 1.00 | 22.87 | R1 |
| ATOM | 997 | CB | CYS | 104 | 69.795 | 18.902 | −14.030 | 1.00 | 14.34 | R1 |
| ATOM | 998 | SG | CYS | 104 | 70.459 | 20.462 | −13.373 | 1.00 | 10.97 | R1 |
| ATOM | 999 | N | TYR | 105 | 67.619 | 18.652 | −11.135 | 1.00 | 17.37 | R1 |
| ATOM | 1000 | H | TYR | 105 | 66.858 | 19.096 | −11.565 | 1.00 | 35.00 | R1 |
| ATOM | 1001 | CA | TYR | 105 | 67.619 | 18.530 | −9.662 | 1.00 | 14.30 | R1 |
| ATOM | 1002 | CB | TYR | 105 | 68.337 | 19.736 | −9.002 | 1.00 | 7.13 | R1 |
| ATOM | 1003 | CG | TYR | 105 | 67.761 | 21.099 | −9.315 | 1.00 | 2.00 | R1 |
| ATOM | 1004 | CD1 | TYR | 105 | 66.621 | 21.555 | −8.679 | 1.00 | 2.00 | R1 |
| ATOM | 1005 | CE1 | TYR | 105 | 66.111 | 22.836 | −8.933 | 1.00 | 3.20 | R1 |
| ATOM | 1006 | CD2 | TYR | 105 | 68.381 | 21.953 | −10.221 | 1.00 | 2.20 | R1 |
| ATOM | 1007 | CE2 | TYR | 105 | 67.880 | 23.237 | −10.478 | 1.00 | 2.00 | R1 |
| ATOM | 1008 | CZ | TYR | 105 | 66.747 | 23.667 | −9.828 | 1.00 | 2.00 | R1 |
| ATOM | 1009 | OH | TYR | 105 | 66.244 | 24.922 | −10.038 | 1.00 | 2.00 | R1 |
| ATOM | 1010 | HH | TYR | 105 | 66.855 | 25.452 | −10.551 | 1.00 | 35.00 | R1 |
| ATOM | 1011 | C | TYR | 105 | 66.195 | 18.433 | −9.137 | 1.00 | 14.02 | R1 |
| ATOM | 1012 | O | TYR | 105 | 65.279 | 18.178 | −9.907 | 1.00 | 18.48 | R1 |
| ATOM | 1013 | N | ASN | 106 | 66.028 | 18.583 | −7.823 | 1.00 | 13.91 | R1 |
| ATOM | 1014 | H | ASN | 106 | 66.819 | 18.686 | −7.253 | 1.00 | 35.00 | R1 |
| ATOM | 1015 | CA | ASN | 106 | 64.709 | 18.571 | −7.167 | 1.00 | 9.08 | R1 |
| ATOM | 1016 | CB | ASN | 106 | 64.340 | 17.184 | −6.608 | 1.00 | 8.36 | R1 |
| ATOM | 1017 | CG | ASN | 106 | 62.957 | 17.166 | −5.938 | 1.00 | 10.14 | R1 |
| ATOM | 1018 | OD1 | ASN | 106 | 62.395 | 18.210 | −5.615 | 1.00 | 16.71 | R1 |
| ATOM | 1019 | ND2 | ASN | 106 | 62.409 | 15.983 | −5.740 | 1.00 | 8.94 | R1 |
| ATOM | 1020 | HD21 | ASN | 106 | 62.898 | 15.189 | −6.037 | 1.00 | 35.00 | R1 |
| ATOM | 1021 | HD22 | ASN | 106 | 61.533 | 15.949 | −5.300 | 1.00 | 35.00 | R1 |
| ATOM | 1022 | C | ASN | 106 | 64.744 | 19.589 | −6.037 | 1.00 | 5.72 | R1 |
| ATOM | 1023 | O | ASN | 106 | 65.644 | 19.571 | −5.201 | 1.00 | 7.33 | R1 |
| ATOM | 1024 | N | ALA | 107 | 63.758 | 20.469 | −6.007 | 1.00 | 2.69 | R1 |
| ATOM | 1025 | H | ALA | 107 | 63.050 | 20.415 | −6.681 | 1.00 | 35.00 | R1 |

TABLE 3-continued

Crystallographic coordinates for the refined co-crystal

| ATOM | 1026 | CA | ALA | 107 | 63.695 | 21.496 | −4.988 | 1.00 | 3.76 | R1 |
|------|------|------|-----|-----|--------|--------|--------|------|-------|----|
| ATOM | 1027 | CB | ALA | 107 | 62.339 | 22.171 | −5.037 | 1.00 | 2.00 | R1 |
| ATOM | 1028 | C | ALA | 107 | 64.030 | 21.033 | −3.541 | 1.00 | 3.21 | R1 |
| ATOM | 1029 | O | ALA | 107 | 64.711 | 21.729 | −2.794 | 1.00 | 2.00 | R1 |
| ATOM | 1030 | N | GLN | 108 | 63.638 | 19.822 | −3.184 | 1.00 | 2.00 | R1 |
| ATOM | 1031 | H | GLN | 108 | 63.190 | 19.241 | −3.830 | 1.00 | 35.00 | R1 |
| ATOM | 1032 | CA | GLN | 108 | 63.882 | 19.338 | −1.837 | 1.00 | 3.22 | R1 |
| ATOM | 1033 | CB | GLN | 108 | 63.168 | 18.011 | −1.637 | 1.00 | 2.00 | R1 |
| ATOM | 1034 | CG | GLN | 108 | 61.676 | 18.246 | −1.527 | 1.00 | 2.00 | R1 |
| ATOM | 1035 | CD | GLN | 108 | 60.860 | 16.984 | −1.588 | 1.00 | 2.00 | R1 |
| ATOM | 1036 | OE1 | GLN | 108 | 60.190 | 16.623 | −0.626 | 1.00 | 4.42 | R1 |
| ATOM | 1037 | NE2 | GLN | 108 | 60.888 | 16.319 | −2.729 | 1.00 | 2.00 | R1 |
| ATOM | 1038 | HE21 | GLN | 108 | 61.427 | 16.680 | −3.462 | 1.00 | 35.00 | R1 |
| ATOM | 1039 | HE22 | GLN | 108 | 60.363 | 15.495 | −2.792 | 1.00 | 35.00 | R1 |
| ATOM | 1040 | C | GLN | 108 | 65.332 | 19.284 | −1.360 | 1.00 | 3.65 | R1 |
| ATOM | 1041 | O | GLN | 108 | 65.652 | 19.715 | −0.245 | 1.00 | 4.49 | R1 |
| ATOM | 1042 | N | ALA | 109 | 66.210 | 18.868 | −2.258 | 1.00 | 3.01 | R1 |
| ATOM | 1043 | H | ALA | 109 | 65.879 | 18.651 | −3.155 | 1.00 | 35.00 | R1 |
| ATOM | 1044 | CA | ALA | 109 | 67.621 | 18.717 | −1.983 | 1.00 | 2.00 | R1 |
| ATOM | 1045 | CB | ALA | 109 | 68.180 | 17.701 | −2.949 | 1.00 | 2.00 | R1 |
| ATOM | 1046 | C | ALA | 109 | 68.428 | 19.993 | −2.055 | 1.00 | 2.00 | R1 |
| ATOM | 1047 | O | ALA | 109 | 69.651 | 19.966 | −1.951 | 1.00 | 2.00 | R1 |
| ATOM | 1048 | N | ILE | 110 | 67.768 | 21.123 | −2.227 | 1.00 | 2.00 | R1 |
| ATOM | 1049 | H | ILE | 110 | 66.791 | 21.147 | −2.281 | 1.00 | 35.00 | R1 |
| ATOM | 1050 | CA | ILE | 110 | 68.542 | 22.332 | −2.367 | 1.00 | 2.22 | R1 |
| ATOM | 1051 | CB | ILE | 110 | 67.780 | 23.481 | −3.002 | 1.00 | 2.00 | R1 |
| ATOM | 1052 | CG2 | ILE | 110 | 68.716 | 24.675 | −3.191 | 1.00 | 2.00 | R1 |
| ATOM | 1053 | CG1 | ILE | 110 | 67.161 | 23.081 | −4.327 | 1.00 | 2.00 | R1 |
| ATOM | 1054 | CD1 | ILE | 110 | 66.489 | 24.261 | −5.025 | 1.00 | 2.00 | R1 |
| ATOM | 1055 | C | ILE | 110 | 69.058 | 22.877 | −1.087 | 1.00 | 4.30 | R1 |
| ATOM | 1056 | O | ILE | 110 | 68.300 | 23.137 | −0.168 | 1.00 | 8.99 | R1 |
| ATOM | 1057 | N | PHE | 111 | 70.340 | 23.168 | −1.078 | 1.00 | 7.72 | R1 |
| ATOM | 1058 | H | PHE | 111 | 70.881 | 22.977 | −1.872 | 1.00 | 35.00 | R1 |
| ATOM | 1059 | CA | PHE | 111 | 70.961 | 23.775 | 0.069 | 1.00 | 10.98 | R1 |
| ATOM | 1060 | CB | PHE | 111 | 72.413 | 23.348 | 0.164 | 1.00 | 10.91 | R1 |
| ATOM | 1061 | CG | PHE | 111 | 72.563 | 21.946 | 0.599 | 1.00 | 11.18 | R1 |
| ATOM | 1062 | CD1 | PHE | 111 | 72.356 | 20.910 | −0.296 | 1.00 | 11.59 | R1 |
| ATOM | 1063 | CD2 | PHE | 111 | 72.845 | 21.652 | 1.919 | 1.00 | 9.04 | R1 |
| ATOM | 1064 | CE1 | PHE | 111 | 72.430 | 19.608 | 0.119 | 1.00 | 10.06 | R1 |
| ATOM | 1065 | CE2 | PHE | 111 | 72.920 | 20.357 | 2.338 | 1.00 | 8.71 | R1 |
| ATOM | 1066 | CZ | PHE | 111 | 72.713 | 19.333 | 1.437 | 1.00 | 11.71 | R1 |
| ATOM | 1067 | C | PHE | 111 | 70.851 | 25.259 | −0.089 | 1.00 | 11.06 | R1 |
| ATOM | 1068 | O | PHE | 111 | 71.718 | 25.873 | −0.677 | 1.00 | 9.81 | R1 |
| ATOM | 1069 | N | LYS | 112 | 69.756 | 25.819 | 0.422 | 1.00 | 20.92 | R1 |
| ATOM | 1070 | H | LYS | 112 | 69.092 | 25.245 | 0.858 | 1.00 | 35.00 | R1 |
| ATOM | 1071 | CA | LYS | 112 | 69.496 | 27.255 | 0.354 | 1.00 | 30.17 | R1 |
| ATOM | 1072 | CB | LYS | 112 | 68.136 | 27.607 | 0.962 | 1.00 | 31.82 | R1 |
| ATOM | 1073 | CG | LYS | 112 | 67.719 | 29.046 | 0.693 | 1.00 | 37.00 | R1 |
| ATOM | 1074 | CD | LYS | 112 | 66.234 | 29.279 | 0.958 | 1.00 | 39.72 | R1 |
| ATOM | 1075 | CE | LYS | 112 | 65.851 | 30.751 | 0.774 | 1.00 | 43.70 | R1 |
| ATOM | 1076 | NZ | LYS | 112 | 66.049 | 31.253 | −0.630 | 1.00 | 42.14 | R1 |
| ATOM | 1077 | HZ1 | LYS | 112 | 65.477 | 30.704 | −1.304 | 1.00 | 35.00 | R1 |
| ATOM | 1078 | HZ2 | LYS | 112 | 67.051 | 31.189 | −0.900 | 1.00 | 35.00 | R1 |
| ATOM | 1079 | HZ3 | LYS | 112 | 65.759 | 32.252 | −0.683 | 1.00 | 35.00 | R1 |
| ATOM | 1080 | C | LYS | 112 | 70.607 | 27.998 | 1.059 | 1.00 | 33.39 | R1 |
| ATOM | 1081 | O | LYS | 112 | 70.525 | 28.277 | 2.249 | 1.00 | 29.77 | R1 |
| ATOM | 1082 | N | GLN | 113 | 71.667 | 28.239 | 0.283 | 1.00 | 41.81 | R1 |
| ATOM | 1083 | H | GLN | 113 | 71.612 | 27.949 | −0.651 | 1.00 | 35.00 | R1 |
| ATOM | 1084 | CA | GLN | 113 | 72.910 | 28.910 | 0.681 | 1.00 | 47.80 | R1 |
| ATOM | 1085 | CB | GLN | 113 | 72.657 | 30.305 | 1.277 | 1.00 | 48.18 | R1 |
| ATOM | 1086 | CG | GLN | 113 | 73.798 | 31.288 | 1.017 | 1.00 | 44.82 | R1 |
| ATOM | 1087 | CD | GLN | 113 | 73.743 | 32.516 | 1.896 | 1.00 | 45.64 | R1 |
| ATOM | 1088 | OE1 | GLN | 113 | 74.740 | 33.223 | 2.049 | 1.00 | 41.04 | R1 |
| ATOM | 1089 | NE2 | GLN | 113 | 72.577 | 32.779 | 2.484 | 1.00 | 44.94 | R1 |
| ATOM | 1090 | HE21 | GLN | 113 | 71.790 | 32.219 | 2.346 | 1.00 | 35.00 | R1 |
| ATOM | 1091 | HE22 | GLN | 113 | 72.554 | 33.572 | 3.061 | 1.00 | 35.00 | R1 |
| ATOM | 1092 | C | GLN | 113 | 73.746 | 28.063 | 1.634 | 1.00 | 51.27 | R1 |
| ATOM | 1093 | O | GLN | 113 | 73.290 | 27.042 | 2.146 | 1.00 | 53.76 | R1 |
| ATOM | 1094 | N | LYS | 114 | 74.989 | 28.472 | 1.835 | 1.00 | 55.04 | R1 |
| ATOM | 1095 | H | LYS | 114 | 75.326 | 29.251 | 1.349 | 1.00 | 35.00 | R1 |
| ATOM | 1096 | CA | LYS | 114 | 75.888 | 27.766 | 2.729 | 1.00 | 57.56 | R1 |
| ATOM | 1097 | CB | LYS | 114 | 76.216 | 26.376 | 2.171 | 1.00 | 59.02 | R1 |
| ATOM | 1098 | CG | LYS | 114 | 76.829 | 26.355 | 0.765 | 1.00 | 55.91 | R1 |
| ATOM | 1099 | CD | LYS | 114 | 77.535 | 25.046 | 0.555 | 1.00 | 52.32 | R1 |
| ATOM | 1100 | CE | LYS | 114 | 78.587 | 24.861 | 1.633 | 1.00 | 53.03 | R1 |
| ATOM | 1101 | NZ | LYS | 114 | 79.192 | 23.516 | 1.674 | 1.00 | 48.06 | R1 |
| ATOM | 1102 | HZ1 | LYS | 114 | 79.919 | 23.485 | 2.417 | 1.00 | 35.00 | R1 |

TABLE 3-continued

Crystallographic coordinates for the refined co-crystal

| ATOM | 1103 | HZ2 | LYS | 114 | 79.612 | 23.287 | 0.752 | 1.00 | 35.00 | R1 |
|---|---|---|---|---|---|---|---|---|---|---|
| ATOM | 1104 | HZ3 | LYS | 114 | 78.452 | 22.816 | 1.892 | 1.00 | 35.00 | R1 |
| ATOM | 1105 | C | LYS | 114 | 77.144 | 28.607 | 2.870 | 1.00 | 60.33 | R1 |
| ATOM | 1106 | O | LYS | 114 | 77.097 | 29.813 | 2.631 | 1.00 | 58.72 | R1 |
| ATOM | 1107 | N | LEU | 115 | 78.256 | 27.978 | 3.252 | 1.00 | 64.77 | R1 |
| ATOM | 1108 | H | LEU | 115 | 78.231 | 27.017 | 3.439 | 1.00 | 35.00 | R1 |
| ATOM | 1109 | CA | LEU | 115 | 79.529 | 28.681 | 3.418 | 1.00 | 69.56 | R1 |
| ATOM | 1110 | CB | LEU | 115 | 80.593 | 27.758 | 4.038 | 1.00 | 70.03 | R1 |
| ATOM | 1111 | CG | LEU | 115 | 80.322 | 27.164 | 5.433 | 1.00 | 70.56 | R1 |
| ATOM | 1112 | CD1 | LEU | 115 | 79.590 | 25.828 | 5.305 | 1.00 | 69.77 | R1 |
| ATOM | 1113 | CD2 | LEU | 115 | 81.627 | 26.974 | 6.195 | 1.00 | 69.48 | R1 |
| ATOM | 1114 | C | LEU | 115 | 80.032 | 29.257 | 2.089 | 1.00 | 71.92 | R1 |
| ATOM | 1115 | O | LEU | 115 | 80.150 | 28.529 | 1.091 | 1.00 | 70.70 | R1 |
| ATOM | 1116 | N | PRO | 116 | 80.229 | 30.597 | 2.040 | 1.00 | 72.30 | R1 |
| ATOM | 1117 | CD | PRO | 116 | 79.560 | 31.508 | 2.989 | 1.00 | 75.36 | R1 |
| ATOM | 1118 | CA | PRO | 116 | 80.705 | 31.368 | 0.886 | 1.00 | 76.18 | R1 |
| ATOM | 1119 | CB | PRO | 116 | 79.554 | 32.349 | 0.680 | 1.00 | 75.05 | R1 |
| ATOM | 1120 | CG | PRO | 116 | 79.221 | 32.748 | 2.110 | 1.00 | 74.77 | R1 |
| ATOM | 1121 | C | PRO | 116 | 82.009 | 32.125 | 1.176 | 1.00 | 73.72 | R1 |
| ATOM | 1122 | O | PRO | 116 | 82.908 | 31.610 | 1.852 | 1.00 | 74.52 | R1 |
| ATOM | 1123 | N | VAL | 117 | 82.115 | 33.328 | 0.608 | 1.00 | 71.97 | R1 |
| ATOM | 1124 | H | VAL | 117 | 81.423 | 33.654 | −0.001 | 1.00 | 35.00 | R1 |
| ATOM | 1125 | CA | VAL | 117 | 83.262 | 34.210 | 0.818 | 1.00 | 71.46 | R1 |
| ATOM | 1126 | CB | VAL | 117 | 84.321 | 34.119 | −0.325 | 1.00 | 68.41 | R1 |
| ATOM | 1127 | CG1 | VAL | 117 | 85.442 | 35.134 | −0.092 | 1.00 | 63.09 | R1 |
| ATOM | 1128 | CG2 | VAL | 117 | 84.906 | 32.715 | −0.400 | 1.00 | 65.05 | R1 |
| ATOM | 1129 | C | VAL | 117 | 82.725 | 35.639 | 0.910 | 1.00 | 71.06 | R1 |
| ATOM | 1130 | O | VAL | 117 | 82.944 | 36.325 | 1.912 | 1.00 | 70.46 | R1 |
| ATOM | 1131 | N | ALA | 118 | 81.974 | 36.051 | −0.113 | 1.00 | 71.48 | R1 |
| ATOM | 1132 | H | ALA | 118 | 81.803 | 35.426 | −0.849 | 1.00 | 35.00 | R1 |
| ATOM | 1133 | CA | ALA | 118 | 81.396 | 37.395 | −0.172 | 1.00 | 72.81 | R1 |
| ATOM | 1134 | CB | ALA | 118 | 82.510 | 38.438 | −0.266 | 1.00 | 71.67 | R1 |
| ATOM | 1135 | C | ALA | 118 | 80.426 | 37.557 | −1.346 | 1.00 | 72.99 | R1 |
| ATOM | 1136 | O | ALA | 118 | 79.792 | 36.585 | −1.783 | 1.00 | 72.54 | R1 |
| ATOM | 1137 | N | GLY | 119 | 80.316 | 38.797 | −1.833 | 1.00 | 73.76 | R1 |
| ATOM | 1138 | H | GLY | 119 | 80.806 | 39.543 | −1.431 | 1.00 | 35.00 | R1 |
| ATOM | 1139 | CA | GLY | 119 | 79.446 | 39.123 | −2.958 | 1.00 | 74.35 | R1 |
| ATOM | 1140 | C | GLY | 119 | 80.022 | 38.829 | −4.340 | 1.00 | 73.36 | R1 |
| ATOM | 1141 | O | GLY | 119 | 79.275 | 38.722 | −5.322 | 1.00 | 72.24 | R1 |
| ATOM | 1142 | N | ASP | 120 | 81.355 | 38.762 | −4.419 | 1.00 | 71.71 | R1 |
| ATOM | 1143 | H | ASP | 120 | 81.877 | 38.932 | −3.608 | 1.00 | 35.00 | R1 |
| ATOM | 1144 | CA | ASP | 120 | 82.076 | 38.443 | −5.657 | 1.00 | 67.56 | R1 |
| ATOM | 1145 | CB | ASP | 120 | 83.599 | 38.473 | −5.390 | 1.00 | 69.02 | R1 |
| ATOM | 1146 | CG | ASP | 120 | 84.439 | 38.059 | −6.596 | 1.00 | 69.15 | R1 |
| ATOM | 1147 | OD1 | ASP | 120 | 84.881 | 38.943 | −7.365 | 1.00 | 69.56 | R1 |
| ATOM | 1148 | OD2 | ASP | 120 | 84.707 | 36.848 | −6.740 | 1.00 | 69.76 | R1 |
| ATOM | 1149 | C | ASP | 120 | 81.593 | 37.037 | −6.018 | 1.00 | 64.05 | R1 |
| ATOM | 1150 | O | ASP | 120 | 80.873 | 36.865 | −6.999 | 1.00 | 64.20 | R1 |
| ATOM | 1151 | N | GLY | 121 | 81.881 | 36.074 | −5.142 | 1.00 | 58.96 | R1 |
| ATOM | 1152 | H | GLY | 121 | 82.384 | 36.304 | −4.332 | 1.00 | 35.00 | R1 |
| ATOM | 1153 | CA | GLY | 121 | 81.461 | 34.696 | −5.347 | 1.00 | 51.39 | R1 |
| ATOM | 1154 | C | GLY | 121 | 81.994 | 33.782 | −4.259 | 1.00 | 45.31 | R1 |
| ATOM | 1155 | O | GLY | 121 | 82.682 | 34.254 | −3.345 | 1.00 | 43.37 | R1 |
| ATOM | 1156 | N | GLY | 122 | 81.668 | 32.488 | −4.347 | 1.00 | 38.61 | R1 |
| ATOM | 1157 | H | GLY | 122 | 81.099 | 32.181 | −5.083 | 1.00 | 35.00 | R1 |
| ATOM | 1158 | CA | GLY | 122 | 82.148 | 31.525 | −3.364 | 1.00 | 30.93 | R1 |
| ATOM | 1159 | C | GLY | 122 | 81.145 | 30.501 | −2.847 | 1.00 | 25.72 | R1 |
| ATOM | 1160 | O | GLY | 122 | 80.404 | 30.785 | −1.910 | 1.00 | 24.62 | R1 |
| ATOM | 1161 | N | LEU | 123 | 81.129 | 29.305 | −3.444 | 1.00 | 19.73 | R1 |
| ATOM | 1162 | H | LEU | 123 | 81.748 | 29.131 | −4.165 | 1.00 | 35.00 | R1 |
| ATOM | 1163 | CA | LEU | 123 | 80.225 | 28.227 | −3.033 | 1.00 | 12.40 | R1 |
| ATOM | 1164 | CB | LEU | 123 | 79.200 | 27.948 | −4.125 | 1.00 | 10.33 | R1 |
| ATOM | 1165 | CG | LEU | 123 | 78.211 | 29.088 | −4.381 | 1.00 | 10.23 | R1 |
| ATOM | 1166 | CD1 | LEU | 123 | 77.345 | 28.800 | −5.593 | 1.00 | 10.74 | R1 |
| ATOM | 1167 | CD2 | LEU | 123 | 77.340 | 29.264 | −3.159 | 1.00 | 10.49 | R1 |
| ATOM | 1168 | C | LEU | 123 | 80.994 | 26.954 | −2.696 | 1.00 | 9.47 | R1 |
| ATOM | 1169 | O | LEU | 123 | 82.170 | 26.823 | −3.041 | 1.00 | 11.34 | R1 |
| ATOM | 1170 | N | VAL | 124 | 80.356 | 26.031 | −1.986 | 1.00 | 5.19 | R1 |
| ATOM | 1171 | H | VAL | 124 | 79.431 | 26.183 | −1.701 | 1.00 | 35.00 | R1 |
| ATOM | 1172 | CA | VAL | 124 | 81.024 | 24.784 | −1.625 | 1.00 | 2.18 | R1 |
| ATOM | 1173 | CB | VAL | 124 | 81.510 | 24.804 | −0.138 | 1.00 | 2.61 | R1 |
| ATOM | 1174 | CG1 | VAL | 124 | 82.063 | 23.472 | 0.240 | 1.00 | 3.91 | R1 |
| ATOM | 1175 | CG2 | VAL | 124 | 82.615 | 25.831 | 0.062 | 1.00 | 2.00 | R1 |
| ATOM | 1176 | C | VAL | 124 | 80.177 | 23.533 | −1.936 | 1.00 | 2.37 | R1 |
| ATOM | 1177 | O | VAL | 124 | 78.949 | 23.545 | −1.833 | 1.00 | 2.00 | R1 |
| ATOM | 1178 | N | CYS | 125 | 80.832 | 22.460 | −2.357 | 1.00 | 2.00 | R1 |
| ATOM | 1179 | H | CYS | 125 | 81.799 | 22.446 | −2.380 | 1.00 | 35.00 | R1 |

TABLE 3-continued

Crystallographic coordinates for the refined co-crystal

| ATOM | 1180 | CA | CYS | 125 | 80.113 | 21.231 | −2.704 | 1.00 | 4.80 | R1 |
|---|---|---|---|---|---|---|---|---|---|---|
| ATOM | 1181 | C | CYS | 125 | 79.962 | 20.337 | −1.465 | 1.00 | 2.00 | R1 |
| ATOM | 1182 | O | CYS | 125 | 80.844 | 19.539 | −1.147 | 1.00 | 2.00 | R1 |
| ATOM | 1183 | CB | CYS | 125 | 80.860 | 20.523 | −3.846 | 1.00 | 4.71 | R1 |
| ATOM | 1184 | SG | CYS | 125 | 80.010 | 19.099 | −4.574 | 1.00 | 2.00 | R1 |
| ATOM | 1185 | N | PRO | 126 | 78.801 | 20.400 | −0.808 | 1.00 | 2.00 | R1 |
| ATOM | 1186 | CD | PRO | 126 | 77.590 | 21.072 | −1.278 | 1.00 | 2.00 | R1 |
| ATOM | 1187 | CA | PRO | 126 | 78.516 | 19.629 | 0.398 | 1.00 | 2.00 | R1 |
| ATOM | 1188 | CB | PRO | 126 | 77.093 | 20.031 | 0.754 | 1.00 | 2.00 | R1 |
| ATOM | 1189 | CG | PRO | 126 | 76.850 | 21.259 | 0.001 | 1.00 | 3.85 | R1 |
| ATOM | 1190 | C | PRO | 126 | 78.617 | 18.134 | 0.307 | 1.00 | 2.44 | R1 |
| ATOM | 1191 | O | PRO | 126 | 78.294 | 17.519 | −0.710 | 1.00 | 4.15 | R1 |
| ATOM | 1192 | N | TYR | 127 | 79.074 | 17.563 | 1.408 | 1.00 | 2.00 | R1 |
| ATOM | 1193 | H | TYR | 127 | 79.333 | 18.151 | 2.150 | 1.00 | 35.00 | R1 |
| ATOM | 1194 | CA | TYR | 127 | 79.209 | 16.129 | 1.591 | 1.00 | 2.26 | R1 |
| ATOM | 1195 | CB | TYR | 127 | 77.826 | 15.477 | 1.537 | 1.00 | 2.64 | R1 |
| ATOM | 1196 | CG | TYR | 127 | 76.883 | 16.035 | 2.568 | 1.00 | 2.00 | R1 |
| ATOM | 1197 | CD1 | TYR | 127 | 76.107 | 17.157 | 2.294 | 1.00 | 2.00 | R1 |
| ATOM | 1198 | CE1 | TYR | 127 | 75.230 | 17.663 | 3.221 | 1.00 | 3.02 | R1 |
| ATOM | 1199 | CD2 | TYR | 127 | 76.755 | 15.432 | 3.805 | 1.00 | 2.00 | R1 |
| ATOM | 1200 | CE2 | TYR | 127 | 75.871 | 15.922 | 4.745 | 1.00 | 3.99 | R1 |
| ATOM | 1201 | CZ | TYR | 127 | 75.110 | 17.040 | 4.449 | 1.00 | 4.88 | R1 |
| ATOM | 1202 | OH | TYR | 127 | 74.236 | 17.539 | 5.391 | 1.00 | 9.73 | R1 |
| ATOM | 1203 | HH | TYR | 127 | 73.842 | 18.347 | 5.054 | 1.00 | 35.00 | R1 |
| ATOM | 1204 | C | TYR | 127 | 80.195 | 15.385 | 0.714 | 1.00 | 2.00 | R1 |
| ATOM | 1205 | O | TYR | 127 | 80.111 | 14.162 | 0.566 | 1.00 | 3.49 | R1 |
| ATOM | 1206 | N | MET | 128 | 81.180 | 16.097 | 0.198 | 1.00 | 2.00 | R1 |
| ATOM | 1207 | H | MET | 128 | 81.244 | 17.057 | 0.394 | 1.00 | 35.00 | R1 |
| ATOM | 1208 | CA | MET | 128 | 82.154 | 15.456 | −0.659 | 1.00 | 2.00 | R1 |
| ATOM | 1209 | CB | MET | 128 | 82.879 | 16.501 | −1.506 | 1.00 | 2.00 | R1 |
| ATOM | 1210 | CG | MET | 128 | 82.005 | 17.092 | −2.602 | 1.00 | 2.00 | R1 |
| ATOM | 1211 | SD | MET | 128 | 81.097 | 15.799 | −3.468 | 1.00 | 2.00 | R1 |
| ATOM | 1212 | CE | MET | 128 | 82.415 | 14.997 | −4.205 | 1.00 | 2.00 | R1 |
| ATOM | 1213 | C | MET | 128 | 83.132 | 14.565 | 0.077 | 1.00 | 2.00 | R1 |
| ATOM | 1214 | O | MET | 128 | 83.630 | 13.609 | −0.500 | 1.00 | 2.00 | R1 |
| ATOM | 1215 | N | GLU | 129 | 83.326 | 14.853 | 1.368 | 1.00 | 5.60 | R1 |
| ATOM | 1216 | H | GLU | 129 | 82.808 | 15.601 | 1.734 | 1.00 | 35.00 | R1 |
| ATOM | 1217 | CA | GLU | 129 | 84.243 | 14.159 | 2.287 | 1.00 | 6.78 | R1 |
| ATOM | 1218 | CB | GLU | 129 | 83.905 | 14.558 | 3.712 | 1.00 | 10.53 | R1 |
| ATOM | 1219 | CG | GLU | 129 | 84.734 | 15.713 | 4.242 | 1.00 | 16.33 | R1 |
| ATOM | 1220 | CD | GLU | 129 | 86.012 | 15.234 | 4.886 | 1.00 | 16.01 | R1 |
| ATOM | 1221 | OE1 | GLU | 129 | 87.097 | 15.714 | 4.505 | 1.00 | 19.28 | R1 |
| ATOM | 1222 | OE2 | GLU | 129 | 85.926 | 14.372 | 5.779 | 1.00 | 18.58 | R1 |
| ATOM | 1223 | C | GLU | 129 | 84.361 | 12.654 | 2.238 | 1.00 | 7.33 | R1 |
| ATOM | 1224 | O | GLU | 129 | 85.450 | 12.089 | 2.132 | 1.00 | 5.95 | R1 |
| ATOM | 1225 | N | PHE | 130 | 83.236 | 11.984 | 2.378 | 1.00 | 11.54 | R1 |
| ATOM | 1226 | H | PHE | 130 | 82.387 | 12.460 | 2.493 | 1.00 | 35.00 | R1 |
| ATOM | 1227 | CA | PHE | 130 | 83.257 | 10.541 | 2.349 | 1.00 | 13.12 | R1 |
| ATOM | 1228 | CB | PHE | 130 | 82.015 | 9.995 | 3.024 | 1.00 | 13.20 | R1 |
| ATOM | 1229 | CG | PHE | 130 | 81.845 | 10.517 | 4.413 | 1.00 | 12.76 | R1 |
| ATOM | 1230 | CD1 | PHE | 130 | 80.741 | 11.268 | 4.754 | 1.00 | 11.13 | R1 |
| ATOM | 1231 | CD2 | PHE | 130 | 82.825 | 10.294 | 5.364 | 1.00 | 12.59 | R1 |
| ATOM | 1232 | CE1 | PHE | 130 | 80.615 | 11.788 | 6.015 | 1.00 | 12.13 | R1 |
| ATOM | 1233 | CE2 | PHE | 130 | 82.704 | 10.811 | 6.627 | 1.00 | 14.73 | R1 |
| ATOM | 1234 | CZ | PHE | 130 | 81.596 | 11.561 | 6.957 | 1.00 | 13.33 | R1 |
| ATOM | 1235 | C | PHE | 130 | 83.471 | 10.013 | 0.955 | 1.00 | 12.32 | R1 |
| ATOM | 1236 | O | PHE | 130 | 83.846 | 8.863 | 0.790 | 1.00 | 15.85 | R1 |
| ATOM | 1237 | N | PHE | 131 | 83.250 | 10.851 | −0.052 | 1.00 | 14.03 | R1 |
| ATOM | 1238 | H | PHE | 131 | 82.896 | 11.744 | 0.130 | 1.00 | 35.00 | R1 |
| ATOM | 1239 | CA | PHE | 131 | 83.509 | 10.440 | −1.431 | 1.00 | 16.64 | R1 |
| ATOM | 1240 | CB | PHE | 131 | 82.473 | 10.996 | −2.397 | 1.00 | 10.03 | R1 |
| ATOM | 1241 | CG | PHE | 131 | 81.110 | 10.411 | −2.186 | 1.00 | 6.94 | R1 |
| ATOM | 1242 | CD1 | PHE | 131 | 80.101 | 11.151 | −1.577 | 1.00 | 5.71 | R1 |
| ATOM | 1243 | CD2 | PHE | 131 | 80.852 | 9.102 | −2.524 | 1.00 | 4.03 | R1 |
| ATOM | 1244 | CE1 | PHE | 131 | 78.878 | 10.599 | −1.312 | 1.00 | 2.00 | R1 |
| ATOM | 1245 | CE2 | PHE | 131 | 79.613 | 8.542 | −2.255 | 1.00 | 4.43 | R1 |
| ATOM | 1246 | CZ | PHE | 131 | 78.634 | 9.293 | −1.651 | 1.00 | 2.71 | R1 |
| ATOM | 1247 | C | PHE | 131 | 84.923 | 10.876 | −1.762 | 1.00 | 21.77 | R1 |
| ATOM | 1248 | O | PHE | 131 | 85.528 | 10.394 | −2.710 | 1.00 | 22.64 | R1 |
| ATOM | 1249 | N | LYS | 132 | 85.466 | 11.747 | −0.913 | 1.00 | 30.46 | R1 |
| ATOM | 1250 | H | LYS | 132 | 84.934 | 12.090 | −0.168 | 1.00 | 35.00 | R1 |
| ATOM | 1251 | CA | LYS | 132 | 86.849 | 12.208 | −1.034 | 1.00 | 37.05 | R1 |
| ATOM | 1252 | CB | LYS | 132 | 87.201 | 13.172 | 0.115 | 1.00 | 37.78 | R1 |
| ATOM | 1253 | CG | LYS | 132 | 88.658 | 13.612 | 0.176 | 1.00 | 36.69 | R1 |
| ATOM | 1254 | CD | LYS | 132 | 89.075 | 14.047 | 1.579 | 1.00 | 37.58 | R1 |
| ATOM | 1255 | CE | LYS | 132 | 89.443 | 12.841 | 2.459 | 1.00 | 36.77 | R1 |
| ATOM | 1256 | NZ | LYS | 132 | 90.220 | 13.197 | 3.704 | 1.00 | 32.91 | R1 |

TABLE 3-continued

Crystallographic coordinates for the refined co-crystal

| ATOM | 1257 | HZ1  | LYS | 132 | 90.465 | 12.333 | 4.229  | 1.00 | 35.00 | R1 |
|------|------|------|-----|-----|--------|--------|--------|------|-------|-----|
| ATOM | 1258 | HZ2  | LYS | 132 | 89.650 | 13.824 | 4.307  | 1.00 | 35.00 | R1 |
| ATOM | 1259 | HZ3  | LYS | 132 | 91.099 | 13.686 | 3.434  | 1.00 | 35.00 | R1 |
| ATOM | 1260 | C    | LYS | 132 | 87.671 | 10.932 | −0.876 | 1.00 | 42.16 | R1 |
| ATOM | 1261 | O    | LYS | 132 | 88.806 | 10.857 | −1.335 | 1.00 | 43.54 | R1 |
| ATOM | 1262 | N    | ASN | 133 | 87.074 | 9.950  | −0.190 | 1.00 | 47.92 | R1 |
| ATOM | 1263 | H    | ASN | 133 | 86.186 | 10.110 | 0.189  | 1.00 | 35.00 | R1 |
| ATOM | 1264 | CA   | ASN | 133 | 87.683 | 8.646  | 0.063  | 1.00 | 51.18 | R1 |
| ATOM | 1265 | CB   | ASN | 133 | 86.716 | 7.714  | 0.836  | 1.00 | 54.39 | R1 |
| ATOM | 1266 | CG   | ASN | 133 | 86.723 | 7.945  | 2.370  | 1.00 | 55.20 | R1 |
| ATOM | 1267 | OD1  | ASN | 133 | 87.422 | 8.823  | 2.897  | 1.00 | 56.18 | R1 |
| ATOM | 1268 | ND2  | ASN | 133 | 85.932 | 7.139  | 3.084  | 1.00 | 55.45 | R1 |
| ATOM | 1269 | HD21 | ASN | 133 | 85.397 | 6.472  | 2.603  | 1.00 | 35.00 | R1 |
| ATOM | 1270 | HD22 | ASN | 133 | 85.919 | 7.241  | 4.059  | 1.00 | 35.00 | R1 |
| ATOM | 1271 | C    | ASN | 133 | 88.061 | 8.032  | −1.279 | 1.00 | 51.70 | R1 |
| ATOM | 1272 | O    | ASN | 133 | 87.366 | 7.154  | −1.814 | 1.00 | 49.94 | R1 |
| ATOM | 1273 | N    | GLU | 134 | 89.179 | 8.524  | −1.806 | 1.00 | 51.11 | R1 |
| ATOM | 1274 | H    | GLU | 134 | 89.701 | 9.164  | −1.281 | 1.00 | 35.00 | R1 |
| ATOM | 1275 | CA   | GLU | 134 | 89.723 | 8.098  | −3.077 | 1.00 | 51.60 | R1 |
| ATOM | 1276 | CB   | GLU | 134 | 89.165 | 8.943  | −4.223 | 1.00 | 53.54 | R1 |
| ATOM | 1277 | CG   | GLU | 134 | 87.708 | 8.640  | −4.570 | 1.00 | 59.06 | R1 |
| ATOM | 1278 | CD   | GLU | 134 | 87.224 | 9.352  | −5.826 | 1.00 | 60.91 | R1 |
| ATOM | 1279 | OE1  | GLU | 134 | 86.380 | 8.773  | −6.554 | 1.00 | 61.29 | R1 |
| ATOM | 1280 | OE2  | GLU | 134 | 87.688 | 10.487 | −6.085 | 1.00 | 62.09 | R1 |
| ATOM | 1281 | C    | GLU | 134 | 91.217 | 8.284  | −2.971 | 1.00 | 50.62 | R1 |
| ATOM | 1282 | O    | GLU | 134 | 91.805 | 9.128  | −3.664 | 1.00 | 50.43 | R1 |
| ATOM | 1283 | N    | ASN | 135 | 91.813 | 7.509  | −2.057 | 1.00 | 49.32 | R1 |
| ATOM | 1284 | H    | ASN | 135 | 91.263 | 6.891  | −1.533 | 1.00 | 35.00 | R1 |
| ATOM | 1285 | CA   | ASN | 135 | 93.258 | 7.531  | −1.797 | 1.00 | 47.86 | R1 |
| ATOM | 1286 | CB   | ASN | 135 | 94.058 | 7.348  | −3.111 | 1.00 | 46.95 | R1 |
| ATOM | 1287 | CG   | ASN | 135 | 93.771 | 6.010  | −3.831 | 1.00 | 44.33 | R1 |
| ATOM | 1288 | OD1  | ASN | 135 | 94.604 | 5.542  | −4.619 | 1.00 | 41.17 | R1 |
| ATOM | 1289 | ND2  | ASN | 135 | 92.596 | 5.413  | −3.582 | 1.00 | 41.48 | R1 |
| ATOM | 1290 | HD21 | ASN | 135 | 91.927 | 5.791  | −2.984 | 1.00 | 35.00 | R1 |
| ATOM | 1291 | HD22 | ASN | 135 | 92.458 | 4.563  | −4.050 | 1.00 | 35.00 | R1 |
| ATOM | 1292 | C    | ASN | 135 | 93.726 | 8.819  | −1.078 | 1.00 | 45.66 | R1 |
| ATOM | 1293 | O    | ASN | 135 | 94.935 | 9.032  | −0.944 | 1.00 | 44.22 | R1 |
| ATOM | 1294 | N    | ASN | 136 | 92.757 | 9.668  | −0.692 | 1.00 | 43.18 | R1 |
| ATOM | 1295 | H    | ASN | 136 | 91.836 | 9.425  | −0.913 | 1.00 | 35.00 | R1 |
| ATOM | 1296 | CA   | ASN | 136 | 92.931 | 10.944 | 0.028  | 1.00 | 41.13 | R1 |
| ATOM | 1297 | CB   | ASN | 136 | 94.375 | 11.182 | 0.474  | 1.00 | 43.89 | R1 |
| ATOM | 1298 | CG   | ASN | 136 | 94.635 | 10.712 | 1.898  | 1.00 | 47.12 | R1 |
| ATOM | 1299 | OD1  | ASN | 136 | 95.792 | 10.645 | 2.342  | 1.00 | 48.71 | R1 |
| ATOM | 1300 | ND2  | ASN | 136 | 93.560 | 10.396 | 2.631  | 1.00 | 48.85 | R1 |
| ATOM | 1301 | HD21 | ASN | 136 | 92.647 | 10.459 | 2.288  | 1.00 | 35.00 | R1 |
| ATOM | 1302 | HD22 | ASN | 136 | 93.752 | 10.095 | 3.542  | 1.00 | 35.00 | R1 |
| ATOM | 1303 | C    | ASN | 136 | 92.429 | 12.223 | −0.631 | 1.00 | 39.47 | R1 |
| ATOM | 1304 | O    | ASN | 136 | 92.222 | 13.234 | 0.052  | 1.00 | 38.22 | R1 |
| ATOM | 1305 | N    | GLU | 137 | 92.198 | 12.181 | −1.939 | 1.00 | 35.69 | R1 |
| ATOM | 1306 | H    | GLU | 137 | 92.318 | 11.330 | −2.408 | 1.00 | 35.00 | R1 |
| ATOM | 1307 | CA   | GLU | 137 | 91.771 | 13.375 | −2.668 | 1.00 | 30.56 | R1 |
| ATOM | 1308 | CB   | GLU | 137 | 92.676 | 13.571 | −3.876 | 1.00 | 29.24 | R1 |
| ATOM | 1309 | CG   | GLU | 137 | 92.996 | 12.279 | −4.622 | 1.00 | 23.77 | R1 |
| ATOM | 1310 | CD   | GLU | 137 | 94.286 | 12.387 | −5.398 | 1.00 | 22.39 | R1 |
| ATOM | 1311 | OE1  | GLU | 137 | 95.021 | 11.377 | −5.476 | 1.00 | 16.86 | R1 |
| ATOM | 1312 | OE2  | GLU | 137 | 94.572 | 13.492 | −5.912 | 1.00 | 17.59 | R1 |
| ATOM | 1313 | C    | GLU | 137 | 90.295 | 13.558 | −3.049 | 1.00 | 28.74 | R1 |
| ATOM | 1314 | O    | GLU | 137 | 89.578 | 12.625 | −3.409 | 1.00 | 24.02 | R1 |
| ATOM | 1315 | N    | LEU | 138 | 89.863 | 14.805 | −2.964 | 1.00 | 26.82 | R1 |
| ATOM | 1316 | H    | LEU | 138 | 90.497 | 15.497 | −2.683 | 1.00 | 35.00 | R1 |
| ATOM | 1317 | CA   | LEU | 138 | 88.499 | 15.185 | −3.262 | 1.00 | 27.45 | R1 |
| ATOM | 1318 | CB   | LEU | 138 | 88.318 | 16.643 | −2.842 | 1.00 | 27.72 | R1 |
| ATOM | 1319 | CG   | LEU | 138 | 86.921 | 17.098 | −2.460 | 1.00 | 29.09 | R1 |
| ATOM | 1320 | CD1  | LEU | 138 | 86.213 | 15.971 | −1.751 | 1.00 | 30.45 | R1 |
| ATOM | 1321 | CD2  | LEU | 138 | 87.018 | 18.330 | −1.576 | 1.00 | 27.89 | R1 |
| ATOM | 1322 | C    | LEU | 138 | 88.258 | 15.008 | −4.751 | 1.00 | 26.54 | R1 |
| ATOM | 1323 | O    | LEU | 138 | 88.976 | 15.594 | −5.554 | 1.00 | 29.07 | R1 |
| ATOM | 1324 | N    | PRO | 139 | 87.230 | 14.214 | −5.141 | 1.00 | 24.68 | R1 |
| ATOM | 1325 | CD   | PRO | 139 | 86.234 | 13.618 | −4.226 | 1.00 | 24.41 | R1 |
| ATOM | 1326 | CA   | PRO | 139 | 86.857 | 13.927 | −6.539 | 1.00 | 24.42 | R1 |
| ATOM | 1327 | CB   | PRO | 139 | 85.464 | 13.315 | −6.403 | 1.00 | 19.77 | R1 |
| ATOM | 1328 | CG   | PRO | 139 | 85.520 | 12.629 | −5.115 | 1.00 | 19.42 | R1 |
| ATOM | 1329 | C    | PRO | 139 | 86.811 | 15.136 | −7.466 | 1.00 | 22.37 | R1 |
| ATOM | 1330 | O    | PRO | 139 | 86.379 | 16.222 | −7.083 | 1.00 | 23.94 | R1 |
| ATOM | 1331 | N    | LYS | 140 | 87.275 | 14.941 | −8.691 | 1.00 | 22.02 | R1 |
| ATOM | 1332 | H    | LYS | 140 | 87.633 | 14.061 | −8.931 | 1.00 | 35.00 | R1 |
| ATOM | 1333 | CA   | LYS | 140 | 87.260 | 16.004 | −9.683 | 1.00 | 19.37 | R1 |

TABLE 3-continued

Crystallographic coordinates for the refined co-crystal

| ATOM | 1334 | CB | LYS | 140 | 87.730 | 15.463 | −11.032 | 1.00 | 22.78 | R1 |
|------|------|------|-----|-----|--------|--------|---------|------|-------|----|
| ATOM | 1335 | CG | LYS | 140 | 87.859 | 16.519 | −12.125 | 1.00 | 28.77 | R1 |
| ATOM | 1336 | CD | LYS | 140 | 87.618 | 15.920 | −13.506 | 1.00 | 30.49 | R1 |
| ATOM | 1337 | CE | LYS | 140 | 88.434 | 14.652 | −13.727 | 1.00 | 33.31 | R1 |
| ATOM | 1338 | NZ | LYS | 140 | 89.904 | 14.882 | −13.606 | 1.00 | 30.97 | R1 |
| ATOM | 1339 | HZ1 | LYS | 140 | 90.399 | 13.983 | −13.772 | 1.00 | 35.00 | R1 |
| ATOM | 1340 | HZ2 | LYS | 140 | 90.125 | 15.233 | −12.652 | 1.00 | 35.00 | R1 |
| ATOM | 1341 | HZ3 | LYS | 140 | 90.198 | 15.585 | −14.313 | 1.00 | 35.00 | R1 |
| ATOM | 1342 | C | LYS | 140 | 85.810 | 16.480 | −9.786 | 1.00 | 13.54 | R1 |
| ATOM | 1343 | O | LYS | 140 | 84.882 | 15.684 | −9.670 | 1.00 | 11.63 | R1 |
| ATOM | 1344 | N | LEU | 141 | 85.624 | 17.774 | −9.985 | 1.00 | 8.16 | R1 |
| ATOM | 1345 | H | LEU | 141 | 86.402 | 18.363 | −10.072 | 1.00 | 35.00 | R1 |
| ATOM | 1346 | CA | LEU | 141 | 84.289 | 18.336 | −10.074 | 1.00 | 6.13 | R1 |
| ATOM | 1347 | CB | LEU | 141 | 84.034 | 19.257 | −8.875 | 1.00 | 2.00 | R1 |
| ATOM | 1348 | CG | LEU | 141 | 84.092 | 18.662 | −7.481 | 1.00 | 3.93 | R1 |
| ATOM | 1349 | CD1 | LEU | 141 | 83.757 | 19.800 | −6.549 | 1.00 | 2.00 | R1 |
| ATOM | 1350 | CD2 | LEU | 141 | 83.127 | 17.436 | −7.281 | 1.00 | 2.00 | R1 |
| ATOM | 1351 | C | LEU | 141 | 83.897 | 19.106 | −11.343 | 1.00 | 4.92 | R1 |
| ATOM | 1352 | O | LEU | 141 | 84.720 | 19.800 | −11.976 | 1.00 | 2.00 | R1 |
| ATOM | 1353 | N | GLN | 142 | 82.594 | 19.059 | −11.618 | 1.00 | 2.69 | R1 |
| ATOM | 1354 | H | GLN | 142 | 82.016 | 18.595 | −10.996 | 1.00 | 35.00 | R1 |
| ATOM | 1355 | CA | GLN | 142 | 82.000 | 19.768 | −12.740 | 1.00 | 6.97 | R1 |
| ATOM | 1356 | CB | GLN | 142 | 81.463 | 18.791 | −13.810 | 1.00 | 8.92 | R1 |
| ATOM | 1357 | CG | GLN | 142 | 82.480 | 18.165 | −14.748 | 1.00 | 11.53 | R1 |
| ATOM | 1358 | CD | GLN | 142 | 83.352 | 17.098 | −14.094 | 1.00 | 15.00 | R1 |
| ATOM | 1359 | OE1 | GLN | 142 | 82.902 | 15.983 | −13.773 | 1.00 | 9.77 | R1 |
| ATOM | 1360 | NE2 | GLN | 142 | 84.630 | 17.419 | −13.946 | 1.00 | 17.39 | R1 |
| ATOM | 1361 | HE21 | GLN | 142 | 84.947 | 18.291 | −14.259 | 1.00 | 35.00 | R1 |
| ATOM | 1362 | HE22 | GLN | 142 | 85.196 | 16.749 | −13.515 | 1.00 | 35.00 | R1 |
| ATOM | 1363 | C | GLN | 142 | 80.864 | 20.677 | −12.191 | 1.00 | 3.24 | R1 |
| ATOM | 1364 | O | GLN | 142 | 79.954 | 20.233 | −11.500 | 1.00 | 2.29 | R1 |
| ATOM | 1365 | N | TRP | 143 | 80.889 | 21.933 | −12.582 | 1.00 | 2.00 | R1 |
| ATOM | 1366 | H | TRP | 143 | 81.592 | 22.225 | −13.198 | 1.00 | 35.00 | R1 |
| ATOM | 1367 | CA | TRP | 143 | 79.923 | 22.897 | −12.127 | 1.00 | 2.00 | R1 |
| ATOM | 1368 | CB | TRP | 143 | 80.685 | 24.079 | −11.519 | 1.00 | 5.00 | R1 |
| ATOM | 1369 | CG | TRP | 143 | 81.317 | 23.765 | −10.188 | 1.00 | 6.38 | R1 |
| ATOM | 1370 | CD2 | TRP | 143 | 80.684 | 23.841 | −8.907 | 1.00 | 7.08 | R1 |
| ATOM | 1371 | CE2 | TRP | 143 | 81.664 | 23.540 | −7.939 | 1.00 | 7.53 | R1 |
| ATOM | 1372 | CE3 | TRP | 143 | 79.384 | 24.146 | −8.484 | 1.00 | 3.63 | R1 |
| ATOM | 1373 | CD1 | TRP | 143 | 82.606 | 23.413 | −9.956 | 1.00 | 5.74 | R1 |
| ATOM | 1374 | NE1 | TRP | 143 | 82.827 | 23.281 | −8.608 | 1.00 | 8.47 | R1 |
| ATOM | 1375 | HE1 | TRP | 143 | 83.682 | 23.038 | −8.191 | 1.00 | 35.00 | R1 |
| ATOM | 1376 | CZ2 | TRP | 143 | 81.391 | 23.535 | −6.570 | 1.00 | 10.47 | R1 |
| ATOM | 1377 | CZ3 | TRP | 143 | 79.108 | 24.145 | −7.114 | 1.00 | 8.28 | R1 |
| ATOM | 1378 | CH2 | TRP | 143 | 80.106 | 23.843 | −6.176 | 1.00 | 10.44 | R1 |
| ATOM | 1379 | C | TRP | 143 | 78.911 | 23.433 | −13.154 | 1.00 | 3.68 | R1 |
| ATOM | 1380 | O | TRP | 143 | 79.281 | 23.981 | −14.174 | 1.00 | 7.63 | R1 |
| ATOM | 1381 | N | TYR | 144 | 77.632 | 23.330 | −12.830 | 1.00 | 3.18 | R1 |
| ATOM | 1382 | H | TYR | 144 | 77.405 | 22.904 | −11.980 | 1.00 | 35.00 | R1 |
| ATOM | 1383 | CA | TYR | 144 | 76.557 | 23.819 | −13.664 | 1.00 | 2.00 | R1 |
| ATOM | 1384 | CB | TYR | 144 | 75.598 | 22.704 | −14.008 | 1.00 | 2.00 | R1 |
| ATOM | 1385 | CG | TYR | 144 | 76.246 | 21.544 | −14.673 | 1.00 | 2.00 | R1 |
| ATOM | 1386 | CD1 | TYR | 144 | 77.265 | 20.856 | −14.052 | 1.00 | 3.34 | R1 |
| ATOM | 1387 | CE1 | TYR | 144 | 77.889 | 19.803 | −14.681 | 1.00 | 2.78 | R1 |
| ATOM | 1388 | CD2 | TYR | 144 | 75.862 | 21.144 | −15.936 | 1.00 | 2.00 | R1 |
| ATOM | 1389 | CE2 | TYR | 144 | 76.478 | 20.098 | −16.557 | 1.00 | 2.00 | R1 |
| ATOM | 1390 | CZ | TYR | 144 | 77.489 | 19.433 | −15.926 | 1.00 | 2.00 | R1 |
| ATOM | 1391 | OH | TYR | 144 | 78.113 | 18.377 | −16.523 | 1.00 | 3.20 | R1 |
| ATOM | 1392 | HH | TYR | 144 | 78.813 | 18.040 | −15.959 | 1.00 | 35.00 | R1 |
| ATOM | 1393 | C | TYR | 144 | 75.764 | 24.854 | −12.894 | 1.00 | 7.82 | R1 |
| ATOM | 1394 | O | TYR | 144 | 75.727 | 24.838 | −11.653 | 1.00 | 10.34 | R1 |
| ATOM | 1395 | N | LYS | 145 | 75.146 | 25.758 | −13.644 | 1.00 | 6.71 | R1 |
| ATOM | 1396 | H | LYS | 145 | 75.277 | 25.722 | −14.614 | 1.00 | 35.00 | R1 |
| ATOM | 1397 | CA | LYS | 145 | 74.293 | 26.802 | −13.113 | 1.00 | 3.83 | R1 |
| ATOM | 1398 | CB | LYS | 145 | 74.838 | 28.179 | −13.484 | 1.00 | 2.00 | R1 |
| ATOM | 1399 | CG | LYS | 145 | 73.942 | 29.321 | −13.045 | 1.00 | 2.66 | R1 |
| ATOM | 1400 | CD | LYS | 145 | 74.677 | 30.656 | −13.082 | 1.00 | 3.79 | R1 |
| ATOM | 1401 | CE | LYS | 145 | 73.753 | 31.839 | −12.924 | 1.00 | 2.00 | R1 |
| ATOM | 1402 | NZ | LYS | 145 | 72.859 | 31.964 | −14.098 | 1.00 | 5.91 | R1 |
| ATOM | 1403 | HZ1 | LYS | 145 | 72.202 | 32.761 | −13.950 | 1.00 | 35.00 | R1 |
| ATOM | 1404 | HZ2 | LYS | 145 | 72.301 | 31.094 | −14.220 | 1.00 | 35.00 | R1 |
| ATOM | 1405 | HZ3 | LYS | 145 | 73.426 | 32.141 | −14.950 | 1.00 | 35.00 | R1 |
| ATOM | 1406 | C | LYS | 145 | 72.973 | 26.521 | −13.835 | 1.00 | 10.25 | R1 |
| ATOM | 1407 | O | LYS | 145 | 72.958 | 26.262 | −15.034 | 1.00 | 8.86 | R1 |
| ATOM | 1408 | N | ASP | 146 | 71.877 | 26.480 | −13.104 | 1.00 | 9.15 | R1 |
| ATOM | 1409 | H | ASP | 146 | 71.921 | 26.643 | −12.139 | 1.00 | 35.00 | R1 |
| ATOM | 1410 | CA | ASP | 146 | 70.612 | 26.197 | −13.739 | 1.00 | 9.53 | R1 |

TABLE 3-continued

Crystallographic coordinates for the refined co-crystal

| ATOM | 1411 | CB | ASP | 146 | 70.043 | 27.461 | −14.311 | 1.00 | 12.75 | R1 |
|---|---|---|---|---|---|---|---|---|---|---|
| ATOM | 1412 | CG | ASP | 146 | 69.660 | 28.418 | −13.244 | 1.00 | 19.05 | R1 |
| ATOM | 1413 | OD1 | ASP | 146 | 68.853 | 28.002 | −12.382 | 1.00 | 23.34 | R1 |
| ATOM | 1414 | OD2 | ASP | 146 | 70.174 | 29.562 | −13.241 | 1.00 | 18.49 | R1 |
| ATOM | 1415 | C | ASP | 146 | 70.705 | 25.083 | −14.782 | 1.00 | 10.02 | R1 |
| ATOM | 1416 | O | ASP | 146 | 70.114 | 25.150 | −15.852 | 1.00 | 9.64 | R1 |
| ATOM | 1417 | N | CYS | 147 | 71.507 | 24.079 | −14.444 | 1.00 | 8.51 | R1 |
| ATOM | 1418 | H | CYS | 147 | 71.984 | 24.129 | −13.588 | 1.00 | 35.00 | R1 |
| ATOM | 1419 | CA | CYS | 147 | 71.709 | 22.901 | −15.250 | 1.00 | 3.81 | R1 |
| ATOM | 1420 | C | CYS | 147 | 72.582 | 23.102 | −16.461 | 1.00 | 4.45 | R1 |
| ATOM | 1421 | O | CYS | 147 | 72.948 | 22.136 | −17.112 | 1.00 | 2.00 | R1 |
| ATOM | 1422 | CB | CYS | 147 | 70.370 | 22.329 | −15.639 | 1.00 | 3.95 | R1 |
| ATOM | 1423 | SG | CYS | 147 | 69.356 | 21.946 | −14.196 | 1.00 | 2.00 | R1 |
| ATOM | 1424 | N | LYS | 148 | 72.954 | 24.350 | −16.737 | 1.00 | 5.87 | R1 |
| ATOM | 1425 | H | LYS | 148 | 72.566 | 25.046 | −16.217 | 1.00 | 35.00 | R1 |
| ATOM | 1426 | CA | LYS | 148 | 73.793 | 24.681 | −17.893 | 1.00 | 6.84 | R1 |
| ATOM | 1427 | CB | LYS | 148 | 73.389 | 26.045 | −18.462 | 1.00 | 8.79 | R1 |
| ATOM | 1428 | CG | LYS | 148 | 71.931 | 26.085 | −18.963 | 1.00 | 11.56 | R1 |
| ATOM | 1429 | CD | LYS | 148 | 71.217 | 27.368 | −18.512 | 1.00 | 12.73 | R1 |
| ATOM | 1430 | CE | LYS | 148 | 69.698 | 27.231 | −18.562 | 1.00 | 8.58 | R1 |
| ATOM | 1431 | NZ | LYS | 148 | 69.063 | 28.549 | −18.293 | 1.00 | 7.31 | R1 |
| ATOM | 1432 | HZ1 | LYS | 148 | 68.030 | 28.438 | −18.324 | 1.00 | 35.00 | R1 |
| ATOM | 1433 | HZ2 | LYS | 148 | 69.358 | 29.239 | −19.012 | 1.00 | 35.00 | R1 |
| ATOM | 1434 | HZ3 | LYS | 148 | 69.348 | 28.879 | −17.348 | 1.00 | 35.00 | R1 |
| ATOM | 1435 | C | LYS | 148 | 75.263 | 24.679 | −17.537 | 1.00 | 5.62 | R1 |
| ATOM | 1436 | O | LYS | 148 | 75.720 | 25.571 | −16.847 | 1.00 | 2.00 | R1 |
| ATOM | 1437 | N | PRO | 149 | 76.046 | 23.746 | −18.117 | 1.00 | 2.38 | R1 |
| ATOM | 1438 | CD | PRO | 149 | 75.637 | 23.013 | −19.327 | 1.00 | 6.44 | R1 |
| ATOM | 1439 | CA | PRO | 149 | 77.491 | 23.572 | −17.896 | 1.00 | 2.00 | R1 |
| ATOM | 1440 | CB | PRO | 149 | 77.929 | 22.702 | −19.084 | 1.00 | 2.71 | R1 |
| ATOM | 1441 | CG | PRO | 149 | 76.926 | 22.990 | −20.125 | 1.00 | 3.25 | R1 |
| ATOM | 1442 | C | PRO | 149 | 78.292 | 24.859 | −17.815 | 1.00 | 4.08 | R1 |
| ATOM | 1443 | O | PRO | 149 | 77.949 | 25.862 | −18.438 | 1.00 | 5.17 | R1 |
| ATOM | 1444 | N | LEU | 150 | 79.366 | 24.828 | −17.037 | 1.00 | 2.76 | R1 |
| ATOM | 1445 | H | LEU | 150 | 79.598 | 24.003 | −16.559 | 1.00 | 35.00 | R1 |
| ATOM | 1446 | CA | LEU | 150 | 80.196 | 26.002 | −16.874 | 1.00 | 2.00 | R1 |
| ATOM | 1447 | CB | LEU | 150 | 80.113 | 26.550 | −15.441 | 1.00 | 4.75 | R1 |
| ATOM | 1448 | CG | LEU | 150 | 78.747 | 26.819 | −14.812 | 1.00 | 2.00 | R1 |
| ATOM | 1449 | CD1 | LEU | 150 | 78.927 | 26.745 | −13.326 | 1.00 | 4.37 | R1 |
| ATOM | 1450 | CD2 | LEU | 150 | 78.178 | 28.156 | −15.246 | 1.00 | 3.68 | R1 |
| ATOM | 1451 | C | LEU | 150 | 81.622 | 25.668 | −17.185 | 1.00 | 2.00 | R1 |
| ATOM | 1452 | O | LEU | 150 | 82.038 | 24.529 | −17.153 | 1.00 | 2.00 | R1 |
| ATOM | 1453 | N | LEU | 151 | 82.387 | 26.701 | −17.444 | 1.00 | 2.00 | R1 |
| ATOM | 1454 | H | LEU | 151 | 82.011 | 27.605 | −17.424 | 1.00 | 35.00 | R1 |
| ATOM | 1455 | CA | LEU | 151 | 83.770 | 26.530 | −17.770 | 1.00 | 4.69 | R1 |
| ATOM | 1456 | CB | LEU | 151 | 83.984 | 26.840 | −19.264 | 1.00 | 2.34 | R1 |
| ATOM | 1457 | CG | LEU | 151 | 85.348 | 26.963 | −19.921 | 1.00 | 2.00 | R1 |
| ATOM | 1458 | CD1 | LEU | 151 | 85.582 | 28.439 | −20.139 | 1.00 | 2.00 | R1 |
| ATOM | 1459 | CD2 | LEU | 151 | 86.476 | 26.290 | −19.140 | 1.00 | 2.00 | R1 |
| ATOM | 1460 | C | LEU | 151 | 84.472 | 27.491 | −16.838 | 1.00 | 2.89 | R1 |
| ATOM | 1461 | O | LEU | 151 | 84.178 | 28.691 | −16.810 | 1.00 | 2.00 | R1 |
| ATOM | 1462 | N | LEU | 152 | 85.334 | 26.915 | −16.013 | 1.00 | 2.00 | R1 |
| ATOM | 1463 | H | LEU | 152 | 85.481 | 25.948 | −16.088 | 1.00 | 35.00 | R1 |
| ATOM | 1464 | CA | LEU | 152 | 86.063 | 27.671 | −15.040 | 1.00 | 2.00 | R1 |
| ATOM | 1465 | CB | LEU | 152 | 86.507 | 26.769 | −13.916 | 1.00 | 2.44 | R1 |
| ATOM | 1466 | CG | LEU | 152 | 85.657 | 25.580 | −13.503 | 1.00 | 3.59 | R1 |
| ATOM | 1467 | CD1 | LEU | 152 | 86.534 | 24.601 | −12.684 | 1.00 | 2.00 | R1 |
| ATOM | 1468 | CD2 | LEU | 152 | 84.425 | 26.056 | −12.763 | 1.00 | 2.00 | R1 |
| ATOM | 1469 | C | LEU | 152 | 87.252 | 28.221 | −15.735 | 1.00 | 2.00 | R1 |
| ATOM | 1470 | O | LEU | 152 | 88.293 | 27.571 | −15.813 | 1.00 | 2.00 | R1 |
| ATOM | 1471 | N | ASP | 153 | 87.098 | 29.415 | −16.277 | 1.00 | 4.40 | R1 |
| ATOM | 1472 | H | ASP | 153 | 86.230 | 29.858 | −16.188 | 1.00 | 35.00 | R1 |
| ATOM | 1473 | CA | ASP | 153 | 88.206 | 30.032 | −16.988 | 1.00 | 9.42 | R1 |
| ATOM | 1474 | CB | ASP | 153 | 87.748 | 30.592 | −18.327 | 1.00 | 9.97 | R1 |
| ATOM | 1475 | CG | ASP | 153 | 86.510 | 31.465 | −18.214 | 1.00 | 16.92 | R1 |
| ATOM | 1476 | OD1 | ASP | 153 | 86.024 | 31.727 | −17.075 | 1.00 | 11.01 | R1 |
| ATOM | 1477 | OD2 | ASP | 153 | 86.017 | 31.871 | −19.303 | 1.00 | 16.81 | R1 |
| ATOM | 1478 | C | ASP | 153 | 89.016 | 31.077 | −16.239 | 1.00 | 11.38 | R1 |
| ATOM | 1479 | O | ASP | 153 | 89.858 | 31.722 | −16.838 | 1.00 | 12.90 | R1 |
| ATOM | 1480 | N | ASN | 154 | 88.822 | 31.203 | −14.931 | 1.00 | 11.08 | R1 |
| ATOM | 1481 | H | ASN | 154 | 88.180 | 30.616 | −14.484 | 1.00 | 35.00 | R1 |
| ATOM | 1482 | CA | ASN | 154 | 89.556 | 32.188 | −14.161 | 1.00 | 9.55 | R1 |
| ATOM | 1483 | CB | ASN | 154 | 91.067 | 31.915 | −14.239 | 1.00 | 16.13 | R1 |
| ATOM | 1484 | CG | ASN | 154 | 91.517 | 30.819 | −13.273 | 1.00 | 22.35 | R1 |
| ATOM | 1485 | OD1 | ASN | 154 | 91.342 | 30.949 | −12.059 | 1.00 | 26.03 | R1 |
| ATOM | 1486 | ND2 | ASN | 154 | 92.095 | 29.734 | −13.804 | 1.00 | 22.45 | R1 |
| ATOM | 1487 | HD21 | ASN | 154 | 92.205 | 29.702 | −14.777 | 1.00 | 35.00 | R1 |

TABLE 3-continued

Crystallographic coordinates for the refined co-crystal

| ATOM | 1488 | HD22 | ASN | 154 | 92.376 | 29.021 | −13.193 | 1.00 | 35.00 | R1 |
|---|---|---|---|---|---|---|---|---|---|---|
| ATOM | 1489 | C | ASN | 154 | 89.219 | 33.629 | −14.576 | 1.00 | 9.50 | R1 |
| ATOM | 1490 | O | ASN | 154 | 89.975 | 34.562 | −14.331 | 1.00 | 7.72 | R1 |
| ATOM | 1491 | N | ILE | 155 | 88.107 | 33.809 | −15.266 | 1.00 | 9.85 | R1 |
| ATOM | 1492 | H | ILE | 155 | 87.554 | 33.048 | −15.530 | 1.00 | 35.00 | R1 |
| ATOM | 1493 | CA | ILE | 155 | 87.708 | 35.161 | −15.626 | 1.00 | 12.93 | R1 |
| ATOM | 1494 | CB | ILE | 155 | 88.158 | 35.609 | −17.075 | 1.00 | 12.38 | R1 |
| ATOM | 1495 | CG2 | ILE | 155 | 89.019 | 34.572 | −17.762 | 1.00 | 5.69 | R1 |
| ATOM | 1496 | CG1 | ILE | 155 | 86.966 | 36.035 | −17.911 | 1.00 | 11.49 | R1 |
| ATOM | 1497 | CD1 | ILE | 155 | 86.113 | 34.917 | −18.309 | 1.00 | 14.03 | R1 |
| ATOM | 1498 | C | ILE | 155 | 86.220 | 35.400 | −15.292 | 1.00 | 13.57 | R1 |
| ATOM | 1499 | O | ILE | 155 | 85.816 | 36.524 | −14.975 | 1.00 | 13.93 | R1 |
| ATOM | 1500 | N | HIS | 156 | 85.437 | 34.317 | −15.318 | 1.00 | 14.31 | R1 |
| ATOM | 1501 | H | HIS | 156 | 85.841 | 33.466 | −15.587 | 1.00 | 35.00 | R1 |
| ATOM | 1502 | CA | HIS | 156 | 84.013 | 34.332 | −14.953 | 1.00 | 9.59 | R1 |
| ATOM | 1503 | CB | HIS | 156 | 83.128 | 33.873 | −16.112 | 1.00 | 10.10 | R1 |
| ATOM | 1504 | CG | HIS | 156 | 83.183 | 34.762 | −17.319 | 1.00 | 12.71 | R1 |
| ATOM | 1505 | CD2 | HIS | 156 | 83.174 | 36.111 | −17.442 | 1.00 | 14.39 | R1 |
| ATOM | 1506 | ND1 | HIS | 156 | 83.232 | 34.270 | −18.605 | 1.00 | 10.36 | R1 |
| ATOM | 1507 | HD1 | HIS | 156 | 83.270 | 33.321 | −18.851 | 1.00 | 35.00 | R1 |
| ATOM | 1508 | CE1 | HIS | 156 | 83.244 | 35.272 | −19.465 | 1.00 | 7.24 | R1 |
| ATOM | 1509 | NE2 | HIS | 156 | 83.212 | 36.400 | −18.786 | 1.00 | 6.60 | R1 |
| ATOM | 1510 | HE2 | HIS | 156 | 83.210 | 37.303 | −19.161 | 1.00 | 35.00 | R1 |
| ATOM | 1511 | C | HIS | 156 | 83.871 | 33.355 | −13.756 | 1.00 | 9.08 | R1 |
| ATOM | 1512 | O | HIS | 156 | 83.217 | 33.664 | −12.762 | 1.00 | 7.77 | R1 |
| ATOM | 1513 | N | PHE | 157 | 84.523 | 32.199 | −13.838 | 1.00 | 2.66 | R1 |
| ATOM | 1514 | H | PHE | 157 | 85.055 | 31.991 | −14.633 | 1.00 | 35.00 | R1 |
| ATOM | 1515 | CA | PHE | 157 | 84.463 | 31.231 | −12.761 | 1.00 | 3.04 | R1 |
| ATOM | 1516 | CB | PHE | 157 | 83.478 | 30.132 | −13.097 | 1.00 | 2.00 | R1 |
| ATOM | 1517 | CG | PHE | 157 | 82.055 | 30.617 | −13.243 | 1.00 | 7.60 | R1 |
| ATOM | 1518 | CD1 | PHE | 157 | 81.450 | 30.684 | −14.502 | 1.00 | 2.94 | R1 |
| ATOM | 1519 | CD2 | PHE | 157 | 81.312 | 31.012 | −12.123 | 1.00 | 5.67 | R1 |
| ATOM | 1520 | CE1 | PHE | 157 | 80.158 | 31.125 | −14.650 | 1.00 | 2.00 | R1 |
| ATOM | 1521 | CE2 | PHE | 157 | 80.003 | 31.458 | −12.274 | 1.00 | 3.50 | R1 |
| ATOM | 1522 | CZ | PHE | 157 | 79.433 | 31.512 | −13.542 | 1.00 | 2.61 | R1 |
| ATOM | 1523 | C | PHE | 157 | 85.822 | 30.650 | −12.393 | 1.00 | 7.02 | R1 |
| ATOM | 1524 | O | PHE | 157 | 86.840 | 31.061 | −12.936 | 1.00 | 11.03 | R1 |
| ATOM | 1525 | N | SER | 158 | 85.854 | 29.780 | −11.389 | 1.00 | 7.83 | R1 |
| ATOM | 1526 | H | SER | 158 | 85.025 | 29.559 | −10.914 | 1.00 | 35.00 | R1 |
| ATOM | 1527 | CA | SER | 158 | 87.096 | 29.138 | −10.970 | 1.00 | 8.21 | R1 |
| ATOM | 1528 | CB | SER | 158 | 88.031 | 30.155 | −10.329 | 1.00 | 12.62 | R1 |
| ATOM | 1529 | OG | SER | 158 | 87.638 | 30.470 | −9.014 | 1.00 | 17.14 | R1 |
| ATOM | 1530 | HG | SER | 158 | 87.692 | 29.688 | −8.461 | 1.00 | 35.00 | R1 |
| ATOM | 1531 | C | SER | 158 | 86.804 | 28.025 | −9.988 | 1.00 | 7.25 | R1 |
| ATOM | 1532 | O | SER | 158 | 85.779 | 28.067 | −9.323 | 1.00 | 5.14 | R1 |
| ATOM | 1533 | N | GLY | 159 | 87.695 | 27.032 | −9.917 | 1.00 | 8.96 | R1 |
| ATOM | 1534 | H | GLY | 159 | 88.477 | 27.054 | −10.508 | 1.00 | 35.00 | R1 |
| ATOM | 1535 | CA | GLY | 159 | 87.532 | 25.909 | −8.998 | 1.00 | 6.95 | R1 |
| ATOM | 1536 | C | GLY | 159 | 88.790 | 25.176 | −8.510 | 1.00 | 7.81 | R1 |
| ATOM | 1537 | O | GLY | 159 | 89.857 | 25.217 | −9.112 | 1.00 | 10.16 | R1 |
| ATOM | 1538 | N | VAL | 160 | 88.656 | 24.521 | −7.368 | 1.00 | 10.72 | R1 |
| ATOM | 1539 | H | VAL | 160 | 87.783 | 24.574 | −6.926 | 1.00 | 35.00 | R1 |
| ATOM | 1540 | CA | VAL | 160 | 89.719 | 23.726 | −6.734 | 1.00 | 12.79 | R1 |
| ATOM | 1541 | CB | VAL | 160 | 90.814 | 24.589 | −6.060 | 1.00 | 12.49 | R1 |
| ATOM | 1542 | CG1 | VAL | 160 | 91.945 | 24.852 | −7.043 | 1.00 | 13.72 | R1 |
| ATOM | 1543 | CG2 | VAL | 160 | 90.216 | 25.908 | −5.509 | 1.00 | 9.98 | R1 |
| ATOM | 1544 | C | VAL | 160 | 88.981 | 22.938 | −5.671 | 1.00 | 9.83 | R1 |
| ATOM | 1545 | O | VAL | 160 | 88.245 | 23.511 | −4.879 | 1.00 | 11.45 | R1 |
| ATOM | 1546 | N | LYS | 161 | 89.094 | 21.620 | −5.719 | 1.00 | 12.34 | R1 |
| ATOM | 1547 | H | LYS | 161 | 89.661 | 21.211 | −6.405 | 1.00 | 35.00 | R1 |
| ATOM | 1548 | CA | LYS | 161 | 88.379 | 20.758 | −4.784 | 1.00 | 14.05 | R1 |
| ATOM | 1549 | CB | LYS | 161 | 88.978 | 20.881 | −3.376 | 1.00 | 16.94 | R1 |
| ATOM | 1550 | CG | LYS | 161 | 90.461 | 20.555 | −3.290 | 1.00 | 19.45 | R1 |
| ATOM | 1551 | CD | LYS | 161 | 91.154 | 21.420 | −2.239 | 1.00 | 21.07 | R1 |
| ATOM | 1552 | CE | LYS | 161 | 92.632 | 21.065 | −2.121 | 1.00 | 23.47 | R1 |
| ATOM | 1553 | NZ | LYS | 161 | 93.331 | 21.795 | −1.022 | 1.00 | 24.59 | R1 |
| ATOM | 1554 | HZ1 | LYS | 161 | 94.325 | 21.490 | −0.998 | 1.00 | 35.00 | R1 |
| ATOM | 1555 | HZ2 | LYS | 161 | 92.881 | 21.576 | −0.110 | 1.00 | 35.00 | R1 |
| ATOM | 1556 | HZ3 | LYS | 161 | 93.278 | 22.818 | −1.202 | 1.00 | 35.00 | R1 |
| ATOM | 1557 | C | LYS | 161 | 86.897 | 21.169 | −4.785 | 1.00 | 11.32 | R1 |
| ATOM | 1558 | O | LYS | 161 | 86.394 | 21.732 | −5.761 | 1.00 | 13.03 | R1 |
| ATOM | 1559 | N | ASP | 162 | 86.237 | 20.970 | −3.651 | 1.00 | 9.70 | R1 |
| ATOM | 1560 | H | ASP | 162 | 86.693 | 20.554 | −2.894 | 1.00 | 35.00 | R1 |
| ATOM | 1561 | CA | ASP | 162 | 84.832 | 21.296 | −3.468 | 1.00 | 4.24 | R1 |
| ATOM | 1562 | CB | ASP | 162 | 84.382 | 20.782 | −2.125 | 1.00 | 5.88 | R1 |
| ATOM | 1563 | CG | ASP | 162 | 85.132 | 21.421 | −0.979 | 1.00 | 3.71 | R1 |
| ATOM | 1564 | OD1 | ASP | 162 | 86.252 | 21.944 | −1.186 | 1.00 | 2.00 | R1 |

TABLE 3-continued

Crystallographic coordinates for the refined co-crystal

| ATOM | 1565 | OD2 | ASP | 162 | 84.590 | 21.381 | 0.143 | 1.00 | 5.29 | R1 |
|---|---|---|---|---|---|---|---|---|---|---|
| ATOM | 1566 | C | ASP | 162 | 84.421 | 22.758 | −3.569 | 1.00 | 3.28 | R1 |
| ATOM | 1567 | O | ASP | 162 | 83.262 | 23.075 | −3.284 | 1.00 | 2.00 | R1 |
| ATOM | 1568 | N | ARG | 163 | 85.348 | 23.647 | −3.920 | 1.00 | 2.00 | R1 |
| ATOM | 1569 | H | ARG | 163 | 86.272 | 23.364 | −4.065 | 1.00 | 35.00 | R1 |
| ATOM | 1570 | CA | ARG | 163 | 85.000 | 25.059 | −4.061 | 1.00 | 5.19 | R1 |
| ATOM | 1571 | CB | ARG | 163 | 86.109 | 25.958 | −3.492 | 1.00 | 10.27 | R1 |
| ATOM | 1572 | CG | ARG | 163 | 85.882 | 26.433 | −2.037 | 1.00 | 13.72 | R1 |
| ATOM | 1573 | CD | ARG | 163 | 86.587 | 27.773 | −1.733 | 1.00 | 13.73 | R1 |
| ATOM | 1574 | NE | ARG | 163 | 87.976 | 27.810 | −2.212 | 1.00 | 15.88 | R1 |
| ATOM | 1575 | HE | ARG | 163 | 88.366 | 26.992 | −2.586 | 1.00 | 35.00 | R1 |
| ATOM | 1576 | CZ | ARG | 163 | 88.755 | 28.893 | −2.191 | 1.00 | 16.59 | R1 |
| ATOM | 1577 | NH1 | ARG | 163 | 88.304 | 30.051 | −1.704 | 1.00 | 18.08 | R1 |
| ATOM | 1578 | HH11 | ARG | 163 | 87.368 | 30.124 | −1.361 | 1.00 | 35.00 | R1 |
| ATOM | 1579 | HH12 | ARG | 163 | 88.900 | 30.855 | −1.710 | 1.00 | 35.00 | R1 |
| ATOM | 1580 | NH2 | ARG | 163 | 89.973 | 28.837 | −2.706 | 1.00 | 12.80 | R1 |
| ATOM | 1581 | HH21 | ARG | 163 | 90.306 | 27.986 | −3.112 | 1.00 | 35.00 | R1 |
| ATOM | 1582 | HH22 | ARG | 163 | 90.560 | 29.648 | −2.699 | 1.00 | 35.00 | R1 |
| ATOM | 1583 | C | ARG | 163 | 84.656 | 25.514 | −5.500 | 1.00 | 6.46 | R1 |
| ATOM | 1584 | O | ARG | 163 | 85.069 | 24.887 | −6.490 | 1.00 | 6.96 | R1 |
| ATOM | 1585 | N | LEU | 164 | 83.849 | 26.573 | −5.588 | 1.00 | 4.43 | R1 |
| ATOM | 1586 | H | LEU | 164 | 83.514 | 26.969 | −4.754 | 1.00 | 35.00 | R1 |
| ATOM | 1587 | CA | LEU | 164 | 83.447 | 27.181 | −6.859 | 1.00 | 5.99 | R1 |
| ATOM | 1588 | CB | LEU | 164 | 82.017 | 26.805 | −7.274 | 1.00 | 9.85 | R1 |
| ATOM | 1589 | CG | LEU | 164 | 81.483 | 27.630 | −8.489 | 1.00 | 12.93 | R1 |
| ATOM | 1590 | CD1 | LEU | 164 | 82.181 | 27.197 | −9.787 | 1.00 | 9.79 | R1 |
| ATOM | 1591 | CD2 | LEU | 164 | 79.970 | 27.525 | −8.658 | 1.00 | 7.23 | R1 |
| ATOM | 1592 | C | LEU | 164 | 83.447 | 28.667 | −6.610 | 1.00 | 2.49 | R1 |
| ATOM | 1593 | O | LEU | 164 | 82.767 | 29.108 | −5.698 | 1.00 | 2.00 | R1 |
| ATOM | 1594 | N | ILE | 165 | 84.168 | 29.437 | −7.421 | 1.00 | 2.00 | R1 |
| ATOM | 1595 | H | ILE | 165 | 84.666 | 29.038 | −8.151 | 1.00 | 35.00 | R1 |
| ATOM | 1596 | CA | ILE | 165 | 84.217 | 30.883 | −7.219 | 1.00 | 2.00 | R1 |
| ATOM | 1597 | CB | ILE | 165 | 85.644 | 31.418 | −6.996 | 1.00 | 2.00 | R1 |
| ATOM | 1598 | CG2 | ILE | 165 | 85.586 | 32.904 | −6.740 | 1.00 | 2.00 | R1 |
| ATOM | 1599 | CG1 | ILE | 165 | 86.314 | 30.693 | −5.831 | 1.00 | 2.00 | R1 |
| ATOM | 1600 | CD1 | ILE | 165 | 87.733 | 31.063 | −5.600 | 1.00 | 2.00 | R1 |
| ATOM | 1601 | C | ILE | 165 | 83.631 | 31.646 | −8.368 | 1.00 | 2.00 | R1 |
| ATOM | 1602 | O | ILE | 165 | 84.196 | 31.687 | −9.438 | 1.00 | 2.00 | R1 |
| ATOM | 1603 | N | VAL | 166 | 82.505 | 32.286 | −8.115 | 1.00 | 2.00 | R1 |
| ATOM | 1604 | H | VAL | 166 | 82.122 | 32.215 | −7.212 | 1.00 | 35.00 | R1 |
| ATOM | 1605 | CA | VAL | 166 | 81.815 | 33.072 | −9.111 | 1.00 | 2.00 | R1 |
| ATOM | 1606 | CB | VAL | 166 | 80.365 | 33.254 | −8.686 | 1.00 | 2.00 | R1 |
| ATOM | 1607 | CG1 | VAL | 166 | 79.633 | 34.126 | −9.667 | 1.00 | 4.46 | R1 |
| ATOM | 1608 | CG2 | VAL | 166 | 79.699 | 31.920 | −8.548 | 1.00 | 2.47 | R1 |
| ATOM | 1609 | C | VAL | 166 | 82.462 | 34.446 | −9.180 | 1.00 | 2.64 | R1 |
| ATOM | 1610 | O | VAL | 166 | 82.155 | 35.294 | −8.356 | 1.00 | 2.00 | R1 |
| ATOM | 1611 | N | MET | 167 | 83.379 | 34.657 | −10.125 | 1.00 | 5.52 | R1 |
| ATOM | 1612 | H | MET | 167 | 83.616 | 33.917 | −10.719 | 1.00 | 35.00 | R1 |
| ATOM | 1613 | CA | MET | 167 | 84.041 | 35.953 | −10.274 | 1.00 | 8.07 | R1 |
| ATOM | 1614 | CB | MET | 167 | 85.135 | 35.858 | −11.333 | 1.00 | 8.55 | R1 |
| ATOM | 1615 | CG | MET | 167 | 86.329 | 35.054 | −10.872 | 1.00 | 11.09 | R1 |
| ATOM | 1616 | SD | MET | 167 | 87.611 | 34.730 | −12.112 | 1.00 | 21.73 | R1 |
| ATOM | 1617 | CE | MET | 167 | 88.541 | 36.295 | −12.171 | 1.00 | 19.87 | R1 |
| ATOM | 1618 | C | MET | 167 | 82.990 | 37.015 | −10.613 | 1.00 | 9.79 | R1 |
| ATOM | 1619 | O | MET | 167 | 82.209 | 36.851 | −11.552 | 1.00 | 11.83 | R1 |
| ATOM | 1620 | N | ASN | 168 | 82.947 | 38.098 | −9.845 | 1.00 | 16.09 | R1 |
| ATOM | 1621 | H | ASN | 168 | 83.607 | 38.220 | −9.133 | 1.00 | 35.00 | R1 |
| ATOM | 1622 | CA | ASN | 168 | 81.912 | 39.106 | −10.067 | 1.00 | 22.65 | R1 |
| ATOM | 1623 | CB | ASN | 168 | 81.450 | 39.746 | −8.750 | 1.00 | 19.31 | R1 |
| ATOM | 1624 | CG | ASN | 168 | 79.941 | 39.995 | −8.718 | 1.00 | 21.60 | R1 |
| ATOM | 1625 | OD1 | ASN | 168 | 79.474 | 41.096 | −9.016 | 1.00 | 20.89 | R1 |
| ATOM | 1626 | ND2 | ASN | 168 | 79.171 | 38.963 | −8.357 | 1.00 | 20.26 | R1 |
| ATOM | 1627 | HD21 | ASN | 168 | 79.609 | 38.115 | −8.137 | 1.00 | 35.00 | R1 |
| ATOM | 1628 | HD22 | ASN | 168 | 78.199 | 39.094 | −8.327 | 1.00 | 35.00 | R1 |
| ATOM | 1629 | C | ASN | 168 | 82.178 | 40.165 | −11.111 | 1.00 | 27.62 | R1 |
| ATOM | 1630 | O | ASN | 168 | 83.139 | 40.948 | −11.032 | 1.00 | 26.94 | R1 |
| ATOM | 1631 | N | VAL | 169 | 81.300 | 40.163 | −12.109 | 1.00 | 34.63 | R1 |
| ATOM | 1632 | H | VAL | 169 | 80.585 | 39.493 | −12.114 | 1.00 | 35.00 | R1 |
| ATOM | 1633 | CA | VAL | 169 | 81.370 | 41.124 | −13.200 | 1.00 | 40.44 | R1 |
| ATOM | 1634 | CB | VAL | 169 | 81.918 | 40.461 | −14.522 | 1.00 | 42.88 | R1 |
| ATOM | 1635 | CG1 | VAL | 169 | 82.118 | 41.517 | −15.611 | 1.00 | 43.53 | R1 |
| ATOM | 1636 | CG2 | VAL | 169 | 83.260 | 39.744 | −14.258 | 1.00 | 41.25 | R1 |
| ATOM | 1637 | C | VAL | 169 | 79.941 | 41.672 | −13.352 | 1.00 | 41.70 | R1 |
| ATOM | 1638 | O | VAL | 169 | 79.045 | 40.965 | −13.826 | 1.00 | 39.90 | R1 |
| ATOM | 1639 | N | ALA | 170 | 79.748 | 42.894 | −12.834 | 1.00 | 41.83 | R1 |
| ATOM | 1640 | H | ALA | 170 | 80.528 | 43.327 | −12.428 | 1.00 | 35.00 | R1 |
| ATOM | 1641 | CA | ALA | 170 | 78.482 | 43.654 | −12.813 | 1.00 | 43.01 | R1 |

TABLE 3-continued

Crystallographic coordinates for the refined co-crystal

| ATOM | 1642 | CB | ALA | 170 | 78.652 | 44.974 | −13.566 | 1.00 | 39.62 | R1 |
|---|---|---|---|---|---|---|---|---|---|---|
| ATOM | 1643 | C | ALA | 170 | 77.203 | 42.938 | −13.261 | 1.00 | 46.18 | R1 |
| ATOM | 1644 | O | ALA | 170 | 76.731 | 43.150 | −14.385 | 1.00 | 48.68 | R1 |
| ATOM | 1645 | N | GLU | 171 | 76.616 | 42.134 | −12.366 | 1.00 | 47.75 | R1 |
| ATOM | 1646 | H | GLU | 171 | 76.999 | 42.052 | −11.468 | 1.00 | 35.00 | R1 |
| ATOM | 1647 | CA | GLU | 171 | 75.395 | 41.376 | −12.691 | 1.00 | 46.43 | R1 |
| ATOM | 1648 | CB | GLU | 171 | 75.665 | 40.519 | −13.942 | 1.00 | 46.97 | R1 |
| ATOM | 1649 | CG | GLU | 171 | 74.465 | 39.851 | −14.560 | 1.00 | 42.81 | R1 |
| ATOM | 1650 | CD | GLU | 171 | 74.853 | 38.626 | −15.330 | 1.00 | 41.37 | R1 |
| ATOM | 1651 | OE1 | GLU | 171 | 74.336 | 37.533 | −15.011 | 1.00 | 39.88 | R1 |
| ATOM | 1652 | OE2 | GLU | 171 | 75.688 | 38.761 | −16.246 | 1.00 | 42.06 | R1 |
| ATOM | 1653 | C | GLU | 171 | 74.815 | 40.470 | −11.570 | 1.00 | 45.32 | R1 |
| ATOM | 1654 | O | GLU | 171 | 75.415 | 40.288 | −10.493 | 1.00 | 44.36 | R1 |
| ATOM | 1655 | N | LYS | 172 | 73.618 | 39.946 | −11.850 | 1.00 | 41.47 | R1 |
| ATOM | 1656 | H | LYS | 172 | 73.159 | 40.206 | −12.671 | 1.00 | 35.00 | R1 |
| ATOM | 1657 | CA | LYS | 172 | 72.892 | 39.038 | −10.975 | 1.00 | 37.03 | R1 |
| ATOM | 1658 | CB | LYS | 172 | 71.387 | 39.286 | −11.095 | 1.00 | 36.35 | R1 |
| ATOM | 1659 | CG | LYS | 172 | 70.939 | 40.687 | −10.706 | 1.00 | 34.19 | R1 |
| ATOM | 1660 | CD | LYS | 172 | 69.415 | 40.829 | −10.709 | 1.00 | 30.47 | R1 |
| ATOM | 1661 | CE | LYS | 172 | 68.746 | 39.829 | −9.772 | 1.00 | 27.78 | R1 |
| ATOM | 1662 | NZ | LYS | 172 | 67.300 | 40.106 | −9.544 | 1.00 | 24.50 | R1 |
| ATOM | 1663 | HZ1 | LYS | 172 | 67.193 | 41.052 | −9.126 | 1.00 | 35.00 | R1 |
| ATOM | 1664 | HZ2 | LYS | 172 | 66.918 | 39.393 | −8.888 | 1.00 | 35.00 | R1 |
| ATOM | 1665 | HZ3 | LYS | 172 | 66.783 | 40.059 | −10.444 | 1.00 | 35.00 | R1 |
| ATOM | 1666 | C | LYS | 172 | 73.191 | 37.602 | −11.418 | 1.00 | 35.61 | R1 |
| ATOM | 1667 | O | LYS | 172 | 72.631 | 37.119 | −12.408 | 1.00 | 36.04 | R1 |
| ATOM | 1668 | N | HIS | 173 | 74.082 | 36.939 | −10.683 | 1.00 | 31.25 | R1 |
| ATOM | 1669 | H | HIS | 173 | 74.478 | 37.397 | −9.912 | 1.00 | 35.00 | R1 |
| ATOM | 1670 | CA | HIS | 173 | 74.489 | 35.564 | −10.959 | 1.00 | 25.34 | R1 |
| ATOM | 1671 | CB | HIS | 173 | 75.897 | 35.339 | −10.414 | 1.00 | 24.48 | R1 |
| ATOM | 1672 | CG | HIS | 173 | 76.957 | 36.089 | −11.151 | 1.00 | 26.05 | R1 |
| ATOM | 1673 | CD2 | HIS | 173 | 77.211 | 37.417 | −11.244 | 1.00 | 25.69 | R1 |
| ATOM | 1674 | ND1 | HIS | 173 | 77.916 | 35.460 | −11.918 | 1.00 | 24.47 | R1 |
| ATOM | 1675 | HD1 | HIS | 173 | 77.987 | 34.494 | −12.066 | 1.00 | 35.00 | R1 |
| ATOM | 1676 | CE1 | HIS | 173 | 78.715 | 36.367 | −12.449 | 1.00 | 26.01 | R1 |
| ATOM | 1677 | NE2 | HIS | 173 | 78.309 | 37.562 | −12.055 | 1.00 | 26.23 | R1 |
| ATOM | 1678 | HE2 | HIS | 173 | 78.719 | 38.417 | −12.306 | 1.00 | 35.00 | R1 |
| ATOM | 1679 | C | HIS | 173 | 73.560 | 34.492 | −10.367 | 1.00 | 24.34 | R1 |
| ATOM | 1680 | O | HIS | 173 | 73.870 | 33.302 | −10.423 | 1.00 | 25.07 | R1 |
| ATOM | 1681 | N | ARG | 174 | 72.440 | 34.907 | −9.785 | 1.00 | 21.91 | R1 |
| ATOM | 1682 | H | ARG | 174 | 72.260 | 35.869 | −9.772 | 1.00 | 35.00 | R1 |
| ATOM | 1683 | CA | ARG | 174 | 71.493 | 33.984 | −9.174 | 1.00 | 17.90 | R1 |
| ATOM | 1684 | CB | ARG | 174 | 70.162 | 34.673 | −8.929 | 1.00 | 23.30 | R1 |
| ATOM | 1685 | CG | ARG | 174 | 70.246 | 36.067 | −8.373 | 1.00 | 30.35 | R1 |
| ATOM | 1686 | CD | ARG | 174 | 68.874 | 36.721 | −8.366 | 1.00 | 33.71 | R1 |
| ATOM | 1687 | NE | ARG | 174 | 67.904 | 35.988 | −7.555 | 1.00 | 36.89 | R1 |
| ATOM | 1688 | HE | ARG | 174 | 67.963 | 35.010 | −7.513 | 1.00 | 35.00 | R1 |
| ATOM | 1689 | CZ | ARG | 174 | 66.935 | 36.573 | −6.860 | 1.00 | 38.97 | R1 |
| ATOM | 1690 | NH1 | ARG | 174 | 66.815 | 37.896 | −6.882 | 1.00 | 37.63 | R1 |
| ATOM | 1691 | HH11 | ARG | 174 | 67.448 | 38.454 | −7.417 | 1.00 | 35.00 | R1 |
| ATOM | 1692 | HH12 | ARG | 174 | 66.088 | 38.337 | −6.354 | 1.00 | 35.00 | R1 |
| ATOM | 1693 | NH2 | ARG | 174 | 66.100 | 35.844 | −6.130 | 1.00 | 37.19 | R1 |
| ATOM | 1694 | HH21 | ARG | 174 | 66.206 | 34.850 | −6.098 | 1.00 | 35.00 | R1 |
| ATOM | 1695 | HH22 | ARG | 174 | 65.376 | 36.286 | −5.601 | 1.00 | 35.00 | R1 |
| ATOM | 1696 | C | ARG | 174 | 71.214 | 32.731 | −9.998 | 1.00 | 13.70 | R1 |
| ATOM | 1697 | O | ARG | 174 | 71.191 | 32.757 | −11.222 | 1.00 | 13.52 | R1 |
| ATOM | 1698 | N | GLY | 175 | 70.978 | 31.638 | −9.296 | 1.00 | 9.36 | R1 |
| ATOM | 1699 | H | GLY | 175 | 71.033 | 31.675 | −8.318 | 1.00 | 35.00 | R1 |
| ATOM | 1700 | CA | GLY | 175 | 70.673 | 30.385 | −9.934 | 1.00 | 4.02 | R1 |
| ATOM | 1701 | C | GLY | 175 | 70.888 | 29.241 | −8.972 | 1.00 | 4.99 | R1 |
| ATOM | 1702 | O | GLY | 175 | 71.444 | 29.397 | −7.880 | 1.00 | 3.55 | R1 |
| ATOM | 1703 | N | ASN | 176 | 70.397 | 28.080 | −9.363 | 1.00 | 4.05 | R1 |
| ATOM | 1704 | H | ASN | 176 | 69.909 | 28.018 | −10.210 | 1.00 | 35.00 | R1 |
| ATOM | 1705 | CA | ASN | 176 | 70.577 | 26.914 | −8.563 | 1.00 | 2.00 | R1 |
| ATOM | 1706 | CB | ASN | 176 | 69.371 | 26.017 | −8.687 | 1.00 | 6.68 | R1 |
| ATOM | 1707 | CG | ASN | 176 | 68.246 | 26.440 | −7.785 | 1.00 | 8.51 | R1 |
| ATOM | 1708 | OD1 | ASN | 176 | 67.065 | 26.344 | −8.147 | 1.00 | 9.48 | R1 |
| ATOM | 1709 | ND2 | ASN | 176 | 68.598 | 26.874 | −6.583 | 1.00 | 9.70 | R1 |
| ATOM | 1710 | HD21 | ASN | 176 | 69.551 | 26.883 | −6.362 | 1.00 | 35.00 | R1 |
| ATOM | 1711 | HD22 | ASN | 176 | 67.939 | 27.167 | −5.936 | 1.00 | 35.00 | R1 |
| ATOM | 1712 | C | ASN | 176 | 71.763 | 26.237 | −9.177 | 1.00 | 5.41 | R1 |
| ATOM | 1713 | O | ASN | 176 | 71.653 | 25.717 | −10.289 | 1.00 | 11.63 | R1 |
| ATOM | 1714 | N | TYR | 177 | 72.918 | 26.319 | −8.514 | 1.00 | 4.96 | R1 |
| ATOM | 1715 | H | TYR | 177 | 72.953 | 26.829 | −7.678 | 1.00 | 35.00 | R1 |
| ATOM | 1716 | CA | TYR | 177 | 74.134 | 25.669 | −9.014 | 1.00 | 4.58 | R1 |
| ATOM | 1717 | CB | TYR | 177 | 75.384 | 26.392 | −8.585 | 1.00 | 2.00 | R1 |
| ATOM | 1718 | CG | TYR | 177 | 75.585 | 27.706 | −9.257 | 1.00 | 2.00 | R1 |

TABLE 3-continued

Crystallographic coordinates for the refined co-crystal

| ATOM | 1719 | CD1 | TYR | 177 | 74.672 | 28.726 | −9.079 | 1.00 | 2.00 | R1 |
|---|---|---|---|---|---|---|---|---|---|---|
| ATOM | 1720 | CE1 | TYR | 177 | 74.913 | 29.974 | −9.562 | 1.00 | 2.27 | R1 |
| ATOM | 1721 | CD2 | TYR | 177 | 76.753 | 27.971 | −9.963 | 1.00 | 2.00 | R1 |
| ATOM | 1722 | CE2 | TYR | 177 | 77.005 | 29.216 | −10.453 | 1.00 | 2.96 | R1 |
| ATOM | 1723 | CZ | TYR | 177 | 76.076 | 30.221 | −10.241 | 1.00 | 3.98 | R1 |
| ATOM | 1724 | OH | TYR | 177 | 76.311 | 31.496 | −10.689 | 1.00 | 8.16 | R1 |
| ATOM | 1725 | HH | TYR | 177 | 77.145 | 31.522 | −11.166 | 1.00 | 35.00 | R1 |
| ATOM | 1726 | C | TYR | 177 | 74.234 | 24.225 | −8.589 | 1.00 | 2.00 | R1 |
| ATOM | 1727 | O | TYR | 177 | 73.783 | 23.862 | −7.531 | 1.00 | 2.00 | R1 |
| ATOM | 1728 | N | THR | 178 | 74.896 | 23.429 | −9.414 | 1.00 | 2.00 | R1 |
| ATOM | 1729 | H | THR | 178 | 75.333 | 23.800 | −10.194 | 1.00 | 35.00 | R1 |
| ATOM | 1730 | CA | THR | 178 | 75.025 | 22.013 | −9.188 | 1.00 | 2.00 | R1 |
| ATOM | 1731 | CB | THR | 178 | 74.271 | 21.242 | −10.336 | 1.00 | 4.03 | R1 |
| ATOM | 1732 | OG1 | THR | 178 | 73.037 | 20.685 | −9.856 | 1.00 | 2.00 | R1 |
| ATOM | 1733 | HG1 | THR | 178 | 72.439 | 21.409 | −9.644 | 1.00 | 35.00 | R1 |
| ATOM | 1734 | CG2 | THR | 178 | 75.146 | 20.141 | −10.976 | 1.00 | 5.08 | R1 |
| ATOM | 1735 | C | THR | 178 | 76.486 | 21.668 | −9.234 | 1.00 | 2.00 | R1 |
| ATOM | 1736 | O | THR | 178 | 77.221 | 22.279 | −9.990 | 1.00 | 2.00 | R1 |
| ATOM | 1737 | N | CYS | 179 | 76.916 | 20.756 | −8.357 | 1.00 | 2.95 | R1 |
| ATOM | 1738 | H | CYS | 179 | 76.299 | 20.372 | −7.709 | 1.00 | 35.00 | R1 |
| ATOM | 1739 | CA | CYS | 179 | 78.300 | 20.266 | −8.349 | 1.00 | 2.01 | R1 |
| ATOM | 1740 | C | CYS | 179 | 78.153 | 18.778 | −8.707 | 1.00 | 2.00 | R1 |
| ATOM | 1741 | O | CYS | 179 | 77.258 | 18.116 | −8.202 | 1.00 | 2.00 | R1 |
| ATOM | 1742 | CB | CYS | 179 | 79.030 | 20.544 | −7.013 | 1.00 | 2.40 | R1 |
| ATOM | 1743 | SG | CYS | 179 | 78.365 | 19.918 | −5.424 | 1.00 | 2.00 | R1 |
| ATOM | 1744 | N | HIS | 180 | 78.914 | 18.317 | −9.700 | 1.00 | 2.00 | R1 |
| ATOM | 1745 | H | HIS | 180 | 79.584 | 18.910 | −10.089 | 1.00 | 35.00 | R1 |
| ATOM | 1746 | CA | HIS | 180 | 78.800 | 16.945 | −10.204 | 1.00 | 3.57 | R1 |
| ATOM | 1747 | CB | HIS | 180 | 78.108 | 16.933 | −11.603 | 1.00 | 4.48 | R1 |
| ATOM | 1748 | CG | HIS | 180 | 77.941 | 15.568 | −12.221 | 1.00 | 2.00 | R1 |
| ATOM | 1749 | CD2 | HIS | 180 | 76.873 | 14.737 | −12.274 | 1.00 | 2.00 | R1 |
| ATOM | 1750 | ND1 | HIS | 180 | 78.944 | 14.937 | −12.934 | 1.00 | 5.82 | R1 |
| ATOM | 1751 | HD1 | HIS | 180 | 79.834 | 15.310 | −13.098 | 1.00 | 35.00 | R1 |
| ATOM | 1752 | CE1 | HIS | 180 | 78.504 | 13.777 | −13.393 | 1.00 | 2.00 | R1 |
| ATOM | 1753 | NE2 | HIS | 180 | 77.249 | 13.633 | −13.005 | 1.00 | 2.29 | R1 |
| ATOM | 1754 | HE2 | HIS | 180 | 76.689 | 12.854 | −13.203 | 1.00 | 35.00 | R1 |
| ATOM | 1755 | C | HIS | 180 | 80.170 | 16.358 | −10.296 | 1.00 | 2.00 | R1 |
| ATOM | 1756 | O | HIS | 180 | 81.115 | 17.025 | −10.716 | 1.00 | 2.00 | R1 |
| ATOM | 1757 | N | ALA | 181 | 80.241 | 15.093 | −9.916 | 1.00 | 2.00 | R1 |
| ATOM | 1758 | H | ALA | 181 | 79.415 | 14.657 | −9.622 | 1.00 | 35.00 | R1 |
| ATOM | 1759 | CA | ALA | 181 | 81.455 | 14.343 | −9.903 | 1.00 | 2.00 | R1 |
| ATOM | 1760 | CB | ALA | 181 | 82.172 | 14.637 | −8.669 | 1.00 | 3.25 | R1 |
| ATOM | 1761 | C | ALA | 181 | 81.044 | 12.896 | −9.904 | 1.00 | 6.10 | R1 |
| ATOM | 1762 | O | ALA | 181 | 79.879 | 12.579 | −9.659 | 1.00 | 7.48 | R1 |
| ATOM | 1763 | N | SER | 182 | 82.003 | 12.021 | −10.195 | 1.00 | 9.18 | R1 |
| ATOM | 1764 | H | SER | 182 | 82.897 | 12.359 | −10.413 | 1.00 | 35.00 | R1 |
| ATOM | 1765 | CA | SER | 182 | 81.782 | 10.576 | −10.221 | 1.00 | 9.23 | R1 |
| ATOM | 1766 | CB | SER | 182 | 82.190 | 10.019 | −11.594 | 1.00 | 7.55 | R1 |
| ATOM | 1767 | OG | SER | 182 | 82.584 | 8.651 | −11.542 | 1.00 | 2.00 | R1 |
| ATOM | 1768 | HG | SER | 182 | 81.874 | 8.120 | −11.171 | 1.00 | 35.00 | R1 |
| ATOM | 1769 | C | SER | 182 | 82.593 | 9.895 | −9.113 | 1.00 | 12.53 | R1 |
| ATOM | 1770 | O | SER | 182 | 83.767 | 10.219 | −8.906 | 1.00 | 13.47 | R1 |
| ATOM | 1771 | N | TYR | 183 | 81.961 | 8.993 | −8.368 | 1.00 | 13.89 | R1 |
| ATOM | 1772 | H | TYR | 183 | 81.025 | 8.829 | −8.508 | 1.00 | 35.00 | R1 |
| ATOM | 1773 | CA | TYR | 183 | 82.663 | 8.277 | −7.312 | 1.00 | 15.50 | R1 |
| ATOM | 1774 | CB | TYR | 183 | 81.899 | 8.351 | −5.982 | 1.00 | 16.92 | R1 |
| ATOM | 1775 | CG | TYR | 183 | 82.493 | 7.487 | −4.873 | 1.00 | 19.15 | R1 |
| ATOM | 1776 | CD1 | TYR | 183 | 83.673 | 7.849 | −4.221 | 1.00 | 17.00 | R1 |
| ATOM | 1777 | CE1 | TYR | 183 | 84.257 | 7.005 | −3.283 | 1.00 | 14.49 | R1 |
| ATOM | 1778 | CD2 | TYR | 183 | 81.914 | 6.264 | −4.537 | 1.00 | 18.02 | R1 |
| ATOM | 1779 | CE2 | TYR | 183 | 82.494 | 5.422 | −3.606 | 1.00 | 15.67 | R1 |
| ATOM | 1780 | CZ | TYR | 183 | 83.668 | 5.786 | −2.989 | 1.00 | 14.02 | R1 |
| ATOM | 1781 | OH | TYR | 183 | 84.289 | 4.880 | −2.156 | 1.00 | 9.34 | R1 |
| ATOM | 1782 | HH | TYR | 183 | 83.766 | 4.074 | −2.106 | 1.00 | 35.00 | R1 |
| ATOM | 1783 | C | TYR | 183 | 82.811 | 6.847 | −7.779 | 1.00 | 15.25 | R1 |
| ATOM | 1784 | O | TYR | 183 | 81.838 | 6.224 | −8.188 | 1.00 | 21.22 | R1 |
| ATOM | 1785 | N | THR | 184 | 84.037 | 6.347 | −7.795 | 1.00 | 14.86 | R1 |
| ATOM | 1786 | H | THR | 184 | 84.796 | 6.897 | −7.507 | 1.00 | 35.00 | R1 |
| ATOM | 1787 | CA | THR | 184 | 84.273 | 4.981 | −8.238 | 1.00 | 12.78 | R1 |
| ATOM | 1788 | CB | THR | 184 | 85.671 | 4.810 | −8.921 | 1.00 | 13.51 | R1 |
| ATOM | 1789 | OG1 | THR | 184 | 85.839 | 5.792 | −9.952 | 1.00 | 13.33 | R1 |
| ATOM | 1790 | HG1 | THR | 184 | 86.709 | 5.726 | −10.353 | 1.00 | 35.00 | R1 |
| ATOM | 1791 | CG2 | THR | 184 | 85.789 | 3.436 | −9.555 | 1.00 | 10.20 | R1 |
| ATOM | 1792 | C | THR | 184 | 84.179 | 4.099 | −7.016 | 1.00 | 10.29 | R1 |
| ATOM | 1793 | O | THR | 184 | 84.930 | 4.295 | −6.060 | 1.00 | 10.10 | R1 |
| ATOM | 1794 | N | TYR | 185 | 83.253 | 3.138 | −7.059 | 1.00 | 9.58 | R1 |
| ATOM | 1795 | H | TYR | 185 | 82.694 | 3.065 | −7.855 | 1.00 | 35.00 | R1 |

TABLE 3-continued

Crystallographic coordinates for the refined co-crystal

| ATOM | 1796 | CA | TYR | 185 | 83.006 | 2.196 | −5.966 | 1.00 | 8.72 | R1 |
| ATOM | 1797 | CB | TYR | 185 | 81.701 | 2.586 | −5.243 | 1.00 | 8.32 | R1 |
| ATOM | 1798 | CG | TYR | 185 | 81.413 | 1.795 | −3.998 | 1.00 | 2.34 | R1 |
| ATOM | 1799 | CD1 | TYR | 185 | 81.779 | 2.288 | −2.753 | 1.00 | 6.09 | R1 |
| ATOM | 1800 | CE1 | TYR | 185 | 81.519 | 1.581 | −1.598 | 1.00 | 5.82 | R1 |
| ATOM | 1801 | CD2 | TYR | 185 | 80.785 | 0.567 | −4.065 | 1.00 | 2.00 | R1 |
| ATOM | 1802 | CE2 | TYR | 185 | 80.523 | −0.154 | −2.935 | 1.00 | 4.47 | R1 |
| ATOM | 1803 | CZ | TYR | 185 | 80.884 | 0.366 | −1.699 | 1.00 | 4.83 | R1 |
| ATOM | 1804 | OH | TYR | 185 | 80.537 | −0.273 | −0.561 | 1.00 | 2.00 | R1 |
| ATOM | 1805 | HH | TYR | 185 | 80.122 | −1.103 | −0.808 | 1.00 | 35.00 | R1 |
| ATOM | 1806 | C | TYR | 185 | 82.899 | 0.745 | −6.463 | 1.00 | 11.07 | R1 |
| ATOM | 1807 | O | TYR | 185 | 82.021 | 0.422 | −7.277 | 1.00 | 12.52 | R1 |
| ATOM | 1808 | N | LEU | 186 | 83.741 | −0.128 | −5.906 | 1.00 | 12.21 | R1 |
| ATOM | 1809 | H | LEU | 186 | 84.354 | 0.200 | −5.214 | 1.00 | 35.00 | R1 |
| ATOM | 1810 | CA | LEU | 186 | 83.802 | −1.554 | −6.248 | 1.00 | 15.27 | R1 |
| ATOM | 1811 | CB | LEU | 186 | 82.576 | −2.316 | −5.732 | 1.00 | 14.61 | R1 |
| ATOM | 1812 | CG | LEU | 186 | 82.461 | −2.817 | −4.284 | 1.00 | 13.47 | R1 |
| ATOM | 1813 | CD1 | LEU | 186 | 81.981 | −4.250 | −4.329 | 1.00 | 7.67 | R1 |
| ATOM | 1814 | CD2 | LEU | 186 | 83.764 | −2.701 | −3.510 | 1.00 | 15.34 | R1 |
| ATOM | 1815 | C | LEU | 186 | 83.996 | −1.879 | −7.729 | 1.00 | 16.57 | R1 |
| ATOM | 1816 | O | LEU | 186 | 83.531 | −2.924 | −8.204 | 1.00 | 15.12 | R1 |
| ATOM | 1817 | N | GLY | 187 | 84.704 | −1.001 | −8.438 | 1.00 | 18.26 | R1 |
| ATOM | 1818 | H | GLY | 187 | 85.077 | −0.206 | −8.000 | 1.00 | 35.00 | R1 |
| ATOM | 1819 | CA | GLY | 187 | 84.946 | −1.206 | −9.855 | 1.00 | 19.44 | R1 |
| ATOM | 1820 | C | GLY | 187 | 84.061 | −0.425 | −10.816 | 1.00 | 18.50 | R1 |
| ATOM | 1821 | O | GLY | 187 | 84.416 | −0.288 | −12.002 | 1.00 | 19.85 | R1 |
| ATOM | 1822 | N | LYS | 188 | 82.907 | 0.052 | −10.349 | 1.00 | 15.31 | R1 |
| ATOM | 1823 | H | LYS | 188 | 82.648 | −0.115 | −9.419 | 1.00 | 35.00 | R1 |
| ATOM | 1824 | CA | LYS | 188 | 82.034 | 0.822 | −11.216 | 1.00 | 15.06 | R1 |
| ATOM | 1825 | CB | LYS | 188 | 80.614 | 0.253 | −11.239 | 1.00 | 18.43 | R1 |
| ATOM | 1826 | CG | LYS | 188 | 79.705 | 0.860 | −12.372 | 1.00 | 23.42 | R1 |
| ATOM | 1827 | CD | LYS | 188 | 79.914 | 0.266 | −13.821 | 1.00 | 23.31 | R1 |
| ATOM | 1828 | CE | LYS | 188 | 81.267 | 0.586 | −14.491 | 1.00 | 19.41 | R1 |
| ATOM | 1829 | NZ | LYS | 188 | 81.413 | 2.016 | −14.857 | 1.00 | 17.42 | R1 |
| ATOM | 1830 | HZ1 | LYS | 188 | 82.344 | 2.160 | −15.298 | 1.00 | 35.00 | R1 |
| ATOM | 1831 | HZ2 | LYS | 188 | 81.337 | 2.601 | −14.000 | 1.00 | 35.00 | R1 |
| ATOM | 1832 | HZ3 | LYS | 188 | 80.664 | 2.280 | −15.530 | 1.00 | 35.00 | R1 |
| ATOM | 1833 | C | LYS | 188 | 82.010 | 2.313 | −10.881 | 1.00 | 15.83 | R1 |
| ATOM | 1834 | O | LYS | 188 | 82.461 | 2.723 | −9.815 | 1.00 | 14.63 | R1 |
| ATOM | 1835 | N | GLN | 189 | 81.532 | 3.115 | −11.840 | 1.00 | 14.86 | R1 |
| ATOM | 1836 | H | GLN | 189 | 81.261 | 2.722 | −12.693 | 1.00 | 35.00 | R1 |
| ATOM | 1837 | CA | GLN | 189 | 81.421 | 4.563 | −11.711 | 1.00 | 13.19 | R1 |
| ATOM | 1838 | CB | GLN | 189 | 81.863 | 5.253 | −13.018 | 1.00 | 18.39 | R1 |
| ATOM | 1839 | CG | GLN | 189 | 83.369 | 5.181 | −13.369 | 1.00 | 26.32 | R1 |
| ATOM | 1840 | CD | GLN | 189 | 83.686 | 5.749 | −14.777 | 1.00 | 82.58 | R1 |
| ATOM | 1841 | OE1 | GLN | 189 | 83.076 | 6.739 | −15.207 | 1.00 | 38.80 | R1 |
| ATOM | 1842 | NE2 | GLN | 189 | 84.628 | 5.116 | −15.498 | 1.00 | 29.74 | R1 |
| ATOM | 1843 | HE21 | GLN | 189 | 85.071 | 4.332 | −15.113 | 1.00 | 35.00 | R1 |
| ATOM | 1844 | HE22 | GLN | 189 | 84.822 | 5.474 | −16.390 | 1.00 | 35.00 | R1 |
| ATOM | 1845 | C | GLN | 189 | 79.974 | 4.958 | −11.412 | 1.00 | 8.17 | R1 |
| ATOM | 1846 | O | GLN | 189 | 79.052 | 4.477 | −12.065 | 1.00 | 3.69 | R1 |
| ATOM | 1847 | N | TYR | 190 | 79.779 | 5.798 | −10.396 | 1.00 | 5.32 | R1 |
| ATOM | 1848 | H | TYR | 190 | 80.548 | 6.100 | −9.874 | 1.00 | 35.00 | R1 |
| ATOM | 1849 | CA | TYR | 190 | 78.445 | 6.278 | −10.033 | 1.00 | 3.72 | R1 |
| ATOM | 1850 | CB | TYR | 190 | 77.961 | 5.691 | −8.719 | 1.00 | 2.26 | R1 |
| ATOM | 1851 | CG | TYR | 190 | 78.046 | 4.206 | −8.582 | 1.00 | 2.30 | R1 |
| ATOM | 1852 | CD1 | TYR | 190 | 79.209 | 3.609 | −8.120 | 1.00 | 2.46 | R1 |
| ATOM | 1853 | CE1 | TYR | 190 | 79.264 | 2.258 | −7.903 | 1.00 | 7.26 | R1 |
| ATOM | 1854 | CD2 | TYR | 190 | 76.938 | 3.404 | −8.834 | 1.00 | 2.00 | R1 |
| ATOM | 1855 | CE2 | TYR | 190 | 76.980 | 2.059 | −8.623 | 1.00 | 2.00 | R1 |
| ATOM | 1856 | CZ | TYR | 190 | 78.141 | 1.482 | −8.152 | 1.00 | 7.34 | R1 |
| ATOM | 1857 | OH | TYR | 190 | 78.185 | 0.125 | −7.873 | 1.00 | 14.68 | R1 |
| ATOM | 1858 | HH | TYR | 190 | 77.350 | −0.288 | −8.100 | 1.00 | 35.00 | R1 |
| ATOM | 1859 | C | TYR | 190 | 78.541 | 7.768 | −9.812 | 1.00 | 3.04 | R1 |
| ATOM | 1860 | O | TYR | 190 | 79.436 | 8.222 | −9.094 | 1.00 | 3.59 | R1 |
| ATOM | 1861 | N | PRO | 191 | 77.586 | 8.537 | −10.358 | 1.00 | 2.00 | R1 |
| ATOM | 1862 | CD | PRO | 191 | 76.520 | 7.991 | −11.205 | 1.00 | 2.00 | R1 |
| ATOM | 1863 | CA | PRO | 191 | 77.470 | 9.992 | −10.276 | 1.00 | 2.00 | R1 |
| ATOM | 1864 | CB | PRO | 191 | 76.499 | 10.297 | −11.394 | 1.00 | 2.76 | R1 |
| ATOM | 1865 | CG | PRO | 191 | 75.575 | 9.141 | −11.319 | 1.00 | 2.00 | R1 |
| ATOM | 1866 | C | PRO | 191 | 76.932 | 10.517 | −8.927 | 1.00 | 5.45 | R1 |
| ATOM | 1867 | O | PRO | 191 | 76.252 | 9.810 | −8.157 | 1.00 | 4.87 | R1 |
| ATOM | 1868 | N | ILE | 192 | 77.284 | 11.761 | −8.627 | 1.00 | 4.42 | R1 |
| ATOM | 1869 | H | ILE | 192 | 77.836 | 12.261 | −9.259 | 1.00 | 35.00 | R1 |
| ATOM | 1870 | CA | ILE | 192 | 76.858 | 12.399 | −7.400 | 1.00 | 2.37 | R1 |
| ATOM | 1871 | CB | ILE | 192 | 77.913 | 12.352 | −6.309 | 1.00 | 2.00 | R1 |
| ATOM | 1872 | CG2 | ILE | 192 | 77.328 | 12.864 | −5.006 | 1.00 | 6.14 | R1 |

TABLE 3-continued

Crystallographic coordinates for the refined co-crystal

| ATOM | 1873 | CG1  | ILE | 192 | 78.371 | 10.943 | −6.049 | 1.00 | 2.00  | R1 |
|------|------|------|-----|-----|--------|--------|--------|------|-------|----|
| ATOM | 1874 | CD1  | ILE | 192 | 79.512 | 10.920 | −5.080 | 1.00 | 2.00  | R1 |
| ATOM | 1875 | C    | ILE | 192 | 76.673 | 13.844 | −7.753 | 1.00 | 2.00  | R1 |
| ATOM | 1876 | O    | ILE | 192 | 77.486 | 14.413 | −8.481 | 1.00 | 2.00  | R1 |
| ATOM | 1877 | N    | THR | 193 | 75.615 | 14.443 | −7.219 | 1.00 | 2.14  | R1 |
| ATOM | 1878 | H    | THR | 193 | 75.101 | 13.945 | −6.562 | 1.00 | 35.00 | R1 |
| ATOM | 1879 | CA   | THR | 193 | 75.320 | 15.836 | −7.499 | 1.00 | 5.78  | R1 |
| ATOM | 1880 | CB   | THR | 193 | 74.288 | 16.024 | −8.686 | 1.00 | 2.00  | R1 |
| ATOM | 1881 | OG1  | THR | 193 | 72.946 | 15.827 | −8.236 | 1.00 | 2.00  | R1 |
| ATOM | 1882 | HG1  | THR | 193 | 72.336 | 15.817 | −8.979 | 1.00 | 35.00 | R1 |
| ATOM | 1883 | CG2  | THR | 193 | 74.540 | 15.053 | −9.750 | 1.00 | 2.00  | R1 |
| ATOM | 1884 | C    | THR | 193 | 74.795 | 16.507 | −6.258 | 1.00 | 2.00  | R1 |
| ATOM | 1885 | O    | THR | 193 | 74.213 | 15.855 | −5.413 | 1.00 | 2.00  | R1 |
| ATOM | 1886 | N    | ARG | 194 | 74.998 | 17.816 | −6.187 | 1.00 | 2.00  | R1 |
| ATOM | 1887 | H    | ARG | 194 | 75.475 | 18.250 | −6.926 | 1.00 | 35.00 | R1 |
| ATOM | 1888 | CA   | ARG | 194 | 74.547 | 18.641 | −5.075 | 1.00 | 2.00  | R1 |
| ATOM | 1889 | CB   | ARG | 194 | 75.681 | 18.864 | −4.093 | 1.00 | 2.99  | R1 |
| ATOM | 1890 | CG   | ARG | 194 | 75.347 | 18.495 | −2.698 | 1.00 | 2.00  | R1 |
| ATOM | 1891 | CD   | ARG | 194 | 75.204 | 16.998 | −2.571 | 1.00 | 2.00  | R1 |
| ATOM | 1892 | NE   | ARG | 194 | 76.446 | 16.309 | −2.266 | 1.00 | 2.00  | R1 |
| ATOM | 1893 | HE   | ARG | 194 | 77.235 | 16.844 | −2.083 | 1.00 | 35.00 | R1 |
| ATOM | 1894 | CZ   | ARG | 194 | 76.561 | 14.987 | −2.295 | 1.00 | 2.38  | R1 |
| ATOM | 1895 | NH1  | ARG | 194 | 75.531 | 14.233 | −2.636 | 1.00 | 2.00  | R1 |
| ATOM | 1896 | HH11 | ARG | 194 | 74.655 | 14.649 | −2.883 | 1.00 | 35.00 | R1 |
| ATOM | 1897 | HH12 | ARG | 194 | 75.627 | 13.238 | −2.656 | 1.00 | 35.00 | R1 |
| ATOM | 1898 | NH2  | ARG | 194 | 77.672 | 14.402 | −1.882 | 1.00 | 7.21  | R1 |
| ATOM | 1899 | HH21 | ARG | 194 | 78.431 | 14.960 | −1.549 | 1.00 | 35.00 | R1 |
| ATOM | 1900 | HH22 | ARG | 194 | 77.749 | 13.406 | −1.908 | 1.00 | 35.00 | R1 |
| ATOM | 1901 | C    | ARG | 194 | 74.152 | 19.994 | −5.628 | 1.00 | 2.00  | R1 |
| ATOM | 1902 | O    | ARG | 194 | 74.891 | 20.562 | −6.447 | 1.00 | 2.00  | R1 |
| ATOM | 1903 | N    | VAL | 195 | 73.010 | 20.521 | −5.183 | 1.00 | 2.00  | R1 |
| ATOM | 1904 | H    | VAL | 195 | 72.482 | 20.020 | −4.524 | 1.00 | 35.00 | R1 |
| ATOM | 1905 | CA   | VAL | 195 | 72.541 | 21.826 | −5.658 | 1.00 | 2.55  | R1 |
| ATOM | 1906 | CB   | VAL | 195 | 71.079 | 21.821 | −6.149 | 1.00 | 2.00  | R1 |
| ATOM | 1907 | CG1  | VAL | 195 | 70.826 | 22.976 | −7.115 | 1.00 | 2.00  | R1 |
| ATOM | 1908 | CG2  | VAL | 195 | 70.767 | 20.533 | −6.791 | 1.00 | 3.41  | R1 |
| ATOM | 1909 | C    | VAL | 195 | 72.624 | 22.807 | −4.524 | 1.00 | 2.00  | R1 |
| ATOM | 1910 | O    | VAL | 195 | 72.479 | 22.440 | −3.389 | 1.00 | 3.44  | R1 |
| ATOM | 1911 | N    | ILE | 196 | 72.854 | 24.063 | −4.842 | 1.00 | 2.00  | R1 |
| ATOM | 1912 | H    | ILE | 196 | 72.968 | 24.316 | −5.775 | 1.00 | 35.00 | R1 |
| ATOM | 1913 | CA   | ILE | 196 | 72.944 | 25.069 | −3.826 | 1.00 | 3.23  | R1 |
| ATOM | 1914 | CB   | ILE | 196 | 74.413 | 25.383 | −3.472 | 1.00 | 2.00  | R1 |
| ATOM | 1915 | CG2  | ILE | 196 | 74.493 | 26.009 | −2.095 | 1.00 | 2.00  | R1 |
| ATOM | 1916 | CG1  | ILE | 196 | 75.283 | 24.149 | −3.608 | 1.00 | 2.00  | R1 |
| ATOM | 1917 | CD1  | ILE | 196 | 76.725 | 24.465 | −3.539 | 1.00 | 2.00  | R1 |
| ATOM | 1918 | C    | ILE | 196 | 72.359 | 26.347 | −4.417 | 1.00 | 5.30  | R1 |
| ATOM | 1919 | O    | ILE | 196 | 72.704 | 26.740 | −5.538 | 1.00 | 2.00  | R1 |
| ATOM | 1920 | N    | GLU | 197 | 71.511 | 27.019 | −3.650 | 1.00 | 6.50  | R1 |
| ATOM | 1921 | H    | GLU | 197 | 71.264 | 26.679 | −2.767 | 1.00 | 35.00 | R1 |
| ATOM | 1922 | CA   | GLU | 197 | 70.973 | 28.247 | −4.132 | 1.00 | 7.50  | R1 |
| ATOM | 1923 | CB   | GLU | 197 | 69.648 | 28.586 | −3.475 | 1.00 | 6.69  | R1 |
| ATOM | 1924 | CG   | GLU | 197 | 69.226 | 30.001 | −3.833 | 1.00 | 4.33  | R1 |
| ATOM | 1925 | CD   | GLU | 197 | 67.794 | 30.294 | −3.589 | 1.00 | 2.00  | R1 |
| ATOM | 1926 | OE1  | GLU | 197 | 66.954 | 29.470 | −3.946 | 1.00 | 2.00  | R1 |
| ATOM | 1927 | OE2  | GLU | 197 | 67.508 | 31.382 | −3.071 | 1.00 | 4.33  | R1 |
| ATOM | 1928 | C    | GLU | 197 | 71.937 | 29.375 | −3.893 | 1.00 | 11.90 | R1 |
| ATOM | 1929 | O    | GLU | 197 | 72.220 | 29.718 | −2.750 | 1.00 | 11.52 | R1 |
| ATOM | 1930 | N    | PHE | 198 | 72.437 | 29.958 | −4.981 | 1.00 | 20.00 | R1 |
| ATOM | 1931 | H    | PHE | 198 | 72.204 | 29.606 | −5.865 | 1.00 | 35.00 | R1 |
| ATOM | 1932 | CA   | PHE | 198 | 73.326 | 31.111 | −4.879 | 1.00 | 25.03 | R1 |
| ATOM | 1933 | CB   | PHE | 198 | 74.450 | 31.089 | −5.902 | 1.00 | 20.96 | R1 |
| ATOM | 1934 | CG   | PHE | 198 | 75.399 | 32.237 | −5.741 | 1.00 | 20.94 | R1 |
| ATOM | 1935 | CD1  | PHE | 198 | 76.420 | 32.183 | −4.792 | 1.00 | 18.43 | R1 |
| ATOM | 1936 | CD2  | PHE | 198 | 75.240 | 33.402 | −6.482 | 1.00 | 19.40 | R1 |
| ATOM | 1937 | CE1  | PHE | 198 | 77.252 | 33.261 | −4.586 | 1.00 | 14.89 | R1 |
| ATOM | 1938 | CE2  | PHE | 198 | 76.076 | 34.490 | −6.280 | 1.00 | 16.02 | R1 |
| ATOM | 1939 | CZ   | PHE | 198 | 77.082 | 34.419 | −5.331 | 1.00 | 15.61 | R1 |
| ATOM | 1940 | C    | PHE | 198 | 72.511 | 32.371 | −5.107 | 1.00 | 30.05 | R1 |
| ATOM | 1941 | O    | PHE | 198 | 72.119 | 32.654 | −6.231 | 1.00 | 33.56 | R1 |
| ATOM | 1942 | N    | ILE | 199 | 72.246 | 33.114 | −4.035 | 1.00 | 35.28 | R1 |
| ATOM | 1943 | H    | ILE | 199 | 72.579 | 32.826 | −3.159 | 1.00 | 35.00 | R1 |
| ATOM | 1944 | CA   | ILE | 199 | 71.478 | 34.347 | −4.127 | 1.00 | 37.23 | R1 |
| ATOM | 1945 | CB   | ILE | 199 | 70.627 | 34.584 | −2.852 | 1.00 | 36.26 | R1 |
| ATOM | 1946 | CG2  | ILE | 199 | 71.471 | 35.182 | −1.736 | 1.00 | 36.38 | R1 |
| ATOM | 1947 | CG1  | ILE | 199 | 69.485 | 35.546 | −3.155 | 1.00 | 38.18 | R1 |
| ATOM | 1948 | CD1  | ILE | 199 | 68.745 | 36.061 | −1.928 | 1.00 | 39.03 | R1 |
| ATOM | 1949 | C    | ILE | 199 | 72.466 | 35.485 | −4.272 | 1.00 | 38.82 | R1 |

TABLE 3-continued

Crystallographic coordinates for the refined co-crystal

| ATOM | 1950 | O   | ILE | 199 | 73.557 | 35.437 | -3.705 | 1.00 | 36.97 | R1 |
|------|------|-----|-----|-----|--------|--------|--------|------|-------|----|
| ATOM | 1951 | N   | THR | 200 | 72.090 | 36.500 | -5.041 | 1.00 | 43.47 | R1 |
| ATOM | 1952 | H   | THR | 200 | 71.215 | 36.470 | -5.482 | 1.00 | 35.00 | R1 |
| ATOM | 1953 | CA  | THR | 200 | 72.944 | 37.662 | -5.233 | 1.00 | 47.99 | R1 |
| ATOM | 1954 | CB  | THR | 200 | 72.219 | 38.758 | -6.032 | 1.00 | 45.55 | R1 |
| ATOM | 1955 | OG1 | THR | 200 | 70.837 | 38.807 | -5.654 | 1.00 | 41.98 | R1 |
| ATOM | 1956 | HG1 | THR | 200 | 70.375 | 39.442 | -6.207 | 1.00 | 35.00 | R1 |
| ATOM | 1957 | CG2 | THR | 200 | 72.333 | 38.483 | -7.513 | 1.00 | 44.63 | R1 |
| ATOM | 1958 | C   | THR | 200 | 73.322 | 38.159 | -3.844 | 1.00 | 52.86 | R1 |
| ATOM | 1959 | O   | THR | 200 | 72.499 | 38.747 | -3.142 | 1.00 | 56.02 | R1 |
| ATOM | 1960 | N   | LEU | 201 | 74.557 | 37.865 | -3.439 | 1.00 | 58.19 | R1 |
| ATOM | 1961 | H   | LEU | 201 | 75.156 | 37.391 | -4.054 | 1.00 | 35.00 | R1 |
| ATOM | 1962 | CA  | LEU | 201 | 75.045 | 38.221 | -2.104 | 1.00 | 61.38 | R1 |
| ATOM | 1963 | CB  | LEU | 201 | 75.996 | 37.132 | -1.581 | 1.00 | 62.83 | R1 |
| ATOM | 1964 | CG  | LEU | 201 | 75.360 | 35.824 | -1.098 | 1.00 | 62.01 | R1 |
| ATOM | 1965 | CD1 | LEU | 201 | 76.448 | 34.839 | -0.710 | 1.00 | 62.78 | R1 |
| ATOM | 1966 | CD2 | LEU | 201 | 74.417 | 36.093 | 0.084  | 1.00 | 63.43 | R1 |
| ATOM | 1967 | C   | LEU | 201 | 75.665 | 39.591 | -1.843 | 1.00 | 62.98 | R1 |
| ATOM | 1968 | O   | LEU | 201 | 76.727 | 39.916 | -2.365 | 1.00 | 63.46 | R1 |
| ATOM | 1969 | N   | GLU | 202 | 75.001 | 40.367 | -0.990 | 1.00 | 65.68 | R1 |
| ATOM | 1970 | H   | GLU | 202 | 74.158 | 40.032 | -0.621 | 1.00 | 35.00 | R1 |
| ATOM | 1971 | CA  | GLU | 202 | 75.470 | 41.693 | -0.571 | 1.00 | 70.04 | R1 |
| ATOM | 1972 | CB  | GLU | 202 | 76.629 | 41.534 | 0.435  | 1.00 | 67.57 | R1 |
| ATOM | 1973 | CG  | GLU | 202 | 76.293 | 40.737 | 1.723  | 1.00 | 65.39 | R1 |
| ATOM | 1974 | CD  | GLU | 202 | 76.410 | 39.212 | 1.571  | 1.00 | 65.28 | R1 |
| ATOM | 1975 | OE1 | GLU | 202 | 75.451 | 38.495 | 1.944  | 1.00 | 62.21 | R1 |
| ATOM | 1976 | OE2 | GLU | 202 | 77.465 | 38.727 | 1.101  | 1.00 | 63.57 | R1 |
| ATOM | 1977 | C   | GLU | 202 | 75.851 | 42.708 | -1.677 | 1.00 | 69.66 | R1 |
| ATOM | 1978 | O   | GLU | 202 | 75.884 | 42.368 | -2.866 | 1.00 | 72.13 | R1 |
| ATOM | 1979 | N   | GLU | 203 | 76.124 | 43.953 | -1.264 | 1.00 | 71.10 | R1 |
| ATOM | 1980 | H   | GLU | 203 | 76.068 | 44.139 | -0.304 | 1.00 | 35.00 | R1 |
| ATOM | 1981 | CA  | GLU | 203 | 76.510 | 45.064 | -2.154 | 1.00 | 71.11 | R1 |
| ATOM | 1982 | CB  | GLU | 203 | 77.640 | 44.646 | -3.110 | 1.00 | 69.26 | R1 |
| ATOM | 1983 | CG  | GLU | 203 | 78.909 | 44.157 | -2.410 | 1.00 | 67.87 | R1 |
| ATOM | 1984 | CD  | GLU | 203 | 79.759 | 43.239 | -3.287 | 1.00 | 67.93 | R1 |
| ATOM | 1985 | OE1 | GLU | 203 | 79.213 | 42.247 | -3.823 | 1.00 | 68.04 | R1 |
| ATOM | 1986 | OE2 | GLU | 203 | 80.976 | 43.501 | -3.428 | 1.00 | 65.93 | R1 |
| ATOM | 1987 | C   | GLU | 203 | 75.342 | 45.683 | -2.938 | 1.00 | 71.54 | R1 |
| ATOM | 1988 | O   | GLU | 203 | 74.834 | 45.050 | -3.893 | 1.00 | 71.76 | R1 |
| ATOM | 1989 | C1  | SM1 | 1   | 73.136 | 27.056 | 5.463  | 1.00 | 23.77 | I  |
| ATOM | 1990 | N2  | SM1 | 1   | 74.200 | 26.342 | 4.720  | 1.00 | 19.07 | I  |
| ATOM | 1991 | C3  | SM1 | 1   | 72.537 | 28.232 | 4.642  | 1.00 | 25.81 | I  |
| ATOM | 1992 | C4  | SM1 | 1   | 72.081 | 26.054 | 5.878  | 1.00 | 24.52 | I  |
| ATOM | 1993 | O5  | SM1 | 1   | 72.187 | 25.524 | 6.971  | 1.00 | 26.27 | I  |
| ATOM | 1994 | C6  | SM1 | 1   | 71.791 | 29.256 | 5.473  | 1.00 | 27.98 | I  |
| ATOM | 1995 | C7  | SM1 | 1   | 71.820 | 29.467 | 6.828  | 1.00 | 27.66 | I  |
| ATOM | 1996 | C8  | SM1 | 1   | 70.826 | 30.305 | 5.017  | 1.00 | 29.41 | I  |
| ATOM | 1997 | C9  | SM1 | 1   | 70.371 | 30.606 | 3.730  | 1.00 | 25.66 | I  |
| ATOM | 1998 | C10 | SM1 | 1   | 70.414 | 30.982 | 6.113  | 1.00 | 30.81 | I  |
| ATOM | 1999 | N11 | SM1 | 1   | 71.014 | 30.477 | 7.206  | 1.00 | 30.77 | I  |
| ATOM | 2000 | C12 | SM1 | 1   | 69.446 | 31.660 | 3.608  | 1.00 | 25.20 | I  |
| ATOM | 2001 | C13 | SM1 | 1   | 69.497 | 32.037 | 6.032  | 1.00 | 31.26 | I  |
| ATOM | 2002 | C14 | SM1 | 1   | 69.013 | 32.370 | 4.750  | 1.00 | 29.20 | I  |
| ATOM | 2003 | C15 | SM1 | 1   | 67.956 | 22.768 | 2.873  | 1.00 | 22.91 | I  |
| ATOM | 2004 | C16 | SM1 | 1   | 70.019 | 24.796 | 5.393  | 1.00 | 25.16 | I  |
| ATOM | 2005 | N17 | SM1 | 1   | 71.061 | 25.761 | 5.028  | 1.00 | 27.92 | I  |
| ATOM | 2006 | C18 | SM1 | 1   | 69.083 | 25.405 | 6.483  | 1.00 | 20.27 | I  |
| ATOM | 2007 | C19 | SM1 | 1   | 69.239 | 24.398 | 4.151  | 1.00 | 25.82 | I  |
| ATOM | 2008 | O20 | SM1 | 1   | 69.059 | 25.235 | 3.272  | 1.00 | 23.22 | I  |
| ATOM | 2009 | C21 | SM1 | 1   | 67.985 | 26.262 | 5.824  | 1.00 | 18.08 | I  |
| ATOM | 2010 | C22 | SM1 | 1   | 66.742 | 25.699 | 5.516  | 1.00 | 15.97 | I  |
| ATOM | 2011 | C23 | SM1 | 1   | 68.230 | 27.601 | 5.503  | 1.00 | 18.27 | I  |
| ATOM | 2012 | C24 | SM1 | 1   | 65.761 | 26.465 | 4.879  | 1.00 | 17.15 | I  |
| ATOM | 2013 | C25 | SM1 | 1   | 67.247 | 28.370 | 4.871  | 1.00 | 18.76 | I  |
| ATOM | 2014 | C26 | SM1 | 1   | 66.010 | 27.800 | 4.554  | 1.00 | 19.84 | I  |
| ATOM | 2015 | O27 | SM1 | 1   | 65.039 | 28.555 | 3.885  | 1.00 | 27.62 | I  |
| ATOM | 2016 | C28 | SM1 | 1   | 62.541 | 24.291 | 0.185  | 1.00 | 23.87 | I  |
| ATOM | 2017 | N29 | SM1 | 1   | 68.738 | 23.142 | 4.045  | 1.00 | 21.38 | I  |
| ATOM | 2018 | C30 | SM1 | 1   | 68.469 | 21.452 | 2.213  | 1.00 | 22.06 | I  |
| ATOM | 2019 | C31 | SM1 | 1   | 66.511 | 22.781 | 3.337  | 1.00 | 23.46 | I  |
| ATOM | 2020 | O32 | SM1 | 1   | 66.313 | 22.861 | 4.536  | 1.00 | 23.98 | I  |
| ATOM | 2021 | C33 | SM1 | 1   | 68.078 | 20.136 | 2.938  | 1.00 | 22.60 | I  |
| ATOM | 2022 | C34 | SM1 | 1   | 68.838 | 18.933 | 2.402  | 1.00 | 22.08 | I  |
| ATOM | 2023 | N35 | SM1 | 1   | 69.396 | 18.970 | 1.171  | 1.00 | 19.06 | I  |
| ATOM | 2024 | O36 | SM1 | 1   | 68.922 | 17.935 | 3.110  | 1.00 | 18.62 | I  |
| ATOM | 2025 | P37 | SM1 | 1   | 64.028 | 29.351 | 4.839  | 1.00 | 31.67 | I  |
| ATOM | 2026 | N38 | SM1 | 1   | 65.461 | 22.723 | 2.480  | 1.00 | 26.21 | I  |

TABLE 3-continued

Crystallographic coordinates for the refined co-crystal

| | | | | | | | | | |
|---|---|---|---|---|---|---|---|---|---|
| ATOM | 2027 | C39 | SM1 | 1 | 62.715 | 24.299 | −1.319 | 1.00 | 23.46 I |
| ATOM | 2028 | O40 | SM1 | 1 | 61.429 | 24.495 | 0.638 | 1.00 | 27.25 I |
| ATOM | 2029 | C41 | SM1 | 1 | 63.221 | 25.666 | −1.802 | 1.00 | 23.35 I |
| ATOM | 2030 | C42 | SM1 | 1 | 62.395 | 26.791 | −1.705 | 1.00 | 21.90 I |
| ATOM | 2031 | C43 | SM1 | 1 | 64.508 | 25.787 | −2.338 | 1.00 | 19.34 I |
| ATOM | 2032 | C44 | SM1 | 1 | 62.857 | 28.036 | −2.144 | 1.00 | 20.57 I |
| ATOM | 2033 | C45 | SM1 | 1 | 64.967 | 27.033 | −2.775 | 1.00 | 17.54 I |
| ATOM | 2034 | C46 | SM1 | 1 | 64.143 | 28.158 | −2.676 | 1.00 | 16.26 I |
| ATOM | 2035 | O47 | SM1 | 1 | 64.596 | 29.401 | −3.106 | 1.00 | 15.34 I |
| ATOM | 2036 | O48 | SM1 | 1 | 64.543 | 30.728 | 5.098 | 1.00 | 24.33 I |
| ATOM | 2037 | O49 | SM1 | 1 | 62.627 | 29.453 | 4.073 | 1.00 | 30.32 I |
| ATOM | 2038 | O50 | SM1 | 1 | 63.833 | 28.560 | 6.222 | 1.00 | 29.70 I |
| ATOM | 2039 | N51 | SM1 | 1 | 63.609 | 24.061 | 0.988 | 1.00 | 24.25 I |
| ATOM | 2040 | C52 | SM1 | 1 | 64.921 | 23.827 | 0.371 | 1.00 | 27.61 I |
| ATOM | 2041 | C53 | SM1 | 1 | 65.656 | 22.634 | 1.038 | 1.00 | 26.96 I |
| ATOM | 2042 | C54 | SM1 | 1 | 64.101 | 22.767 | 3.009 | 1.00 | 23.10 I |
| ATOM | 2043 | C55 | SM1 | 1 | 63.439 | 24.049 | 2.442 | 1.00 | 18.12 I |
| ATOM | 2044 | C1 | SM1 | 1 | 66.684 | 29.276 | −7.283 | 1.00 | 23.73 I2 |
| ATOM | 2045 | N2 | SM1 | 1 | 66.734 | 29.406 | −8.753 | 1.00 | 26.73 I2 |
| ATOM | 2046 | C3 | SM1 | 1 | 66.370 | 30.603 | −6.538 | 1.00 | 25.61 I2 |
| ATOM | 2047 | C4 | SM1 | 1 | 65.808 | 28.113 | −6.854 | 1.00 | 21.71 I2 |
| ATOM | 2048 | O5 | SM1 | 1 | 66.139 | 27.516 | −5.848 | 1.00 | 31.33 I2 |
| ATOM | 2049 | C6 | SM1 | 1 | 64.922 | 31.014 | −6.697 | 1.00 | 30.61 I2 |
| ATOM | 2050 | C7 | SM1 | 1 | 63.917 | 30.397 | −7.399 | 1.00 | 28.52 I2 |
| ATOM | 2051 | C8 | SM1 | 1 | 64.212 | 32.199 | −6.132 | 1.00 | 31.76 I2 |
| ATOM | 2052 | C9 | SM1 | 1 | 64.700 | 33.220 | −5.321 | 1.00 | 30.34 I2 |
| ATOM | 2053 | C10 | SM1 | 1 | 62.926 | 32.142 | −6.549 | 1.00 | 32.97 I2 |
| ATOM | 2054 | N11 | SM1 | 1 | 62.746 | 31.054 | −7.316 | 1.00 | 31.31 I2 |
| ATOM | 2055 | C12 | SM1 | 1 | 63.783 | 34.215 | −4.942 | 1.00 | 31.27 I2 |
| ATOM | 2056 | C13 | SM1 | 1 | 61.988 | 33.111 | −6.192 | 1.00 | 33.17 I2 |
| ATOM | 2057 | C14 | SM1 | 1 | 62.438 | 34.162 | −5.372 | 1.00 | 31.19 I2 |
| ATOM | 2058 | C15 | SM1 | 1 | 60.932 | 24.935 | −8.883 | 1.00 | 29.57 I2 |
| ATOM | 2059 | C16 | SM1 | 1 | 63.930 | 26.572 | −7.064 | 1.00 | 20.14 I2 |
| ATOM | 2060 | N17 | SM1 | 1 | 64.719 | 27.710 | −7.562 | 1.00 | 21.00 I2 |
| ATOM | 2061 | C18 | SM1 | 1 | 63.091 | 26.998 | −5.825 | 1.00 | 22.75 I2 |
| ATOM | 2062 | C19 | SM1 | 1 | 63.082 | 25.965 | −8.162 | 1.00 | 21.87 I2 |
| ATOM | 2063 | O20 | SM1 | 1 | 63.566 | 25.883 | −9.281 | 1.00 | 20.91 I2 |
| ATOM | 2064 | C21 | SM1 | 1 | 61.744 | 27.603 | −6.257 | 1.00 | 21.13 I2 |
| ATOM | 2065 | C22 | SM1 | 1 | 60.541 | 27.133 | −5.712 | 1.00 | 21.90 I2 |
| ATOM | 2066 | C23 | SM1 | 1 | 61.715 | 28.612 | −7.218 | 1.00 | 24.32 I2 |
| ATOM | 2067 | C24 | SM1 | 1 | 59.321 | 27.668 | −6.137 | 1.00 | 20.64 I2 |
| ATOM | 2068 | C25 | SM1 | 1 | 60.500 | 29.152 | −7.643 | 1.00 | 26.88 I2 |
| ATOM | 2069 | C26 | SM1 | 1 | 59.300 | 28.678 | −7.108 | 1.00 | 29.47 I2 |
| ATOM | 2070 | O27 | SM1 | 1 | 58.095 | 29.208 | −7.573 | 1.00 | 32.74 I2 |
| ATOM | 2071 | C28 | SM1 | 1 | 62.029 | 28.096 | −14.059 | 1.00 | 35.94 I2 |
| ATOM | 2072 | N29 | SM1 | 1 | 61.821 | 25.530 | −7.874 | 1.00 | 22.58 I2 |
| ATOM | 2073 | C30 | SM1 | 1 | 60.030 | 23.838 | −8.229 | 1.00 | 26.17 I2 |
| ATOM | 2074 | C31 | SM1 | 1 | 60.121 | 26.038 | −9.546 | 1.00 | 32.77 I2 |
| ATOM | 2075 | O32 | SM1 | 1 | 59.387 | 26.714 | −8.840 | 1.00 | 35.53 I2 |
| ATOM | 2076 | C33 | SM1 | 1 | 58.574 | 24.309 | −7.919 | 1.00 | 29.41 I2 |
| ATOM | 2077 | C34 | SM1 | 1 | 57.505 | 23.255 | −8.190 | 1.00 | 35.47 I2 |
| ATOM | 2078 | N35 | SM1 | 1 | 56.198 | 23.624 | −8.293 | 1.00 | 33.23 I2 |
| ATOM | 2079 | O36 | SM1 | 1 | 57.843 | 22.080 | −8.299 | 1.00 | 30.92 I2 |
| ATOM | 2080 | P37 | SM1 | 1 | 57.260 | 29.913 | −6.406 | 1.00 | 45.95 I2 |
| ATOM | 2081 | N38 | SM1 | 1 | 60.203 | 26.275 | −10.885 | 1.00 | 34.56 I2 |
| ATOM | 2082 | C39 | SM1 | 1 | 62.879 | 27.286 | −15.015 | 1.00 | 33.95 I2 |
| ATOM | 2083 | O40 | SM1 | 1 | 62.145 | 29.313 | −14.082 | 1.00 | 38.04 I2 |
| ATOM | 2084 | C41 | SM1 | 1 | 64.134 | 26.725 | −14.323 | 1.00 | 33.78 I2 |
| ATOM | 2085 | C42 | SM1 | 1 | 65.389 | 26.877 | −14.929 | 1.00 | 32.07 I2 |
| ATOM | 2086 | C43 | SM1 | 1 | 64.030 | 26.051 | −13.097 | 1.00 | 30.70 I2 |
| ATOM | 2087 | C44 | SM1 | 1 | 66.535 | 26.361 | −14.310 | 1.00 | 31.84 I2 |
| ATOM | 2088 | C45 | SM1 | 1 | 65.175 | 25.535 | −12.479 | 1.00 | 31.45 I2 |
| ATOM | 2089 | C46 | SM1 | 1 | 66.428 | 25.690 | −13.087 | 1.00 | 31.05 I2 |
| ATOM | 2090 | O47 | SM1 | 1 | 67.574 | 25.184 | −12.474 | 1.00 | 29.19 I2 |
| ATOM | 2091 | O48 | SM1 | 1 | 58.115 | 30.957 | −5.757 | 1.00 | 39.41 I2 |
| ATOM | 2092 | O49 | SM1 | 1 | 55.949 | 30.584 | −7.048 | 1.00 | 41.04 I2 |
| ATOM | 2093 | O50 | SM1 | 1 | 56.805 | 28.819 | −5.323 | 1.00 | 38.48 I2 |
| ATOM | 2094 | N51 | SM1 | 1 | 61.163 | 27.476 | −13.209 | 1.00 | 36.30 I2 |
| ATOM | 2095 | C52 | SM1 | 1 | 61.044 | 26.015 | −13.207 | 1.00 | 34.52 I2 |
| ATOM | 2096 | C53 | SM1 | 1 | 61.079 | 25.473 | −11.747 | 1.00 | 35.21 I2 |
| ATOM | 2097 | C54 | SM1 | 1 | 59.405 | 27.348 | −11.472 | 1.00 | 35.74 I2 |
| ATOM | 2098 | C55 | SM1 | 1 | 60.344 | 28.275 | −12.293 | 1.00 | 36.72 I2 |
| END | | | | | | | | | |

Example 3

Assay for Interleukin-1 Receptor Antagonist Activity

The compounds of the invention can be tested for interleukin-1 receptor antagonist activity by using a competitive assay and labeled IL-1a. IL-1R1 protein is immobilized on 96-well plates. The plates are washed with binding buffer, and then binding buffer containing $^{125}$I-IL-1a is added to each well to begin the assay. A compound of the invention is then added and the plates are incubated for two hours at 4° C. After the two hour incubation, the wells are rinsed with ice cold PBS. The receptors are then detached from the plates by adding 0.1 N NaOH to each well. The suspension is counted on a gamma counter, and the $IC_{50}$ for each compound is determined using computer assistance and the gamma counting.

It should be understood that the foregoing disclosure emphasizes certain specific embodiments of the invention and that all modifications or alternatives equivalent thereto are within the spirit and scope of the invention as set forth in the appended claims.

---

We claim:

1. A crystal having a space group R3 and a unit cell dimension of a=96.3 Å, b=96.3 Å, and c=75.3 Å of a protein-ligand complex comprising a modified IL-1 receptor type 1 (IL-1R1) and a ligand, wherein:
   a. the modified IL-1 receptor type 1 consists of the amino acid sequence as set forth in SEQ ID NO: 2;
   b. the ligand forms a complex with the modified IL-1 receptor type 1 by binding to the amino acid sequence as set forth in SEQ ID NO: 2 and has a molecular weight of less than about 1500 g/mol; and
   c. the crystal effectively diffracts X-rays for the determination of atomic coordinates of the protein-ligand complex to a better resolution than 3.5 Angstroms.

2. The crystal of claim 1 having a three-dimensional structure characterized by the atomic structure coordinates of Table 3.

3. A method for preparing a crystal of a modified IL-1 receptor type 1 protein-ligand complex consisting of:

a. making a first solution of 7.2 mg/mL of a complex of IL-1 receptor type 1 protein of SEQ ID NO: 2 and a ligand, 20 mM HEPES pH 75, 130 mM NaCl, and 0.25% Chaps;

b. mixing an equal volume of the first solution with a precipitant solution of 30% PEG4K and 100 mM Na Citrate, pH 5.7 in a drop;

c. using a hanging drop method wherein the drop is placed over 1 mL of said precipitant Solution.

4. A crystal prepared according to the method of claim 3.

* * * * *